(12) United States Patent
Chappell, III et al.

(10) Patent No.: US 12,274,551 B2
(45) Date of Patent: Apr. 15, 2025

(54) CONTENT GENERATION AND CONTROL USING SENSOR DATA FOR DETECTION OF NEUROLOGICAL STATE

(71) Applicant: WARNER BROS. ENTERTAINMENT INC., Burbank, CA (US)

(72) Inventors: Arvel A. Chappell, III, Los Angeles, CA (US); Lewis S. Ostrover, Los Angeles, CA (US); Harold C. Mack, Los Angeles, CA (US)

(73) Assignee: Warner Bros. Entertainment Inc., Burbank, CA (US)

( * ) Notice: Subject to any disclaimer, the term of this patent is extended or adjusted under 35 U.S.C. 154(b) by 81 days.

(21) Appl. No.: 16/923,053

(22) Filed: Jul. 7, 2020

(65) Prior Publication Data

US 2020/0405213 A1    Dec. 31, 2020

Related U.S. Application Data

(63) Continuation of application No. PCT/US2019/012783, filed on Jan. 8, 2019.
(Continued)

(51) Int. Cl.
*A61B 5/00* (2006.01)
*A61B 5/0533* (2021.01)
(Continued)

(52) U.S. Cl.
CPC ............ *A61B 5/165* (2013.01); *A61B 5/0042* (2013.01); *A61B 5/0075* (2013.01);
(Continued)

(58) Field of Classification Search
CPC .......... A61B 5/16; A61B 5/165; A61B 5/369; A61B 5/318; A61B 5/389; A61B 5/316;
(Continued)

(56) References Cited

U.S. PATENT DOCUMENTS 4,305,131 A  12/1981  Best
8,069,125 B2  11/2011  Jung et al.
(Continued)

FOREIGN PATENT DOCUMENTS

CN  101578065 A  11/2009
CN  102289347 A  12/2011
(Continued)

OTHER PUBLICATIONS

WO, PCT/US2018/053625 ISR and Written Opinion, Dec. 27, 2018.
(Continued)

*Primary Examiner* — Sana Sahand
(74) *Attorney, Agent, or Firm* — Bookoff McAndrews, PLLC

(57) ABSTRACT

Applications for a Content Engagement Power (CEP) value include generating a script, text, or other communication content or for controlling playout of communication content based on neuro-physiological data, gathering neuro-physiological data correlated to consumption of communication content, or rating effectiveness of personal communications. The CEP is computed based on neuro-physiological sensor data processed to express engagement with content along multiple dimensions such as valence, arousal, and dominance. An apparatus is configured to perform the method using hardware, firmware, and/or software.

20 Claims, 24 Drawing Sheets

Related U.S. Application Data

(60) Provisional application No. 62/715,766, filed on Aug. 7, 2018, provisional application No. 62/661,556, filed on Apr. 23, 2018, provisional application No. 62/614,811, filed on Jan. 8, 2018.

(51) Int. Cl.

| | |
|---|---|
| A61B 5/055 | (2006.01) |
| A61B 5/16 | (2006.01) |
| A61B 5/316 | (2021.01) |
| A61B 5/318 | (2021.01) |
| A61B 5/369 | (2021.01) |
| A61B 5/389 | (2021.01) |
| A63F 13/212 | (2014.01) |
| A63F 13/352 | (2014.01) |
| A63F 13/79 | (2014.01) |
| G06F 3/01 | (2006.01) |
| G06Q 50/00 | (2012.01) |
| G10L 15/04 | (2013.01) |
| G16H 40/67 | (2018.01) |
| G16H 50/30 | (2018.01) |
| H04N 21/422 | (2011.01) |
| H04N 21/442 | (2011.01) |
| H04N 21/845 | (2011.01) |

(52) U.S. Cl.
CPC .......... *A61B 5/0077* (2013.01); *A61B 5/0533* (2013.01); *A61B 5/055* (2013.01); *A61B 5/161* (2013.01); *A61B 5/316* (2021.01); *A61B 5/318* (2021.01); *A61B 5/369* (2021.01); *A61B 5/389* (2021.01); *A61B 5/7246* (2013.01); *A63F 13/212* (2014.09); *A63F 13/352* (2014.09); *A63F 13/79* (2014.09); *G06F 3/015* (2013.01); *G06Q 50/01* (2013.01); *G10L 15/04* (2013.01); *G16H 40/67* (2018.01); *G16H 50/30* (2018.01); *H04N 21/42201* (2013.01); *H04N 21/44218* (2013.01); *H04N 21/8456* (2013.01)

(58) Field of Classification Search
CPC ... A61B 5/0042; A61B 5/0075; A61B 5/0077; A61B 5/0533; A61B 5/055; A63F 13/352; G10L 15/04

See application file for complete search history.

(56) References Cited

U.S. PATENT DOCUMENTS

| | | | |
|---|---|---|---|
| 9,304,621 | B1 | 4/2016 | Wakim et al. |
| 9,736,603 | B2 | 8/2017 | Osborne et al. |
| 9,788,777 | B1 | 10/2017 | Knight et al. |
| 10,025,972 | B2 | 7/2018 | Matas et al. |
| 10,880,601 | B1 | 12/2020 | Donahoe |
| 2002/0059379 | A1 | 5/2002 | Harvey et al. |
| 2002/0073417 | A1 | 6/2002 | Kondo et al. |
| 2007/0168315 | A1 | 7/2007 | Covannon et al. |
| 2007/0265507 | A1 | 11/2007 | de Lemos |
| 2008/0161109 | A1* | 7/2008 | Chainer ............ A63F 13/212 463/36 |
| 2009/0036756 | A1* | 2/2009 | Pradeep ............ A61B 5/16 600/301 |
| 2009/0163777 | A1 | 6/2009 | Jung et al. |
| 2010/0070987 | A1 | 3/2010 | Amento et al. |
| 2010/0087251 | A1 | 4/2010 | Collar et al. |
| 2010/0211439 | A1 | 8/2010 | Marci et al. |
| 2010/0302000 | A1 | 12/2010 | Szymkowiak et al. |
| 2011/0009193 | A1 | 1/2011 | Bond et al. |
| 2011/0169603 | A1 | 7/2011 | Fithian et al. |
| 2011/0320536 | A1 | 12/2011 | Lobb et al. |
| 2012/0072939 | A1 | 3/2012 | Crenshaw |
| 2012/0077162 | A1 | 3/2012 | Veen et al. |
| 2012/0324492 | A1 | 12/2012 | Treadwell, III et al. |
| 2013/0046577 | A1 | 2/2013 | Marci et al. |
| 2013/0102923 | A1 | 4/2013 | Cas et al. |
| 2013/0232515 | A1 | 9/2013 | Rivera et al. |
| 2013/0247081 | A1 | 9/2013 | Vinson et al. |
| 2013/0268954 | A1 | 10/2013 | Hulten et al. |
| 2013/0280682 | A1 | 10/2013 | Levine et al. |
| 2013/0283162 | A1* | 10/2013 | Aronsson ............ G11B 27/105 715/719 |
| 2013/0288777 | A1 | 10/2013 | Short et al. |
| 2014/0130076 | A1* | 5/2014 | Moore ............ H04N 21/25883 725/19 |
| 2014/0150002 | A1 | 5/2014 | Hough et al. |
| 2014/0221866 | A1 | 8/2014 | Quy |
| 2014/0270683 | A1 | 9/2014 | Zhu et al. |
| 2014/0350349 | A1 | 11/2014 | Geurts et al. |
| 2015/0093729 | A1 | 4/2015 | Plans et al. |
| 2015/0127737 | A1 | 5/2015 | Thompson et al. |
| 2015/0142553 | A1 | 5/2015 | Kodra et al. |
| 2015/0181291 | A1* | 6/2015 | Wheatley ............ H04N 21/84 725/10 |
| 2015/0193089 | A1 | 7/2015 | Berlin et al. |
| 2015/0248615 | A1 | 9/2015 | Parra et al. |
| 2016/0042648 | A1 | 2/2016 | Kothuri |
| 2016/0077547 | A1 | 3/2016 | Aimone et al. |
| 2016/0144278 | A1 | 5/2016 | el Kaliouby et al. |
| 2016/0191893 | A1 | 6/2016 | Gewickey et al. |
| 2016/0196105 | A1 | 7/2016 | Vartakavi et al. |
| 2016/0228744 | A1 | 8/2016 | Szacherski |
| 2017/0055033 | A1 | 2/2017 | Christie |
| 2017/0061704 | A1 | 3/2017 | Gewicke et al. |
| 2017/0061970 | A1 | 3/2017 | Escott et al. |
| 2017/0123824 | A1 | 5/2017 | Franck |
| 2017/0147202 | A1 | 5/2017 | Donohue |
| 2017/0169727 | A1 | 6/2017 | Briggs et al. |
| 2017/0171614 | A1 | 6/2017 | el Kaliouby et al. |
| 2017/0243055 | A1 | 8/2017 | Naveh |
| 2017/0251262 | A1 | 8/2017 | Bist et al. |
| 2018/0205989 | A1 | 7/2018 | Srinivasan et al. |
| 2018/0376187 | A1 | 12/2018 | Everett et al. |
| 2019/0090020 | A1 | 3/2019 | Srivastava et al. |
| 2019/0297380 | A1 | 9/2019 | Dominguez et al. |
| 2019/0379938 | A1 | 12/2019 | Salo et al. |
| 2020/0060598 | A1 | 2/2020 | Palti-Wasserman |
| 2020/0134084 | A1 | 4/2020 | Rakshit et al. |
| 2020/0267451 | A1 | 8/2020 | Pudhiyaveetil et al. |
| 2020/0296458 | A1 | 9/2020 | Chappell, III et al. |
| 2020/0296480 | A1 | 9/2020 | Chappell, III et al. |
| 2020/0297262 | A1 | 9/2020 | Chappell, III et al. |
| 2020/0405212 | A1 | 12/2020 | Chappell, III et al. |
| 2021/0056407 | A1 | 2/2021 | Buesser et al. |

FOREIGN PATENT DOCUMENTS

| | | |
|---|---|---|
| CN | 102802515 A | 11/2012 |
| CN | 104541328 A | 4/2015 |
| CN | 204630657 U | 9/2015 |
| CN | 105610884 A | 5/2016 |
| CN | 106030642 A | 10/2016 |
| JP | 2013131172 A | 7/2013 |
| JP | 2015163210 A | 9/2015 |
| RU | 94030307 A | 10/1996 |
| WO | WO 2016/172557 A1 | 10/2016 |
| WO | 2017214040 A1 | 12/2017 |

OTHER PUBLICATIONS

WO, PCT/US2018/053218 ISR and Written Opinion, Jan. 17, 2019.
WO, PCT/US2018/053614 ISR and Written Opinion, Jan. 17, 2019.
WO, PCT/US2019/012567 ISR and Written Opinion, Apr. 11, 2019.
WO, PCT/US2019/012783 ISR and Written Opinion, Apr. 25, 2019.
"#613: Storytelling in VR from a Depth Psychological & Mythological Perspective", 2018, retrieved from https://voicesofvr.com/613-storytelling-in-vr-from-a-depth-psychological-mythological-perspective/, pp. 1-4.

(56) References Cited

OTHER PUBLICATIONS

"Ad firms using tools to help them read your mind", 2017, retrieved from https://technology.inquirer.net/70804/ad-firms-using-tools-help-read-mind, pp. 1-7.
"Aside", 2016, retrieved from https://web.archive.org/web/20161117103448/htpps://en.wikipedia.org/wiki/Aside, 2 pages.
Bound, K., "AI: discover how viewer emotions guide the narrative direction of a movie", 2018, retrieved from https://www.linkedin.com/pulse/ai-how-viewer-emotions-guide-narrative-direction-keith, pp. 1-5.
Breland, A., "Facebook patents technology that would estimate users' socioeconomic status", 2018, retrieved from https://thehill.com/policy/technology/372017-facebook-patents-tech-to-estimate-users-socioeconomic-status, pp. 1-2.
Castellanos, S., "Siri Contributor Tackles Software That Detects Emotional States", 2018, retrieved from https://www.wsj.com/articles/siri-contributor-tackles-software-that-detects-emotional-states-1520548561, pp. 1-2.
Chan, S., "Interaxon measures brainwaves to give VR devs more data for game design", 2018, retrieved from https://venturebeat.com/2018/01/13/interaxon-measures-brainwaves-to-give-vr-devs-more-data-for-game-design/, pp. 1-6.
Coldeway, D., "This facial recognition system tracks how you're enjoying a movie", 2017, retrieved from https://techcrunch.com/2017/07/25/this-facial-recognition-system-tracks-how-youre-enjoying-a-movie/, pp. 1-2.
Crooke, J., "Uber applies for patent that would protect drunk passengers", 2018, retrieved from https://techcrunch.com/2018/06/11/uber-applies-for-patent-that-would-detect-drunk-passengers/, pp. 1-3.
Dormehl, L., "Frighteningly accurate 'mind reading' AI reads brain scans to guess what you're thinking", 2017, retrieved from https://www.digitaltrends.com/cool-tech/ai-predicts-what-youre-thinking/, pp. 1-8.
Dormehl, L., "New VR horror game gets scarier if your heart rate isn't fast enough", 218, retrieved from https://www.digitaltrends.com/cool-tech/bring-to-light-heart-rate-vr/, pp. 1-7.
Fadelli, I., "Researchers use machine learning to analyse movie preferences", 2018, retrieved from https://techxplore.com/news/2018-07-machine-analyse-movie.html, pp. 1-3.
Grant, C., "Many Worlds: The movie that watches its audience", BBQ News, retrieved from https://www.bbc.com/news/technology-21429437, 2013, pp. 1-5.
Harman, A., "Ford Research Gives New Meaning to 'Rush Hour'", 2018, retrieved from https://www.wardsauto.com/industry/ford-research-gives-new-meaning-rush-hour, pp. 1-7.
Hasson, U., et al., "Neurocinematics: The Neuroscience of Film", Projections, 2008, vol. 2, No. 1, pp. 1-26.
Kapur, A., et al., "AlterEgo: A Personalized Wearable Silent Speech Interface", IUI '18: 23rd International Conference on Intelligent User Interfaces, Mar. 2018, Tokyo, Japan, pp. 43-53.
Kaufman, D., "NAB 2018: Machine-Learning Tools to Become Vital for Editing", 2018, retrieved from https://www.etcentric.org/nab-2018-machine-learning-tools-to-beomce-vital-for-editing/), pp. 1-3.
Kaufman, D., "NAB 2018: Potential Impact of AI on Storytelling, Moviemaking", 2018, retrieved from https://www.etcentric.org/nab-2018-potentialimpact-of-ai-on-storytelling-moviemaking/, pp. 1-3.
Lefebvre, R., "MIT's wearable device can 'hear' the words you say in your head", 2018, retrieved from https://www.engadget.com/2018-04-06-mit-wearable-silent-words.html, pp. 1-7.
Marsella, S., et al., "Computational Models of Emotion", Draft Manuscript, pp. 1-30.
Parker, L., "Video Game Creators Seek Ouy Hollywood for Robust Narratives", 2017, retrieved from https://www.nytimes.com/2017/12/20/technology/video-game-creators-hollywood-writers.html#:~:text=When%20Pete%20Samuels%2C%20a%20founder,So%20he%20turned%20to%20Hollywood., pp. 1-4.
Riedl, M. O., et al., "From Linear Story Generation to Branching Story Graphs", IEEE Computer Graphics and Applications, 2006, pp. 23-31.
Siegel, T., "This New Artificial Intelligence Script-Reading Program Could Find Your Next Oscar Role (Exclusive)", 2016, retrieved from https://www.hollywoodreporter.com/news/general-news/new-artificial-intelligence-script-reading-866554/, pp. 1-3.
Solsman, J. E., et al., "Oculus wants to make immersive virtual theater a reality", 2018, retrieved from https://www.cnet.com/tech/mobile/oculus-wants-to-make-immersive-virtual-theater-a-reality/, pp. 1-4.
Simonite, T., "This Call May Be Monitored for Tone and Emotion", 2018, retrieved from https://www.wired.com/story/this-call-may-be-monitored-for-tone-and-emotion/, pp. 1-8.
Trew, J., "Dolby knows what you're feeling at the movies", 2018, retrieved from https://www.engadget.com/2018-01-12-dolby-knows-what-youre-watching-based-on-your-b.html, pp. 1-5.
Turk, V., "Shakespeare, Remixed by Biosensors", 2014, retrieved from https://www.vice.com/en/article/bmjmd8/shakespeare-remixed-by-biosensors, 7 pages.
"Turning Design Mockups Into Code With Deep Learning", 2018, retrieved from https://blog.floydhub.com/turning-design-mockups-into-code-with-deep-learning/, pp. 1-41.
Waltz, E., "A New Wearable Brain Scanner", 2018, retrieved from https://spectrum.ieee.org/the-human-os/biomedical/imaging/a-new-wearable-brain-scanner, pp. 1-4.
Wang, J., et al., "Predicting the Brain Activation Pattern Associated With the Propositional Content of a Sentence: Modeling Neural Representations of Events and States", Human Brain Mapping, 2017, vol. 38, No. 10, pp. 4865-4881.
Webb, A., "Apple is Developing an EKG Heart Monitor for Its Smartwatch", 2017, retrieved from https://www.bloomberg.com/news/articles/2017-12-21/apple-is-said-to-develop-ekg-heart-monitor-for-future-watch, pp. 1-2.
EP, 19735809.6 Partial Supplementary Search Report, Nov. 4, 2021.
Gilroy, S. W., et al., "Exploring Passive User Interaction for Adaptive Narratives", Proceedings of the 2012 ACM international conference on Intelligent User Interfaces, 2012, Session: Designing Narratives & Theater, Lisbon, Portugal, pp. 119-128.
Katti, H., et al., "Affective video summarization and story board generation using Pupillary dilation and Eye gaze", 2011 IEEE International Symposium on Multimedia, 2011, Dana Point, CA, pp. 319-326.
Sourina, O., et al., "EEG-Based Personalized Digital Experience", International Conference on Universal Access in Human-Computer Interaction, 2011, pp. 591-599.
EP, 18861951.4 Extended Search Report, Aug. 9, 2021.
EP, 19736258.5 Supplementary Search Report, Oct. 26, 2021.
Extended European Search Report for Application No. European Patent Application No. 19736258.5, dated Oct. 26, 2021, (8 pages), European Patent Office, Munich, Germany.
Extended European Search Report for European Patent Application No. 18861951.4, dated Aug. 9, 2021, (11 pages), European Patent Office, Munich Germany.
Final Office Action for U.S. Appl. No. 16/923,033, dated Jan. 18, 2023, (18 pages), United States Patent and Trademark Office, US.
IPEA/409—International Preliminary Report on Patentability Mailed on Apr. 9, 2020 for WO Application No. PCT/US18/053218, 6 page(s).
IPEA/409—International Preliminary Report on Patentability Mailed on Apr. 9, 2020 for WO Application No. PCT/US18/053614, 7 page(s).
IPEA/409—International Preliminary Report on Patentability Mailed on Apr. 9, 2020 for WO Application No. PCT/US18/053625, 6 page(s).
IPEA/409—International Preliminary Report on Patentability Mailed on Jul. 23, 2020 for WO Application No. PCT/US19/012567, 6 page(s).
IPEA/409—International Preliminary Report on Patentability Mailed on Jul. 23, 2020 for WO Application No. PCT/US19/012783, 12 page(s).
Machine translation of published German patent application DE10242903A by Roland.

(56) References Cited

OTHER PUBLICATIONS

NonFinal Office Action for U.S. Appl. No. 16/923,033, dated Jun. 8, 2023, (15 pages), United States Patent and Trademark Office, US.
NonFinal Office Action for U.S. Appl. No. 16/923,033, dated Oct. 6, 2022, (13 pages), United States Patent and Trademark Office, US.
Outgoing—ISA/210—International Search Report and Written Opinion Mailed on Apr. 11, 2019 for WO Application No. PCT/US19/012567, 6 page(s).
Outgoing—ISA/210—International Search Report and Written Opinion Mailed on Apr. 25, 2019 for WO Application No. PCT/US19/012783, 13 page(s).
Outgoing—ISA/210—International Search Report and Written Opinion Mailed on Dec. 27, 2018 for WO Application No. PCT/US18/053625, 6 page(s).
Outgoing—ISA/210—International Search Report and Written Opinion Mailed on Jan. 17, 2019 for WO Application No. PCT/US18/053218, 6 page(s).
Outgoing—ISA/210—International Search Report and Written Opinion Mailed on Jan. 17, 2019 for WO Application No. PCT/US18/053614, 7 page(s).
Partial Supplementary Search Report for European Patent Application No. 19735809.6, dated Nov. 4, 2021, (17 pages), European Patent Office, Munich, Germany.
China National Intellectual Property Administration, First Office Action, Chinese Application No. 2019800167763, Nov. 6, 2023, 13 pages.
China National Intellectual Property Administration, First Office Action, Chinese Application No. 2019800176067, Jan. 22, 2024, 42 pages.
Medlin et al., Quantifying Sphingosine-1-Phosphate-Dependent Activation of the RhoGTPases, Methods Mol Biol., 2012, pp. 89-97, doi:10.1007/978-1-61779-800-9_8.

* cited by examiner

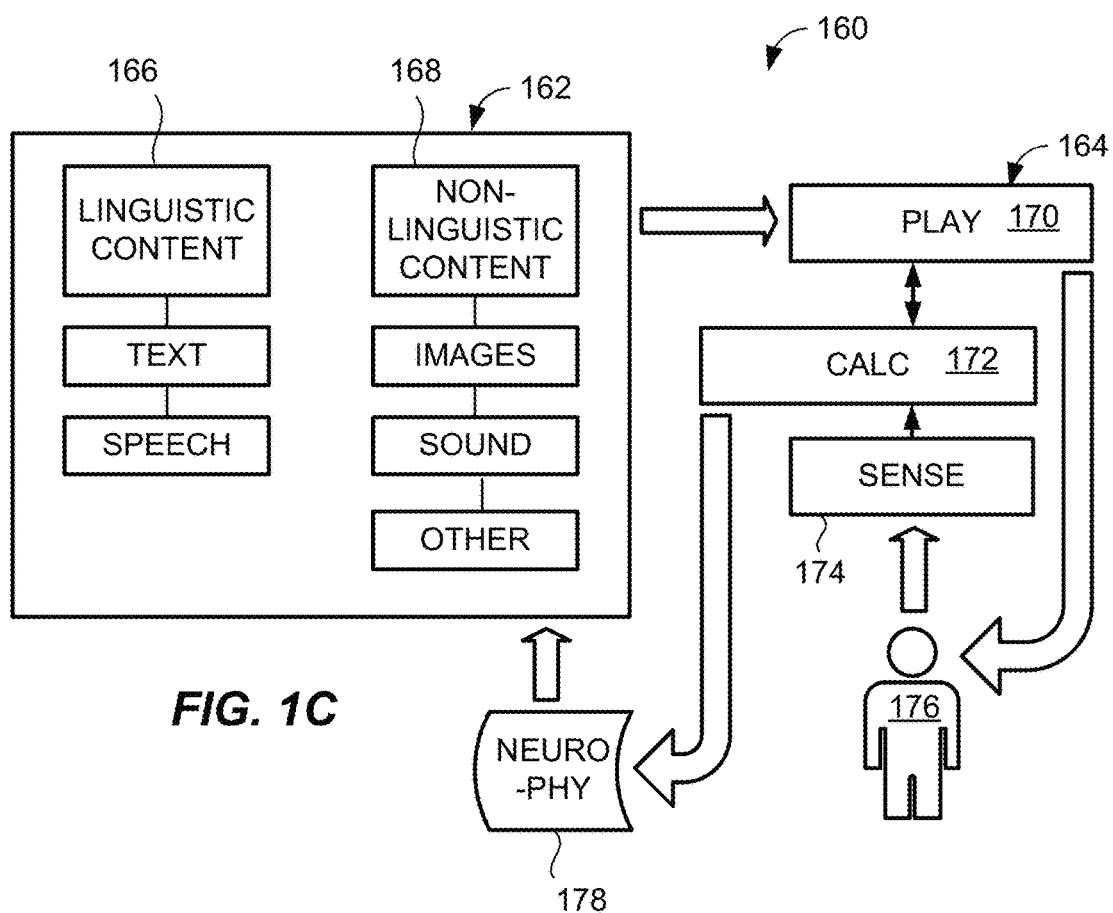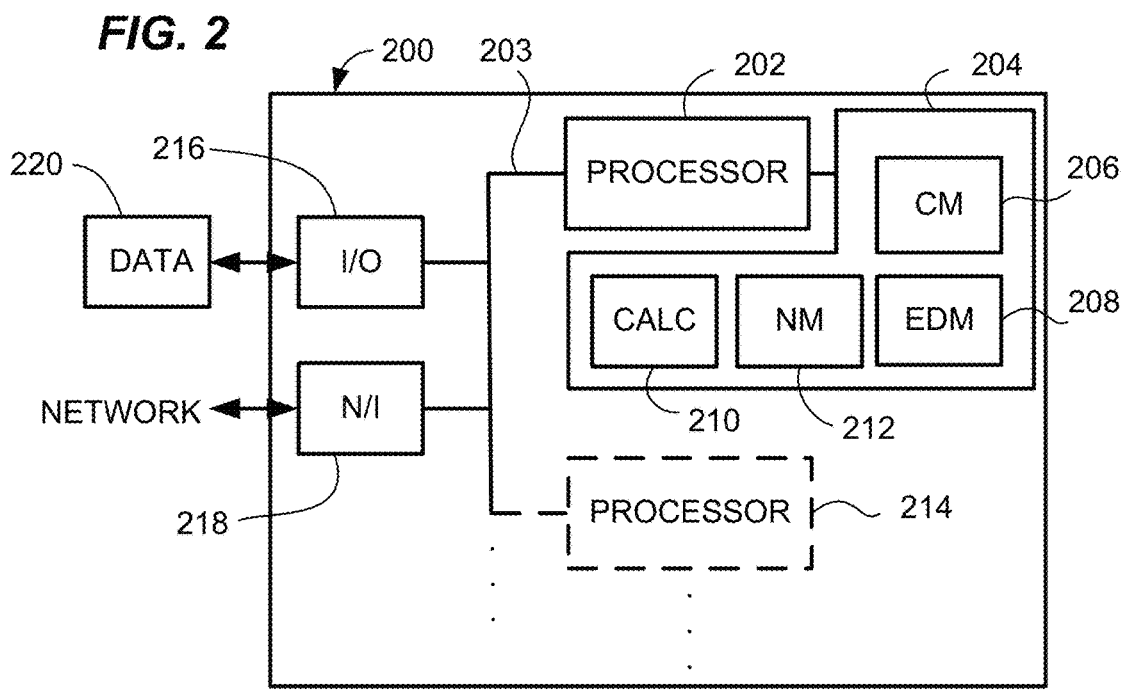

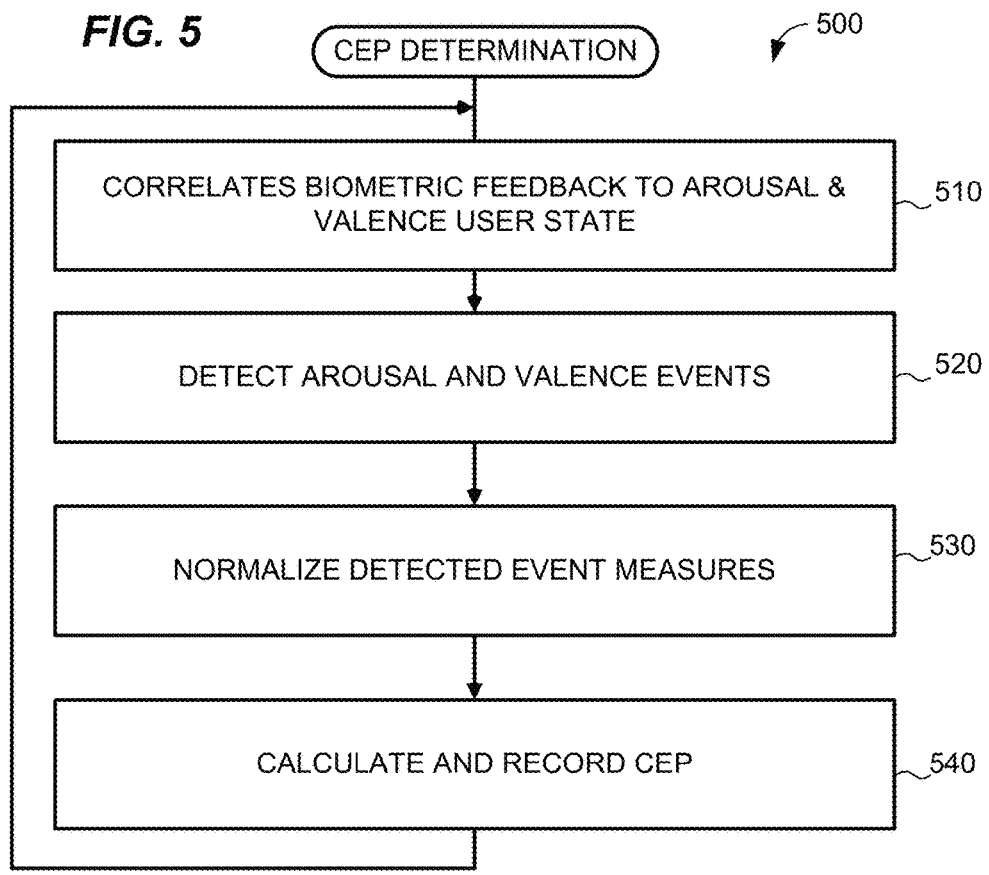
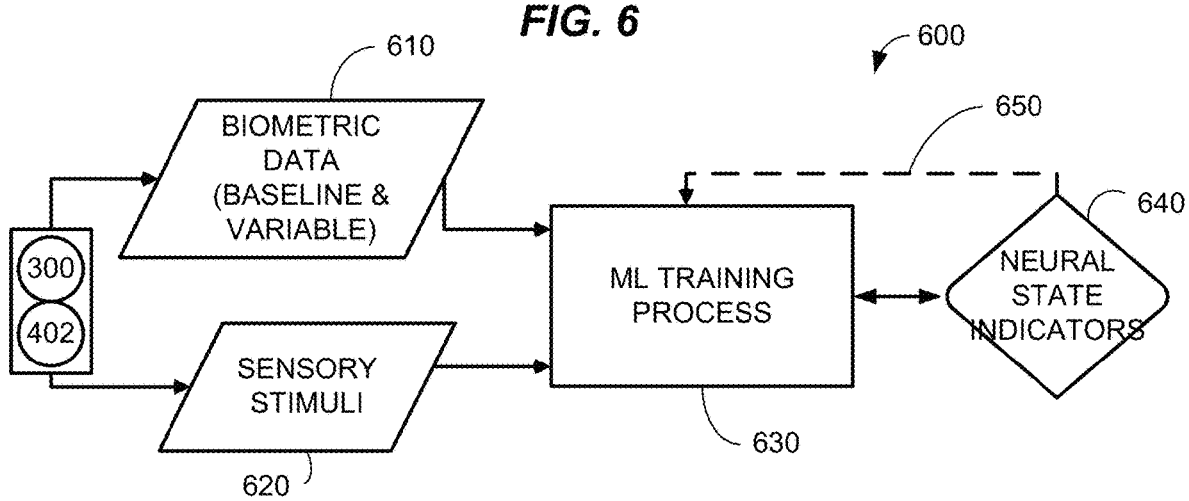

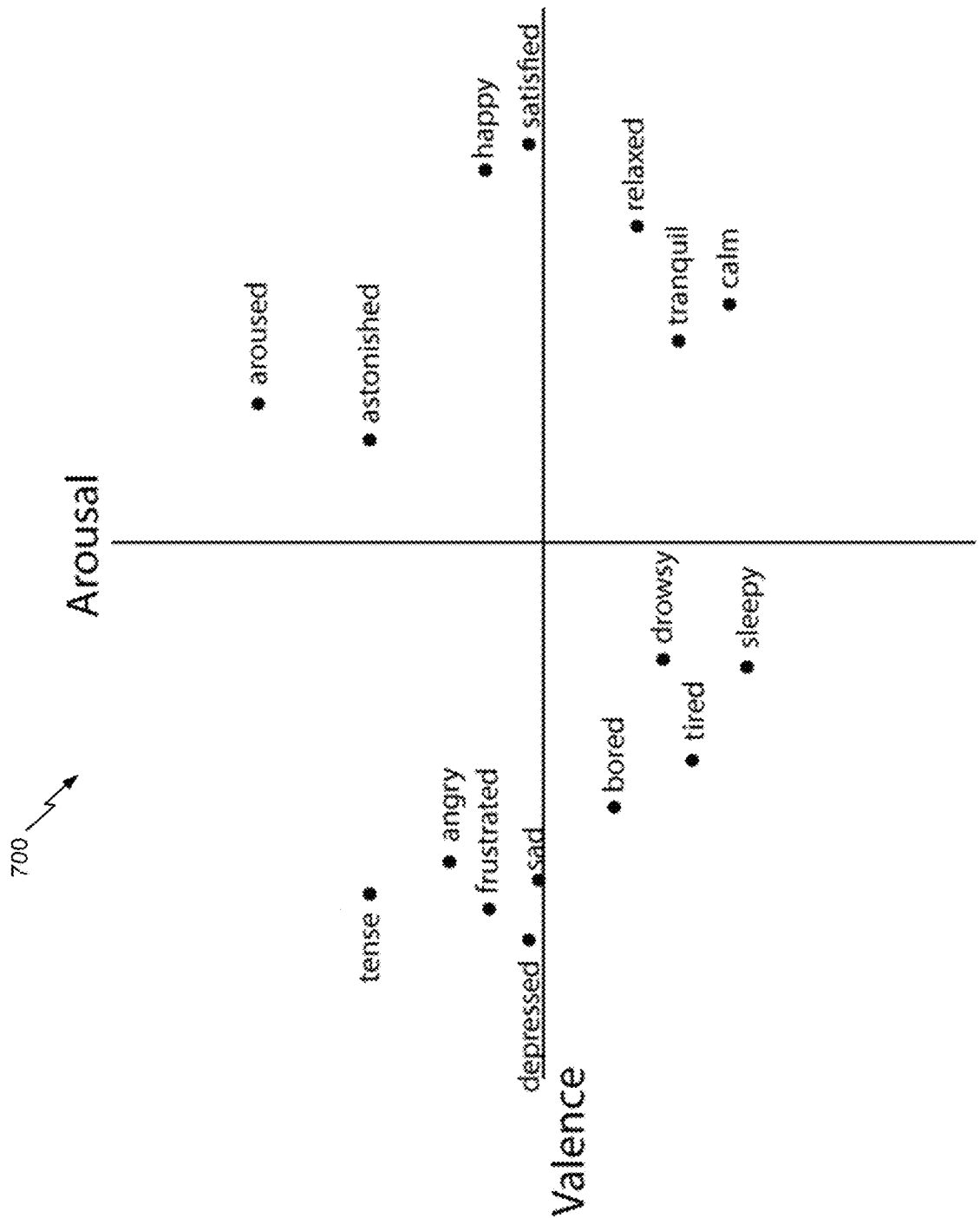

CONTENT GENERATION AND CONTROL USING SENSOR DATA FOR DETECTION OF NEUROLOGICAL STATE

CROSS-REFERENCE TO RELATED APPLICATION

The present application in a continuation of international (PCT) application No. US2019012783 filed Jan. 8, 2019, which claims priority to U.S. provisional patent application Serial Nos. 62/614,811 filed Jan. 8, 2018, 62/661,556 filed Apr. 23, 2018, and 62/715,766 filed Aug. 7, 2018, which applications are incorporated herein by reference in their entireties.

FIELD

The present disclosure relates to applications, methods and apparatus for signal processing of sensor data from detection of user neurological state in applications for generating or controlling linguistic content and other forms of communication content.

SUMMARY

This summary and the following detailed description should be interpreted as complementary parts of an integrated disclosure, which parts may include redundant subject matter and/or supplemental subject matter. An omission in either section does not indicate priority or relative importance of any element described in the integrated application. Differences between the sections may include supplemental disclosures of alternative embodiments, additional details, or alternative descriptions of identical embodiments using different terminology, as should be apparent from the respective disclosures. A previous application, Ser. No. 62/661,556 filed Apr. 23, 2018, lays a foundation for digitally representing user engagement with audio-video content, including but not limited to digital representation of Content Engagement Power (CEP) based on the sensor data. As described more fully in the earlier application, a computer process develops CEP for content based on sensor data from at least one sensor positioned to sense an involuntary response of one or more users while engaged with the audio-video output. For example, the sensor data may include one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (fMRI) data, body chemical sensing data and functional near-infrared data (fNIR) received from corresponding sensors. "User" means an audience member, a person experiencing communication content as a consumer for entertainment purposes. The present application builds on that foundation, making use of CEP in various applications summarized below.

CEP is an objective, algorithmic and digital electronic measure of a user's neuro-physiological state that correlates to engagement of the user with a stimulus, for example branched content. CEP expresses at least two orthogonal measures, for example, arousal and valence. As used herein, "arousal" means a state or condition of being physiologically alert, awake and attentive, in accordance with its meaning in psychology. High arousal indicates interest and attention, low arousal indicates boredom and disinterest. "Valence" is also used here in its psychological sense of attractiveness or goodness. Positive valence indicates attraction, and negative valence indicates aversion. As used herein, "neuro-physiological" means indicating or originating from a person's physiological state, neurological state, or both states. "Biometric" means a measure of a biological state, which encompasses "neuro-physiological" and may encompass other information, for example, identity information. Some data, for example, images of people's faces or other body portions, may indicate both identity and neuro-physiological state.

In an aspect of the disclosure, a CEP or similar measure is used in a method for generating a script. The method may include randomizing, by at least one processor, one or more parameters of a cognitive appraisal model for participants in character interactions. The method may further include generating a plurality of scripts by the at least one processor at least in part by modeling the character interactions while varying the parameters between different ones of the scripts. The method may further include, for each of the plurality of scripts, estimating a measure of effectiveness based on one of more targeted story arcs and on a cognitive appraisal model for neuro-physiological response. The method may include recording the measure of effectiveness in a computer memory.

In an aspect, estimating the measure of effectiveness may include calculating a Content Engagement Power (CEP) based on the cognitive appraisal model. Calculating the CEP value may further include determining arousal values and comparing a stimulation average arousal with an expectation average arousal. In addition, calculating the CEP value may further determining valence values. In a related aspect, estimating the measure of effectiveness may further include determining a neurological error measurement based on comparing predicted neuro-physiological responses to a targeted story arc. The targeted story arc may be, or may include, a set of targeted neurological values each uniquely associated with a different interval of a continuous time sequence.

In another aspect, a method for generating communication content, including linguistic content alone or in coordination with non-linguistic content, includes receiving, by at least one processor, neuro-physiological data from one or more sensors coupled to at least one user consuming segments of communication content, wherein the segments are selected from a library of alternative segments. The method may further include calculating, by the at least one processor for each of the segments a measure of the at least one user's neuro-physiological response based on the neuro-physiological data and on a cognitive appraisal model for assessing the neuro-physiological data. The method may further include recording, by the at least one processor, the measure of the at least one user's neuro-physiological response for each of the segments in a computer memory associated with an identifier for the each of the segments, for use in at least one of producing communication content including selected ones of the segments or selecting participants for a multi-participant communication session. The method may further include generating communication content, at least in part by selecting segments from the library based on each segment's associated measure of the at least one user's neuro-physiological response, and combining segments selected by the selecting. In an aspect, the processor may perform the collecting, the calculating, and the recording for multiple different users each consuming the segments.

In some applications, for example when the multi-participant communication session includes a computer game or a social chat session, the method may include matching users for the multi-participant communication session, at least in part by selecting ones of the multiple different users having complementary measures of neuro-physiological response for corresponding segments. In some cases, the segments consist essentially of linguistic content, for example written portions of text. In other cases, the segments consist essentially of audio content, including music. Thus, the method is useful for generating text documents and audio-only content, in addition to audio-video content.

The calculating may include determining a Content Engagement Power (CEP) value as described herein, or equivalent measure, for each of the segments. Determining the CEP value may include determining arousal values based on the neuro-physiological data and comparing a stimulation average arousal based on the neuro-physiological data with an expectation average arousal, and receiving the data from biometric sensors as described elsewhere herein. The method may further include determining valence values based on the neuro-physiological data, from the biometric sensors. The measure of the at least one user's neuro-physiological response for each of the segments may include at least one indication of valance. The selecting may further include assigning an error indicator to each segment's associated measure of the at least one user's neuro-physiological response, based on a difference between the associated measure and a target value, and minimizing segments having an assigned error indicator.

In another aspect, a method for controlling presentation of communication content, including linguistic content alone or in coordination with non-linguistic content includes receiving, by at least one processor, neuro-physiological data from one or more sensors coupled to at least one user while the user is consuming a segment of content on a client device, wherein the content comprises a chain of segments. The method further includes calculating, by the at least one processor for each of the segments a measure of the at least one user's neuro-physiological response based on the neuro-physiological data and on a cognitive appraisal model for assessing the neuro-physiological data. The method further includes selecting, by the at least one processor, a segment for later in the chain based on the measure of the at least one user's neuro-physiological response to the segment and outputting the later segment to the client device. The segments may include content linguistic content, audio content, or audio-video content.

The calculating may include determining a Content Engagement Power (CEP) value for the each of the segments as described elsewhere herein. Determining the CEP value may include determining arousal values based on the neuro-physiological data and comparing a stimulation average arousal based on the neuro-physiological data with an expectation average arousal, and/or determining valence values based on the neuro-physiological data. Sensors for indicating arousal and valence are described elsewhere herein. The method may include normalizing the valence or arousal values based on corresponding values collected for a set of designated baseline stimuli. The selecting may further include determining an error indicator for each segment's associated measure of the at least one user's neuro-physiological response, based on a difference between the associated measure and a target value, for example by minimizing segments having an assigned error indicator.

In another aspect, a method for collecting neuro-physiological data indicating a neuro-physiological response of a user consuming communication content may include detecting, by at least one processor of a mobile device, that a user of the mobile device is consuming communication content independently of the mobile device. The method may further include receiving, by the at least one processor, neuro-physiological data of the user via one or more sensors in the mobile device while the user is consuming the communication content. The method may further include providing at least one of the neuro-physiological data or an indicator of the user's neurological state derived therefrom to at least one of: a second device outputting the communication content, a remote server, or a computer memory.

The method may further include identifying, by the at least one processor, an identifier for the communication content and providing the identifier to at least one of the remote server or the computer memory. The method may include calculating, by the at least one processor, the indicator of the user's neurological state based on the neuro-physiological data and a cognitive appraisal model. The method may further include initiating a communication session with the second device outputting the communication content prior to the collecting. The collecting may be via at least one sensor of the mobile device comprising a microphone, a camera, an infrared sensor, a phased-array sensor, or a galvanic skin response sensor. In some embodiments, the mobile device may include, or be coupled to, a wrist-worn smart device. In some embodiments, the mobile device coordinates a handoff of a play session of the communication content from the second device to a third device. In an aspect, the mobile device does not communicate with the second device.

In an aspect of the method, the at least one processor of the mobile device may output a user-perceivable signal to attract at least one of a gaze, a touch, speech or a gesture at a time synchronized with play of the communication content. After outputting the user-perceivable signal, the at least one processor of the mobile device may receive at least a portion of the neuro-physiological data resulting from the gaze, the touch, the speech or the gesture.

In another application for a CEP or similar measure, a method for rating effectiveness of personal communications may include monitoring, by at least one processor, digital data representing a communication by a user to a recipient. The method may include receiving sensor data from at least one sensor positioned to sense an involuntary response of the recipient while receiving the communication. The method may include determining a Content Engagement Power (CEP) value, based on the sensor data and recording the CEP value in a computer memory and/or communicating a representation of the CEP value to the user. In an aspect, determining the CEP value may further include determining arousal values based on the sensor data and comparing a stimulation average arousal based on the sensor data with an expectation average arousal. The sensor data may include one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (fMRI) data, and functional near-infrared data (fNIR).

In a related aspect, the method may include determining the expectation average arousal based on further sensor data measuring a like involuntary response of the recipient while engaged with known audio-video stimuli. Accordingly, the method may include playing the known audio-video stimuli comprising a known non-arousing stimulus and a known arousing stimulus. More detailed aspects of determining the CEP value, calculating one of multiple event powers for each of the one or more users, assigning weights to each of the event powers based on one or more source identities for the sensor data, determining the expectation average arousal and determining valence values based on the sensor data may be as described for other application, herein above or in the more detailed description below.

The foregoing methods may be implemented in any suitable programmable computing apparatus, by provided program instructions in a non-transitory computer-readable medium that, when executed by a computer processor, cause the apparatus to perform the described operations. The processor may be local to the apparatus and user, located remotely, or may include a combination of local and remote processors. An apparatus may include a computer or set of connected computers that is used in measuring and communicating CEP or like engagement measures for content output devices. A content output device may include, for example, a personal computer, mobile phone, notepad computer, a television or computer monitor, a projector, a virtual reality device, or augmented reality device. Other elements of the apparatus may include, for example, an audio output device and a user input device, which participate in the execution of the method. An apparatus may include a virtual or augmented reality device, such as a headset or other display that reacts to movements of a user's head and other body parts. The apparatus may include neuro-physiological sensors that provide data used by a controller to determine a digital representation of CEP.

To the accomplishment of the foregoing and related ends, one or more examples comprise the features hereinafter fully described and particularly pointed out in the claims. The following description and the annexed drawings set forth in detail certain illustrative aspects and are indicative of but a few of the various ways in which the principles of the examples may be employed. Other advantages and novel features will become apparent from the following detailed description when considered in conjunction with the drawings and the disclosed examples, which encompass all such aspects and their equivalents.

BACKGROUND

Linguistic content including both written text and speech is central to human communication. People have developed many tools to assist in its dissemination. Until the computer age, only humans could participate in the generation of linguistic content. Since then, talking computers have become commonplace. Computers are used to generate all types of linguistic content, in both written and verbal forms. Computer-generated linguistic content is functional but lacks the power to excite the imagination and engage the listener like great literature and speeches can.

Much linguistic content has commercial importance. For example, linguistic content is critical to the entertainment industry, for textual content such as books, audio books, dialog for dramatic performances, scripts, and other uses. Without compelling linguistic content, entertainment is flat and non-engaging. Consumers won't pay for it or consume it at all if they have better options. Advertisers won't sponsor it. Although computers are used in the generation of linguistic content for technical tasks like word processing, the job of making linguistic content more engaging has remained out of necessity in human hands. The logic that drives functional responses is not well-suited for generating engaging content.

Linguistic content is often accompanied by non-linguistic content such as music, graphic arts, and video. Commercial entertainers work to integrate linguistic and non-linguistic content in more compelling ways, to attract the greatest possible audiences. Generation and control of linguistic and non-linguistic content are often interrelated. As used herein, "communication content" includes linguistic content and other entertainment or aesthetic content that is sequenced for presentation or consumption through time. Whether communication content is purely linguistic or includes other elements, computers are poorly equipped to generate or control content so that it is more compelling to audiences. Even if machines can never fully replace human artists, artists and audiences will benefit by providing artists with more capable tools for producing and controlling content. "Communication content" is sometimes referred to herein as "content."

It would be desirable, therefore, to develop new methods and other new technologies for generating and controlling linguistic content alone or in coordination with non-linguistic content, that overcome these and other limitations of the prior art and help producers deliver more compelling entertainment experiences for the audiences of tomorrow.s

BRIEF DESCRIPTION OF THE DRAWINGS

The features, nature, and advantages of the present disclosure will become more apparent from the detailed description set forth below when taken in conjunction with the drawings in which like reference characters identify like elements correspondingly throughout the specification and drawings.

FIGS. 1B-C are diagrams illustrating aspects of communication content.

FIG. 2 is a schematic block diagram illustrating aspects of a server for generating a script, text, or other communication content, for controlling playout of communication content based on neuro-physiological data, or rating effectiveness of personal communications.

FIG. 5 is a flow chart illustrating high-level operation of a method determining a digital representation of CEP based on sensor data collected during performance of communication content.

FIG. 6 is a block diagram illustrating high-level aspects of a system for training a machine learning process to determine a digital representation of CEP based on sensor data collected during performance of communication content.

FIG. 7A is a diagram indicating an arrangement of neurological states relative to axes of a two-dimensional neuro-physiological space of a cognitive appraisal model.

DETAILED DESCRIPTION

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form to facilitate describing these aspects.

Figure 1A:
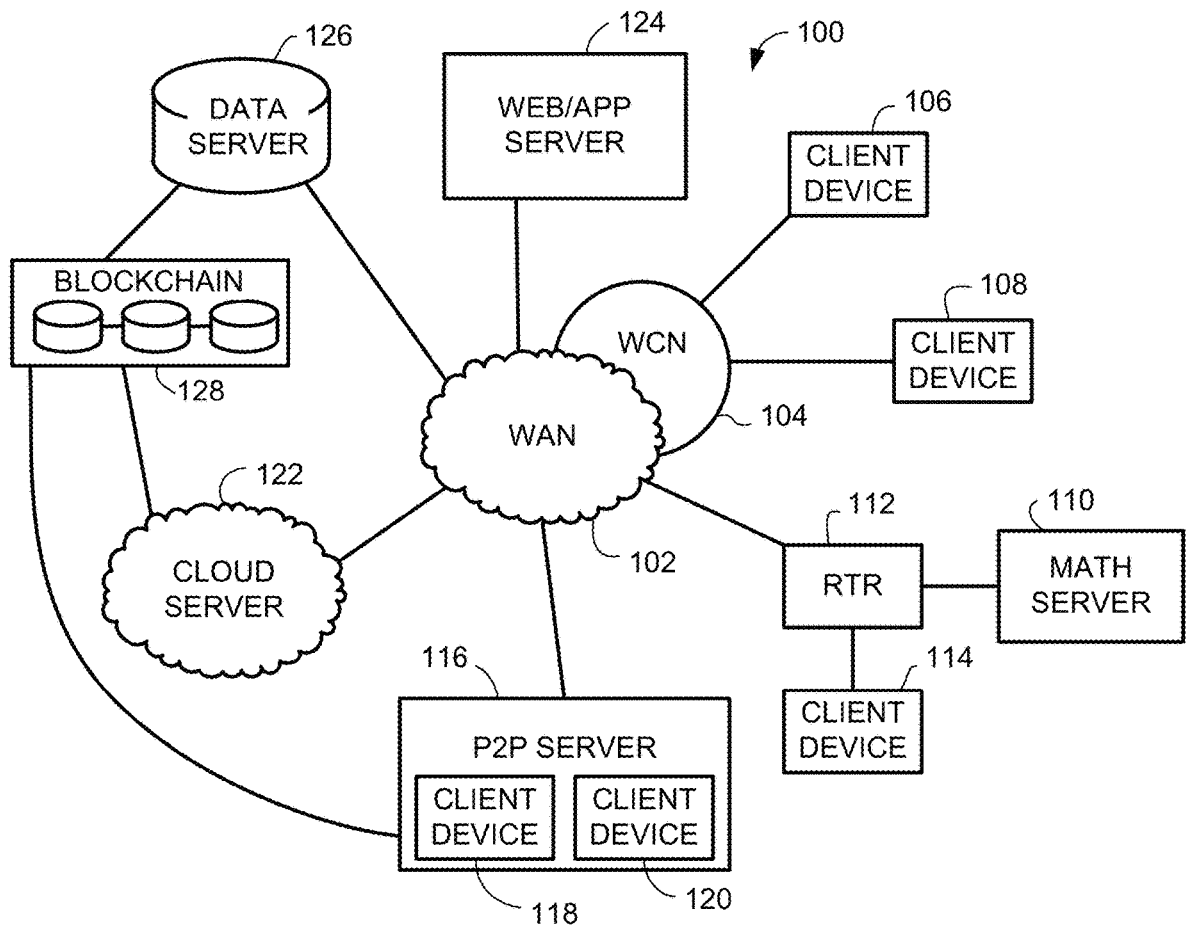
FIG. 1A is a schematic block diagram illustrating aspects of a system and apparatus for generating a script, text, or other communication content or for controlling playout of communication content based on neuro-physiological data, gathering neuro-physiological data correlated to consumption of communication content, or rating effectiveness of personal communications, coupled to one or more distribution systems.

Referring to FIG. 1A, methods for signal processing of neuro-physiological sensor data for detection of neurological state in communication enhancement applications may be implemented in a client-server environment 100. Other architectures may also be suitable. In a network architecture, sensor data can be collected and processed locally, and transmitted to a server that processes neuro-physiological sensor data from one or more subjects, calculating a digital representation of user neurological state based on the sensor data and using in a computer memory to control a machine. Communication enhancement contexts for the present technology include generating a script, text, or other communication content or for controlling playout of communication content based on neuro-physiological data, gathering neuro-physiological data correlated to consumption of communication content, or rating effectiveness of personal communications.

Recorded communications may be branched or unbranched. "Branched" means the communication content includes alternative segments that can be combined variously based on assessment of neuro-physiological data using a cognitive appraisal model. A control processor selects which of alternative segments it will include at run time. If branched content has an unbranched narrative, it will include branching of other dramatic elements. Although the content may be branched, it may have a coherent theme, dramatic purpose and story arc that encompasses all its branches. "Unbranched" means the communication content has no alternative segments, for example in conversation or in fixed productions. In a production environment, a director may choose one of alternative takes or scenes based on assessment of neuro-physiological data using a cognitive appraisal model from a focus group, but these pre-release alternatives are not used in general distribution.

A data processing server such as "math" server 110 may receive sensor data from sensors positioned to detect neuro-physiological responses of users during consumption of communication content. Sensors may be coupled to the network via any of the client devices 106, 108, 114, 120, 118, which may be in use for consuming communication content or merely in proximity to a user who is consuming content output by a different device. The server 100 may process the sensor data to obtain a digital representation indicative of the audience's neuro-physiological (e.g., emotional) response to the communication content, as a function of time or video frame, indicated along one or more measurement axes (e.g., arousal and valence). In alternative embodiments, content-adaptive AI may adapt the content to increase or maintain engagement by user, based on real-time biosensor feedback.

A suitable client-server environment 100 may include various computer servers and client entities in communication via one or more networks, for example a Wide Area Network (WAN) 102 (e.g., the Internet) and/or a wireless communication network (WCN) 104, for example a cellular telephone network for data communications, e.g., LTE, 4G, 5G. Computer servers may be implemented in various architectures. For example, the environment 100 may include one or more Web/application servers 124 containing documents and application code compatible with World Wide Web protocols, including but not limited to HTML, XML, PHP and Javascript documents or executable scripts, for example. The Web/application servers 124 may serve applications for outputting communication content and for collecting biometric sensor data from users experiencing the content. In an alternative, data collection applications may be served from a math server 110, cloud server 122, blockchain entity 128, or content data server 126. Users may consume communication content using any client device or terminal as described herein; in some embodiments, users may consume the content from an independent source such as a cinema projector, home movie theater or television, or radio.

The environment 100 may include one or more data servers 126 for holding communication content, for example linguistic content, alone or in combination with video, audio-video, audio, and graphical content components of communication content for consumption using a client device, software for execution on or in conjunction with client devices, for example sensor control and sensor signal processing applications, and data collected from users or client devices. Data collected from client devices or users may include, for example, biometric sensor data and application data. Sensor data may be collected by a background (not user-facing) application operating on the client device, and transmitted to a data sink, for example, a cloud-based data server 122 or discrete data server 126. Application data means application state data, including but not limited to records of user interactions with an application or other application inputs, outputs or internal states. Applications may include software for outputting communication content, collecting and processing biometric sensor data, calculating measures or indicators of a user's neuro-physiological response, providing the indicators or measures to designated outputs, selecting segments of content based on the indicators or measures, and supporting functions. Applications and data may be served from other types of servers, for example, any server accessing a distributed blockchain data structure 128, or a peer-to-peer (P2P) server 116 such as may be provided by a set of client devices 118, 120 operating contemporaneously as micro-servers or clients.

As used herein, "users" are always consumers of communication content from which a system node collects neuro-physiological response data for use in determining a digital representation of engagement with communication content. When actively participating in content via an avatar or other agency, users may also be referred to herein as player-actors. Viewers are not always users. For example, a bystander may be a passive viewer from which the system collects no biometric response data. As used herein, a "node" includes a client or server participating in a computer network.

The network environment 100 may include various client devices, for example a mobile smart phone client 106 and notepad client 108 connecting to servers via the WCN 104 and WAN 102 or a mixed reality (e.g., virtual reality or augmented reality) client device 114 connecting to servers via a router 112 and the WAN 102. In general, client devices may be, or may include, computers used by users to access communication content provided via a server or from local storage. Clients may also include biometric sensors that provide neuro-physiological data to the apparatus and processes as described herein. In an aspect, the data processing server 110 may determine digital representations of biometric data for use in real-time or offline applications. Controlling branching or the activity of objects in narrative content is an example of a real-time application, for example as described in U.S. provisional patent application Ser. No. 62/566,257 filed Sep. 29, 2017 and Ser. No. 62/614,811 filed Jan. 8, 2018, incorporated by reference herein.

Offline applications may include, for example, "green lighting" production proposals, automated screening of production proposals prior to green lighting, automated or semi-automated packaging of promotional content such as trailers or video ads, and customized editing or design of content for targeted users or user cohorts (both automated and semi-automated). In greenlighting screenplays or stories, a client device may receive neuro-physiological data while a user is reading a script or other text on a tablet device, using biometric sensors as described herein. The client or a server may record a CEP score or equivalent measure in reference to calibration data from this quantitative emotional data. Creative produces may then choose or refine screenplays, proposals, scripts and so forth considering summation of CEP event powers, agreement with emotional arcs or discovery of new better performing emotional arcs. The neuro-physiological data may also be used in tools for writers, enabling writers to plan conditional text based on biometric emotional feedbacks and arcs for tested story elements.

In some embodiments, a client device is both providing the communication content and sensing biometric data. A client device may use neuro-physiological data locally or may pass the data to a cloud server for use in other communication content sessions, for example, in over-the-top (OTT) experiences in the car or on a home TV. In an OTT experience, a server hands off a content session across platforms in real time, using high bandwidth networks (5G). A content session can start on mobile device, and move across different platforms such as virtual reality, home theater or in-vehicle entertainment system. In other embodiments, a different device provides the communication content while the client device functions and a sensor and handler of neuro-physiological data. A client device such as a smart phone or smart watch may collect neuro-physiological and other biometric data using a front-facing stereo camera for tracking gaze direction, pupil dilation, and/or facial action units; a microphone for audio speech analysis and/or neuro-linguistic programming word analysis; a phased array sensor (if present) for tracking gaze direction, pupil dilation, and/or facial action units, an infrared sensor for functional near-infrared sensing of skin temperature. In addition, the client device may connection to an ancillary device using Bluetooth or other protocol to obtain sensor data. For example, a smart phone may connect to a smart watch or fitness band worn around the wrist or head to obtain pulse rate, skin temperature, galvanic skin response, or electroencephalogram (EEG) data for calculation of a neuro-physiological measure as described herein.

Figure 1B:
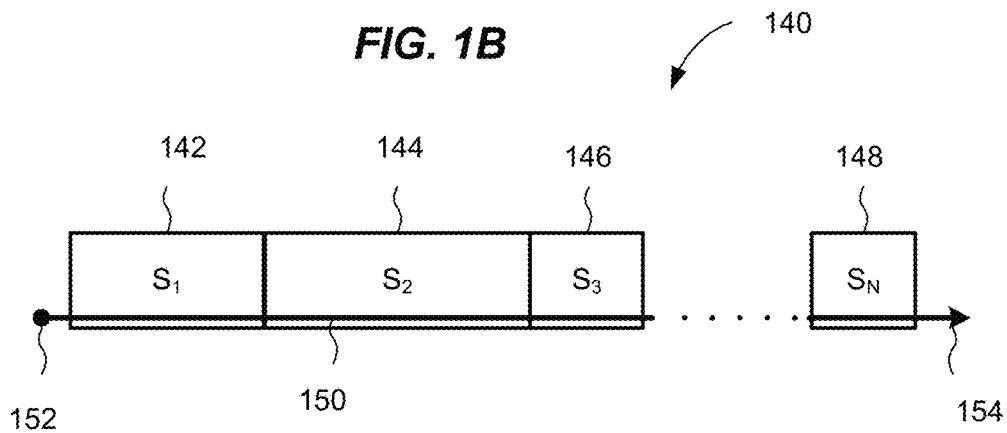

FIG. 1B diagrams aspects of communication content 140. Some finite 'N' number of segments ($S_N$) 142, 144, 146, 148 may be video frames, textual or linguistic components, musical phrases (e.g. bars), panels of a graphic novel, or any other signal or subject matter for arrangement along a time-like dimension having a direction of flow. Content of the segment may be predetermined (e.g., movie, video) or determined on the fly (e.g., computer game or talk show), and may be digitized in computer-readable form. The collection of all segments $S_1$ 142 to $S_N$ 148 makes up the "communication content," which as used herein means machine-readable content made up of segments for arrangement along a time-like dimension 150 having a direction of flow from a beginning 152 to an end 154; the exact time of the end may be unknown or indefinite at earlier times during the communication content. A discrete collection of segments makes up a content "title," "experience," or "work." Examples of communication content and application of the methods herein to different forms of communication content are summarized below.

Referring to FIG. 1C, a system 160 for use with methods and apparatus described herein may include communication content 162, a computational module 164, a user 176 and neuro-physiological data 178. Communication content 162 may include linguistic content 166 including text or speech, for example, scripts, screenplays, books, graphic novels and comic books, and other printed content for reading, audio content such as audio books or podcasts, and may be included in other content for example video, virtual reality, or video game content that includes speech or text. Although arranged on a page, most text is arranged to be read left to right, right to left, and/or top to bottom in a sequence along a time-like dimension 150 having a direction of flow from a beginning 152 to an end 154. Thus, written materials (text) produced in electric form generally fall within the definition of communication content 162 as used herein. Biometric feedback and measures of neuro-physiological response 178 may be used in production control of written materials, or in controlling presentation of written material. In presentation control, one or more processors of a computational module 164 changes the text segments that are selected and displayed to a user, based on neuro-physiological feedback via biometric sensors.

The computational module 164 includes at least three components, a player 170 that decodes communication content and presents it to a user 176, a control or calculation component 172 that receives data from one or more biometric sensors of a sensing component 174 and calculates one or more neuro-physiological measures 178 from the sensor data, and a sensing component 174 that responds to neuro-physiological changes in the user 176 and generates a digital signal for processing. The calculation component 172, sensing component 174 and player component 170 may be consolidated in one device or divided between two or more devices.

Communication content 164 may include non-linguistic content 168, for example, music and other audio content, images, and data for other perceptual output for example tactile, olfactory or kinetic output. Non-linguistic content may be combined with linguistic content, for example music may be with or without lyrics, and most video includes a linguistic element. A processor may score segments of audio content, for example, by receiving and analyzing neuro-physiological data from biometric sensors while user is listening to music on a client device. The processor may select audio based on summation of CEP event powers, agreement with emotional arcs or discovery of new better performing emotional arcs. In general, the processor may use neuro-physiological data in a passive mode (data collection only) or active mode (content changes based on biofeedback). Neuro-physiological data may also be used to avoid personal or cultural triggers for anger, fear, or other undesired reactions by historical data for individuals or cohorts. A processor executing a machine learning algorithm may learn to "anticipate" triggers based on historical data.

In addition to providing neuro-physiological data, biometric sensors can also be used for personal identification, using recognition of faces and other unique biological features of users. Thus, an apparatus may use the same sensors for identification and for receiving neuro-physiological data to use in content analysis, generation, or control. In an aspect, when collecting baseline data the communication content may be selected for compatibility with available sensor modalities. For example, if eye tracking (also called gaze detection) is not available, characters or items of interest may be portrayed alone instead of with other characters. With eye tracking, characters can be displayed together because the eye tracking will indicate which character is attracting the user's interest or causing the user to avert their eyes.

In other applications, a processor may use personal patterns of neuro-physiological responses to known content as a basis for matching people as prospective friends or coplayers. A processor can use the personal patterns to help users explore new content (random generation) or find content like that a user has preferred in the past. The processor may sometime make sub-optimal selections to compensate for users in high demand.

FIG. 2 shows a data processing server 200 for generating a script, text, or other communication content in a computer memory based on biometric sensor data, which may operate in the environment 100, in similar networks, or as an independent server. The server 200 may include one or more hardware processors 202, 214 (two of one or more shown). Hardware includes firmware. Each of the one or more processors 202, 214 may be coupled to an input/output port 216 (for example, a Universal Serial Bus port or other serial or parallel port) to a source 220 for biometric sensor data indicative of users' neurological states and viewing history. Viewing history may include a log-level record of variances from a baseline script for a content package or equivalent record of control decisions made in response to user biometric and other input. Viewing history may also include content viewed on TV, Netflix and other sources. Any source that contains a derived story arc may be useful for input to an algorithm for generating a script, text, or other an actor, character or other story element in a computer memory based on biometric sensor data. The server 200 may track user actions and biometric responses across multiple content titles for individuals or cohorts. Some types of servers, e.g., cloud servers, server farms, or P2P servers, may include multiple instances of discrete servers 200 that cooperate to perform functions of a single server.

The server 200 may include a network interface 218 for sending and receiving applications and data, including but not limited to sensor and application data used for generating a script, text, or other communication content in a computer memory based on biometric sensor data. The content may be served from the server 200 to a client device or stored locally by the client device. If stored local to the client device, the client and server 200 may cooperate to handle collection of sensor data and transmission to the server 200 for processing.

Each processor 202, 214 of the server 200 may be operatively coupled to at least one memory 204 holding functional modules 206, 208, 210, 212 of an application or applications for performing a method as described herein. The modules may include, for example, a correlation module 206 that correlates biometric feedback to one or more metrics such as arousal or valence. The correlation module 206 may include instructions that when executed by the processor 202 and/or 214 cause the server to correlate biometric sensor data to one or more neurological (e.g., emotional) states of the user, using machine learning (ML) or other processes. An event detection module 208 may include functions for detecting events based on a measure or indicator of one or more biometric sensor inputs exceeding a data threshold. The modules may further include, for example, a normalization module 210. The normalization module 210 may include instructions that when executed by the processor 202 and/or 214 cause the server to normalize measures of valence, arousal, or other values using a baseline input. The modules may further include a calculation function 212 that when executed by the processor causes the server to calculate a Content Engagement Power (CEP) based on the sensor data and other output from upstream modules. Details of determining a CEP are disclosed later herein. The memory 204 may contain additional instructions, for example an operating system, and supporting modules.

Figure 3:
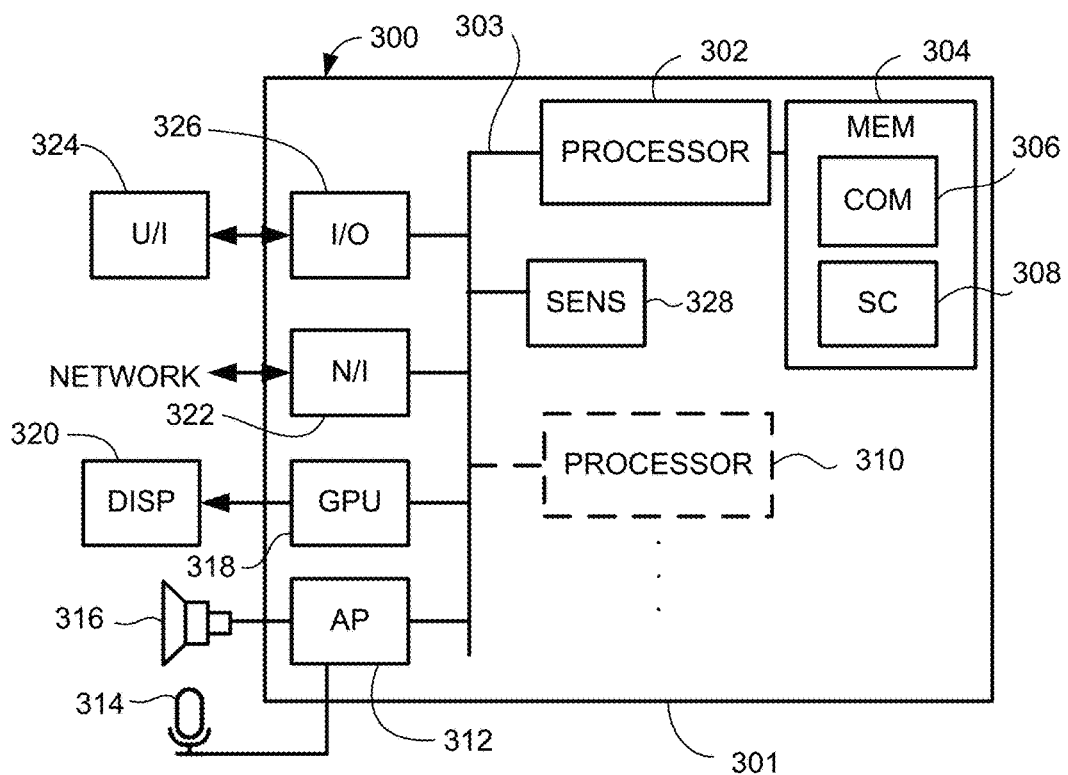
FIG. 3 is a schematic block diagram illustrating aspects of a client device for generating a script, text, or other communication content or for controlling playout of communication content based on neuro-physiological data, gathering neuro-physiological data correlated to consumption of communication content, or rating effectiveness of personal communications, coupled to one or more distribution systems.

Referring to FIG. 3, a content consumption device 300 generates biometric sensor data indicative of a user's neurophysiological response to output generated from a communication content signal. The apparatus 300 may include, for example, a processor 302, for example a central processing unit based on 80×86 architecture as designed by Intel™ or AMD™, a system-on-a-chip as designed by ARM™, or any other suitable microprocessor. The processor 302 may be communicatively coupled to auxiliary devices or modules of the 3D environment apparatus 300, using a bus or other coupling. Optionally, the processor 302 and its coupled auxiliary devices or modules may be housed within or coupled to a housing 301, for example, a housing having a form factor of a television, set-top box, smartphone, wearable googles, glasses, or visor, or other form factor.

A user interface device 324 may be coupled to the processor 302 for providing user control input to a media player and data collection process. The process may include outputting video and audio for a display screen or projection display device. In some embodiments, the communication content control process may be, or may include, audio-video output for an immersive mixed reality content display process operated by a mixed reality immersive display engine executing on the processor 302.

User control input may include, for example, selections from a graphical user interface or other input (e.g., textual or directional commands) generated via a touch screen, keyboard, pointing device (e.g., game controller), microphone, motion sensor, camera, or some combination of these or other input devices represented by block 324. Such user interface device 324 may be coupled to the processor 302 via an input/output port 326, for example, a Universal Serial Bus (USB) or equivalent port. Control input may also be provided via a sensor 328 coupled to the processor 302. A sensor 328 may be or may include, for example, a motion sensor (e.g., an accelerometer), a position sensor, a camera or camera array (e.g., stereoscopic array), a biometric temperature or pulse sensor, a touch (pressure) sensor, an altimeter, a location sensor (for example, a Global Positioning System (GPS) receiver and controller), a proximity sensor, a motion sensor, a smoke or vapor detector, a gyroscopic position sensor, a radio receiver, a multi-camera tracking sensor/controller, an eye-tracking sensor, a microphone or a microphone array, an electroencephalographic (EEG) sensor, a galvanic skin response (GSR) sensor, a facial electromyography (fEMG) sensor, an electrocardiogram (EKG) sensor, a video facial action unit (FAU) sensor, a brain machine interface (BMI) sensor, a video pulse detection (VPD) sensor, a pupil dilation sensor, a body chemical sensor, a functional magnetic resonance imaging (fMRI) sensor, a photoplethysmography (PPG) sensor, phased-array radar (PAR) sensor, or a functional near-infrared data (fNIR) sensor. Any one or more of an eye-tracking sensor, FAU sensor, PAR sensor, pupil dilation sensor or heartrate sensor may be or may include, for example, a front-facing (or rear-facing) stereoscopic camera such as used in the iPhone 10 and other smartphones for facial recognition. Likewise, cameras in a smartphone or similar device may be used for ambient light detection, for example, to detect ambient light changes for correlating to changes in pupil dilation.

The sensor or sensors 328 may detect biometric data used as an indicator of the user's neurological state, for example, one or more of facial expression, skin temperature, pupil dilation, respiration rate, muscle tension, nervous system activity, pulse, EEG data, GSR data, fEMG data, EKG data, FAU data, BMI data, pupil dilation data, chemical detection (e.g., oxytocin) data, fMRI data, PPG data or fNIR data. In addition, the sensor(s) 328 may detect a user's context, for example an identity position, size, orientation and movement of the user's physical environment and of objects in the environment, motion or other state of a user interface display, for example, motion of a virtual-reality headset. Sensors may be built into wearable gear or may be non-wearable, including a display device, or in auxiliary equipment such as a smart phone, smart watch, or implanted medical monitoring device. Sensors may also be placed in nearby devices such as, for example, an Internet-connected microphone and/or camera array device used for hands-free network access or in an array over a physical set.

Sensor data from the one or more sensors 328 may be processed locally by the CPU 302 to control display output, and/or transmitted to a server 200 for processing by the server in real time, or for non-real-time processing. As used herein, "real time" refers to processing responsive to user input without any arbitrary delay between inputs and outputs; that is, that reacts as soon as technically feasible. "Non-real time" or "offline" refers to batch processing or other use of sensor data that is not used to provide immediate control input for controlling the display, but that may control the display after some arbitrary amount of delay.

To enable communication with another node of a computer network, for example the communication content server 200, the client 300 may include a network interface 322, e.g., an Ethernet port, wired or wireless. Network communication may be used, for example, to enable multi-player experiences, including immersive or non-immersive experiences of communication content. The system may also be used for non-directed multi-user applications, for example social networking, group entertainment experiences, instructional environments, video gaming, and so forth. Network communication can also be used for data transfer between the client and other nodes of the network, for purposes including data processing, content delivery, content control, and tracking. The client may manage communications with other network nodes using a communications module 306 that handles application-level communication needs and lower-level communications protocols, preferably without requiring user management.

A display 320 may be coupled to the processor 302, for example via a graphics processing unit 318 integrated in the processor 302 or in a separate chip. The display 320 may include, for example, a flat screen color liquid crystal (LCD) display illuminated by light-emitting diodes (LEDs) or other lamps, a projector driven by an LCD display or by a digital light processing (DLP) unit, a laser projector, or other digital display device. The display device 320 may be incorporated into a virtual reality headset or other immersive display system, or may be a computer monitor, home theater or television screen, or projector in a screening room or theater. In a real live theater application, clients for users and actors may avoid using a display in a favor or audible input through an earpiece or the live, or tactile impressions through a tactile suit.

Video output driven by a mixed reality display engine operating on the processor 302, or other application for coordinating user inputs with an immersive content display and/or generating the display, may be provided to the display device 320 and output as a video display to the user. Similarly, an amplifier/speaker or other audio output transducer 316 may be coupled to the processor 302 via an audio processor 312. Audio output correlated to the video output and generated by the media player module 308, communication content control engine or other application may be provided to the audio transducer 316 and output as audible sound to the user. The audio processor 312 may receive an analog audio signal from a microphone 314 and convert it to a digital signal for processing by the processor 302. The microphone can be used as a sensor for detection of neurological (e.g., emotional) state and as a device for user input of verbal commands, or for social verbal responses to non-player characters or other player-actors.

The 3D environment apparatus 300 may further include a random-access memory (RAM) 304 holding program instructions and data for rapid execution or processing by the processor during controlling communication content in response to biosensor data collected from a user. When the device 300 is powered off or in an inactive state, program instructions and data may be stored in a long-term memory, for example, a non-volatile magnetic, optical, or electronic memory storage device (not shown). Either or both RAM 304 or the storage device may comprise a non-transitory computer-readable medium holding program instructions, that when executed by the processor 302, cause the device 300 to perform a method or operations as described herein. Program instructions may be written in any suitable high-level language, for example, C, C++, C#, JavaScript, PHP, or Java™, and compiled to produce machine-language code for execution by the processor.

Program instructions may be grouped into functional modules 306, 308, to facilitate coding efficiency and comprehensibility. A communication module 306 may include coordinating communication of biometric sensor data if metadata to a calculation server. A sensor control module 308 may include controlling sensor operation and processing raw sensor data for transmission to a calculation server. The modules 306, 308, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. The modules may be high-level modules only. The media player module 308 may perform operations of any method described herein, and equivalent methods, in whole or in part. Operations may be performed independently or in cooperation with another network node or nodes, for example, the server 200.

Figure 4:
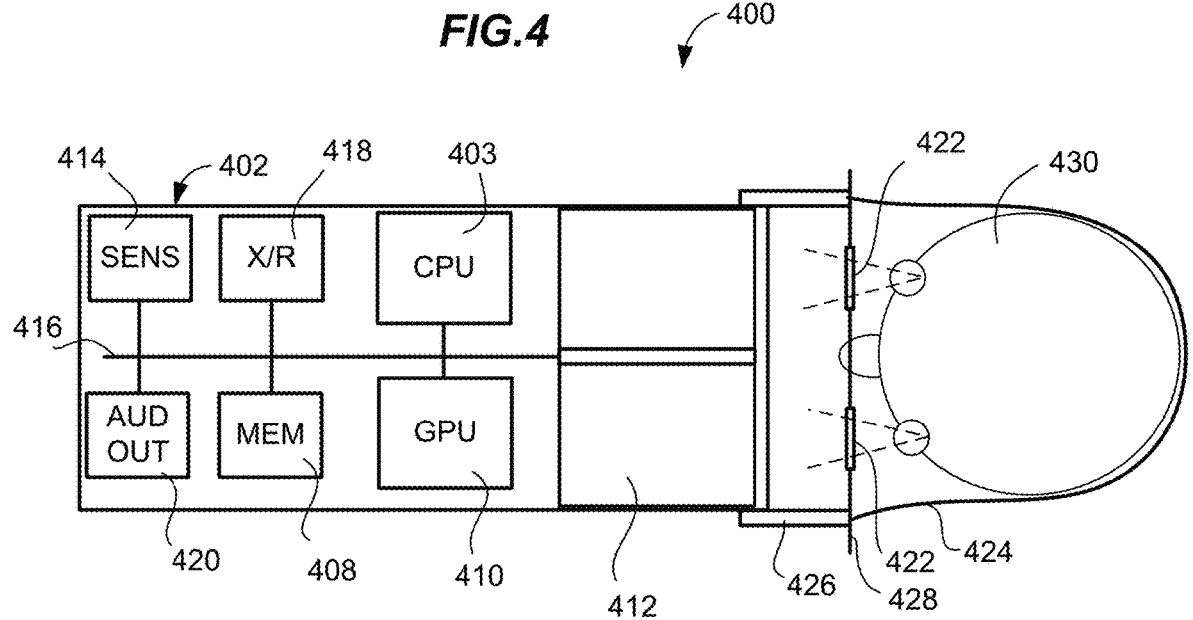
FIG. 4 is a schematic diagram showing features of a virtual-reality client device for generating a script, text, or other communication content or for controlling playout of communication content based on neuro-physiological data, gathering neuro-physiological data correlated to consumption of communication content, or rating effectiveness of personal communications, coupled to one or more distribution systems.

The content control methods disclosed herein may be used with Virtual Reality (VR) or Augmented Reality (AR) output devices, for example in virtual chat, immersive content or non-immersive content. FIG. 4 is a schematic diagram illustrating one type of immersive VR stereoscopic display device 400, as an example of the client 300 in a more specific form factor. The client device 300 may be provided in various form factors, of which device 400 provides but one example. The innovative methods, apparatus and systems described herein are not limited to a single form factor. As used herein, "communication content signal" includes any digital signal for output of communication content, which may be interactive or non-interactive. In an aspect, the communication content may vary in response to a detected neurological state of the user calculated from biometric sensor data.

The immersive VR stereoscopic display device 400 may include a tablet support structure made of an opaque lightweight structural material (e.g., a rigid polymer, aluminum or cardboard) configured for supporting and allowing for removable placement of a portable tablet computing or smartphone device including a high-resolution display screen, for example, an LCD display. The device 400 is designed to be worn close to the user's face, enabling a wide field of view using a small screen size such as in smartphone. The support structure 426 holds a pair of lenses 422 in relation to the display screen 412. The lenses may be configured to enable the user to comfortably focus on the display screen 412 which may be held approximately one to three inches from the user's eyes.

The device 400 may further include a viewing shroud (not shown) coupled to the support structure 426 and configured of a soft, flexible or other suitable opaque material for form fitting to the user's face and blocking outside light. The shroud may be configured to ensure that the only visible light source to the user is the display screen 412, enhancing the immersive effect of using the device 400. A screen divider may be used to separate the screen 412 into independently driven stereoscopic regions, each of which is visible only through a corresponding one of the lenses 422. Hence, the immersive VR stereoscopic display device 400 may be used to provide stereoscopic display output, providing a more realistic perception of 3D space for the user.

The immersive VR stereoscopic display device 400 may further comprise a bridge (not shown) for positioning over the user's nose, to facilitate accurate positioning of the lenses 422 with respect to the user's eyes. The device 400 may further comprise an elastic strap or band 424, or other headwear for fitting around the user's head and holding the device 400 to the user's head.

The immersive VR stereoscopic display device 400 may include additional electronic components of a display and communications unit 402 (e.g., a tablet computer or smartphone) in relation to a user's head 430. When wearing the support 426, the user views the display 412 though the pair of lenses 422. The display 412 may be driven by the Central Processing Unit (CPU) 403 and/or Graphics Processing Unit (GPU) 410 via an internal bus 417. Components of the display and communications unit 402 may further include, for example, a transmit/receive component or components 418, enabling wireless communication between the CPU and an external server via a wireless coupling. The transmit/receive component 418 may operate using any suitable high-bandwidth wireless technology or protocol, including, for example, cellular telephone technologies such as 3rd 4th or 5th Generation Partnership Project (3GPP) Long Term Evolution (LTE) also known as 3G, 4G, or 5G, Global System for Mobile communications (GSM) or Universal Mobile Telecommunications System (UMTS), and/or a wireless local area network (WLAN) technology for example using a protocol such as Institute of Electrical and Electronics Engineers (118E) 802.11. The transmit/receive component or components 418 may enable streaming of video data to the display and communications unit 402 from a local or remote video server, and uplink transmission of sensor and other data to the local or remote video server for control or audience response techniques as described herein.

Components of the display and communications unit 402 may further include, for example, one or more sensors 414 coupled to the CPU 403 via the communications bus 417. Such sensors may include, for example, an accelerometer/inclinometer array providing orientation data for indicating an orientation of the display and communications unit 402.

As the display and communications unit 402 is fixed to the user's head 430, this data may also be calibrated to indicate an orientation of the head 430. The one or more sensors 414 may further include, for example, a Global Positioning System (GPS) sensor indicating a geographic position of the user. The one or more sensors 414 may further include, for example, a camera or image sensor positioned to detect an orientation of one or more of the user's eyes, or to capture video images of the user's physical environment (for VR mixed reality), or both. In some embodiments, a camera, image sensor, or other sensor configured to detect a user's eyes or eye movements may be mounted in the support structure 426 and coupled to the CPU 403 via the bus 416 and a serial bus port (not shown), for example, a Universal Serial Bus (USB) or other suitable communications port. The one or more sensors 414 may further include, for example, an interferometer positioned in the support structure 404 and configured to indicate a surface contour to the user's eyes. The one or more sensors 414 may further include, for example, a microphone, array or microphones, or other audio input transducer for detecting spoken user commands or verbal and non-verbal audible reactions to display output. The one or more sensors may include a subvocalization mask using electrodes as described by Arnav Kapur, Pattie Maes and Shreyas Kapur in a paper presented at the Association for Computing Machinery's ACM Intelligent User Interface conference in 2018. Subvocalized words might be used as command input, as indications of arousal or valence, or both. The one or more sensors may include, for example, electrodes or microphone to sense heart rate, a temperature sensor configured for sensing skin or body temperature of the user, an image sensor coupled to an analysis module to detect facial expression or pupil dilation, a microphone to detect verbal and nonverbal utterances, or other biometric sensors for collecting biofeedback data including nervous system responses capable of indicating emotion via algorithmic processing, including any sensor as already described in connection with FIG. 3 at 328.

Components of the display and communications unit 402 may further include, for example, an audio output transducer 420, for example a speaker or piezoelectric transducer in the display and communications unit 402 or audio output port for headphones or other audio output transducer mounted in headgear 424 or the like. The audio output device may provide surround sound, multichannel audio, so-called 'object oriented audio', or other audio track output accompanying a stereoscopic immersive VR video display content. Components of the display and communications unit 402 may further include, for example, a memory device 408 coupled to the CPU 403 via a memory bus. The memory 408 may store, for example, program instructions that when executed by the processor cause the apparatus 400 to perform operations as described herein. The memory 408 may also store data, for example, audio-video data in a library or buffered during streaming from a network node.

Having described examples of suitable clients, servers, and networks for performing signal processing of biometric sensor data for detection of neurological state in communication enhancement applications, more detailed aspects of suitable signal processing methods will be addressed. FIG. 5 illustrates an overview of a method 500 for calculating a Content Engagement Power (CEP), which may include four related operations in any functional order or in parallel. The operations may be programmed into executable instructions for a server as described herein.

A correlating operation 510 uses an algorithm to correlate biometric data for a user or user cohort to a neurological indicator. Optionally, the algorithm may be a machine-learning algorithm configured to process context-indicating data in addition to biometric data, which may improve accuracy. Context-indicating data may include, for example, user location, user position, time-of-day, day-of-week, ambient light level, ambient noise level, and so forth. For example, if the user's context is full of distractions, biofeedback data may have a different significance than in a quiet environment.

As used herein, a "measure" or "indicator" of neuro-physiological response is a machine-readable symbolic value that relates to a segment of communication content. The indicator or measure may have constituent elements, which may be quantitative or non-quantitative. For example, an indicator or measure may be designed as a multi-dimensional vector with values representing intensity of psychological qualities such as cognitive load, arousal, and valence. Valence in psychology is the state of attractiveness or desirability of an event, object or situation; valence is said to be positive when a subject feels something is good or attractive and negative when the subject feels the object is repellant or bad. Arousal is the state of alertness and attentiveness of the subject. A machine learning algorithm may include at least one supervised machine learning (SML) algorithm, for example, one or more of a linear regression algorithm, a neural network algorithm, a support vector algorithm, a naïve Bayes algorithm, a linear classification module or a random forest algorithm.

An event detection operation 520 analyzes a time-correlated signal from one or more sensors during output of communication content to a user and detects events wherein the signal exceeds a threshold. The threshold may be a fixed predetermined value, or a variable number such as a rolling average. An example for GSR data is provided herein below. Discrete measures of neuro-physiological response may be calculated for each event. Neurological state cannot be measured directly therefore sensor data indicates sentic modulation. Sentic modulations are modulations of biometric waveforms attributed to neurological states or changes in neurological states. In an aspect, to obtain baseline correlations between sentic modulations and neurological states, users may be shown a known visual stimulus (e.g., from focus group testing or a personal calibration session) to elicit a certain type of emotion. While under the stimulus, the test module may capture the user's biometric data and compare stimulus biometric data to resting biometric data to identify sentic modulation in biometric data waveforms.

CEP measurement and related methods may be used as a driver for branched (configurable) content. Measured errors between targeted story arcs and group response may be useful for informing design of the branched content, design and production of future content, distribution and marketing, or any activity that is influenced by a cohort's neuro-physiological response to the content. In addition, the measured errors can be used in a computer-implemented theater management module to control or influence real-time narrative branching or other management of a theater experience. Use of smartphones or tablets may be useful during focus group testing because such programmable devices already include one or more sensors for collection of biometric data. For example, Apple's™ iPhone™ includes front-facing stereographic cameras that may be useful for eye tracking, FAU detection, pupil dilation measurement, heartrate measurement and ambient light tracking, for example. Participants in the focus group may view the content on the smartphone or similar device, which collects biometric data with the participant's permission by a focus group application operating on their viewing device.

A normalization operation 530 performs an arithmetic or other numeric comparison between test data for known stimuli and the measured signal for the user and normalizes the measured value for the event. Normalization compensates for variation in individual responses and provides a more useful output. Once the input sensor events are detected and normalized, a calculation operation 540 determines a CEP value for a user or user cohort and records the values in a time-correlated record in a computer memory.

Machine learning, also called AI, can be an efficient tool for uncovering correlations between complex phenomena. As shown in FIG. 6, a system 600 responsive to sensor data 610 indicating a user's neurological state may use a machine learning training process 630 to detect correlations between sensory stimuli from a live theater experience and narrative stimuli 620 and biometric data 610. The training process 630 may receive stimuli data 620 that is time-correlated to the biometric data 610 from media player clients (e.g., clients 300, 402). The data may be associated with a specific user or cohort, or may be generic. Both types of input data (associated with a user and generic) may be used together. Generic input data can be used to calibrate a baseline for neuro-physiological response, to classify a baseline neuro-physiological response to a scene or arrangement of cinematographic elements. For example, if most users exhibit similar biometric tells when viewing a scene within a narrative context, the scene can be classified with other scenes that provoke similar biometric data from users. The similar scenes may be collected and reviewed by a human creative producer, who may score the scenes on neurological indicator metrics 640 using automated analysis tools. In an alternative, the indicator data 640 can be scored by human and semi-automatic processing without being classed with similar scenes. Human-scored elements of the live theater production can become training data for the machine learning process 630. In some embodiments, humans scoring elements of the communication content may include the users, such as via online survey forms. Scoring should consider cultural demographics and may be informed by expert information about responses of different cultures to scene elements.

The ML training process 630 compares human and machine-determined scores of scenes or other cinematographic elements and uses iterative machine learning methods as known in the art to reduce error between the training data and its own estimates. Creative content analysts may score data from multiple users based on their professional judgment and experience. Individual users may score their own content. For example, users willing to assist in training their personal "director software" to recognize their neurological states might score their own emotions while watching content. A problem with this approach is that the user scoring may interfere with their normal reactions, misleading the machine learning algorithm. Other training approaches include clinical testing of subject biometric responses over short content segments, followed by surveying the clinical subjects regarding their neurological states. A combination of these and other approaches may be used to develop training data for the machine learning process 630.

As used herein, biometric data provides a "tell" on how a user thinks and feels about their experience of communication content, i.e., are they engaged in the sense of entertainment value in narrative theory. Content Engagement Power is a measure of overall engagement throughout the user experience of communication content, monitored and scored during and upon completion of the experience. Overall user enjoyment is measured as the difference between expectation biometric data modulation power (as measured during calibration) and the average sustained biometric data modulation power. Measures of user engagement may be made by other methods and correlated to Content Engagement Power or made a part of scoring Content Engagement Power. For example, exit interview responses or acceptance of offers to purchase, subscribe, or follow may in included in or used to tune calculation of Content Engagement Power. Offer-response rates may be used during or after presentation of content to provide a more complete measure of user engagement.

The user's mood going into the interaction affects how the "story" is interpreted so the story experience should try to calibrate it out if possible. If a process is unable to calibrate out mood, then it may take it into account in the story arcs presented to favor more positively valenced interactions provided we can measure valence from the user. The instant system and methods will work best for healthy and calm individuals providing an interactive experience for everyone who partakes.

FIG. 7A shows an arrangement 700 of neurological states relative to axes of a two-dimensional neurological space defined by a horizontal valence axis and a vertical axis arousal. The illustrated emotions based on a valence/arousal neurological model are shown in the arrangement merely as an example, not actual or typical measured values. A media player client may measure valence with biometric sensors that measure facial action units, while arousal measurements may be done via GSR measurements for example.

Figure 7B:
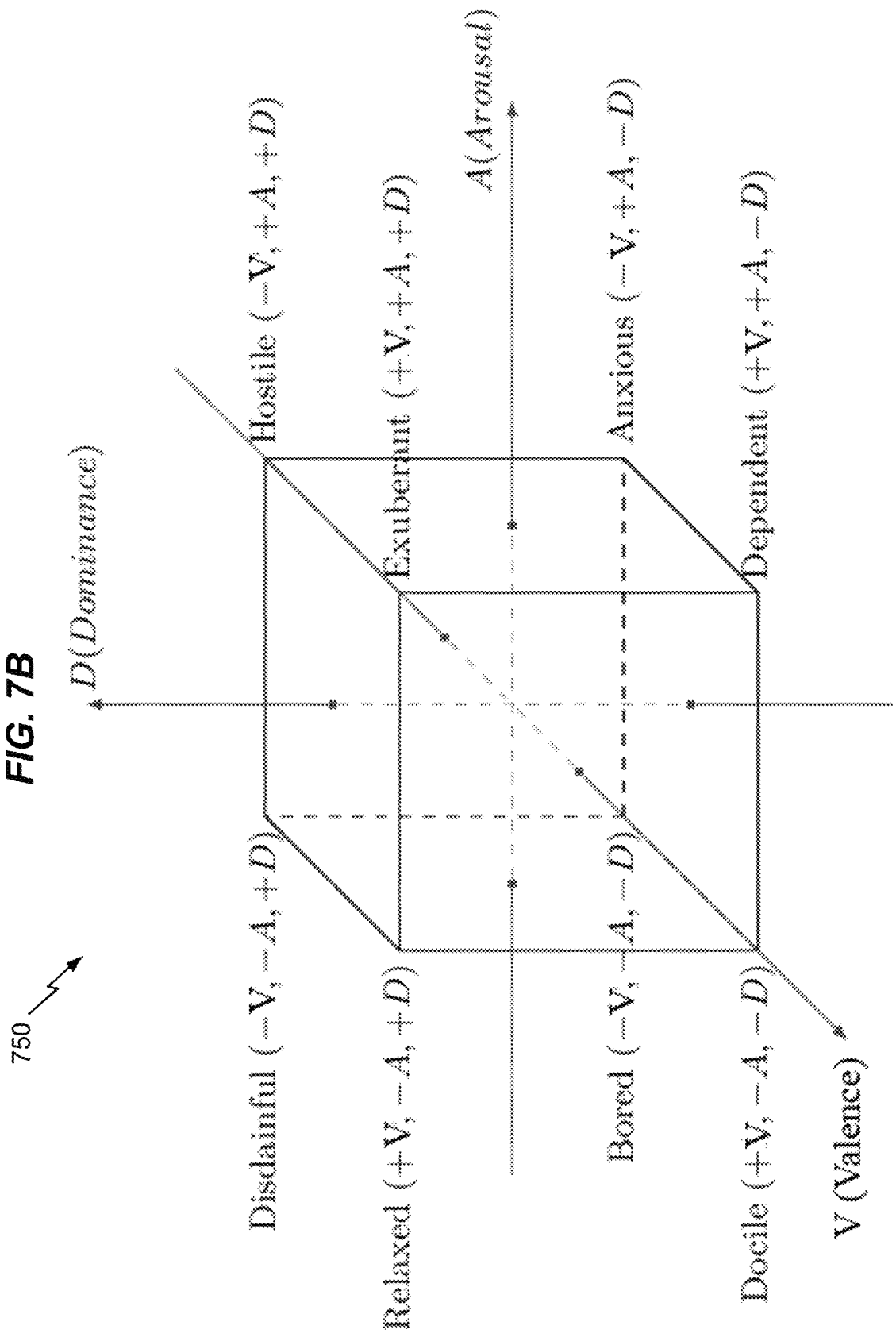
FIG. 7B is a diagram indicating an arrangement of neurological states relative to axes of a three-dimensional neurological space of a cognitive appraisal model.

Neurological spaces may be characterized by more than two axes. FIG. 7B diagrams a three-dimensional cognitive appraisal model 750 of a neurological space, wherein the third axis is social dominance or confidence. The model 750 illustrates a VAD (valence, arousal, confidence) cognitive appraisal model. The 3D model 750 may be useful for complex emotions where a social hierarchy is involved. In another embodiment, an engagement measure from biometric data may be modeled as a three-dimensional vector which provides cognitive workload, arousal and valence from which a processor can determine primary and secondary emotions after calibration. Engagement measures may be generalized to an N-dimensional model space wherein N is one or greater. In examples described herein, CEP as described herein is in a two-dimensional space 700 with valence and arousal axes, but a useful cognitive appraisal model is not limited thereby. For example, confidence is another psychological axis of measurement that might be added, other axes may be added, and base axes other than valence and arousal might also be useful. Any cognitive appraisal model that maps biometric data to different cognitive parameters in a vector space may be used with the methods described herein. Baseline arousal, valence, dominance and other cognitive parameters may be determined on an individual basis during emotion calibration.

In the following detailed example, neurological state determination from biometric sensors is based on the valence/arousal neurological model where valence is (positive/negative) and arousal is magnitude. From this model, producers of live theater and other creative productions can verify the intention of the creative work by measuring narrative theory constructs such as tension (hope vs. fear) and rising tension (increase in arousal over time) and more. During presentation of live or recorded story elements, an algorithm can use the neurological model to change story elements dynamically based on the psychology of the user, as described in more detail in U.S. provisional patent application 62/614,811 filed Jan. 8, 2018. The present disclosure focuses on determining a useful measure of neurological state correlating to engagement with directed entertainment—the CEP—for real-time and offline applications, as described in more detail below. The inventive concepts described herein are not limited to the neurological model described herein and may be adapted for use with any useful neurological model characterized by quantifiable parameters.

In a test environment, electrodes and other sensors can be placed manually on subject users in a clinical function. For consumer applications, sensor placement should be less intrusive and more convenient. For example, image sensors in visible and infrared wavelengths can be built into display equipment. For further example, a phased-array radar emitter may be fabricated as a microdevice and placed behind the display screen of a mobile phone or tablet, for detecting biometric data such as Facial Action Units or pupil dilation. Where a user wears gear or grasps a controller as when using VR equipment, electrodes can be built into headgear, controllers, and other wearable gear to measure skin conductivity, pulse, and electrical activity.

Target story arcs based on communication content can be stored in a computer database as a sequence of targeted values in any useful neurological model for assessing engagement with content, for example a valence/arousal model. Using the example of a valence/arousal model, a server may perform a difference calculation to determine the error between the planned/predicted and measured arousal and valence. The error may be used in content control. Once a delta between the predicted and measured values passes a threshold, then the story management software may select a next or future segment of the communication. For example, if the user's valence is in the "wrong" direction based on the targeted story arc then the processor may change the content by the following logic: If absolute value of (Valence Predict−Valence Measured)>0 then Change Content. The change in content can be several different items specific to what the software has learned about the user or it can be a trial or recommendation from an AI process. Likewise, if the arousal error falls below a threshold (e.g. 50%) of predicted (Absolute value of (error)>0.50*Predict) then the processor may select a different content segment.

Figure 8:
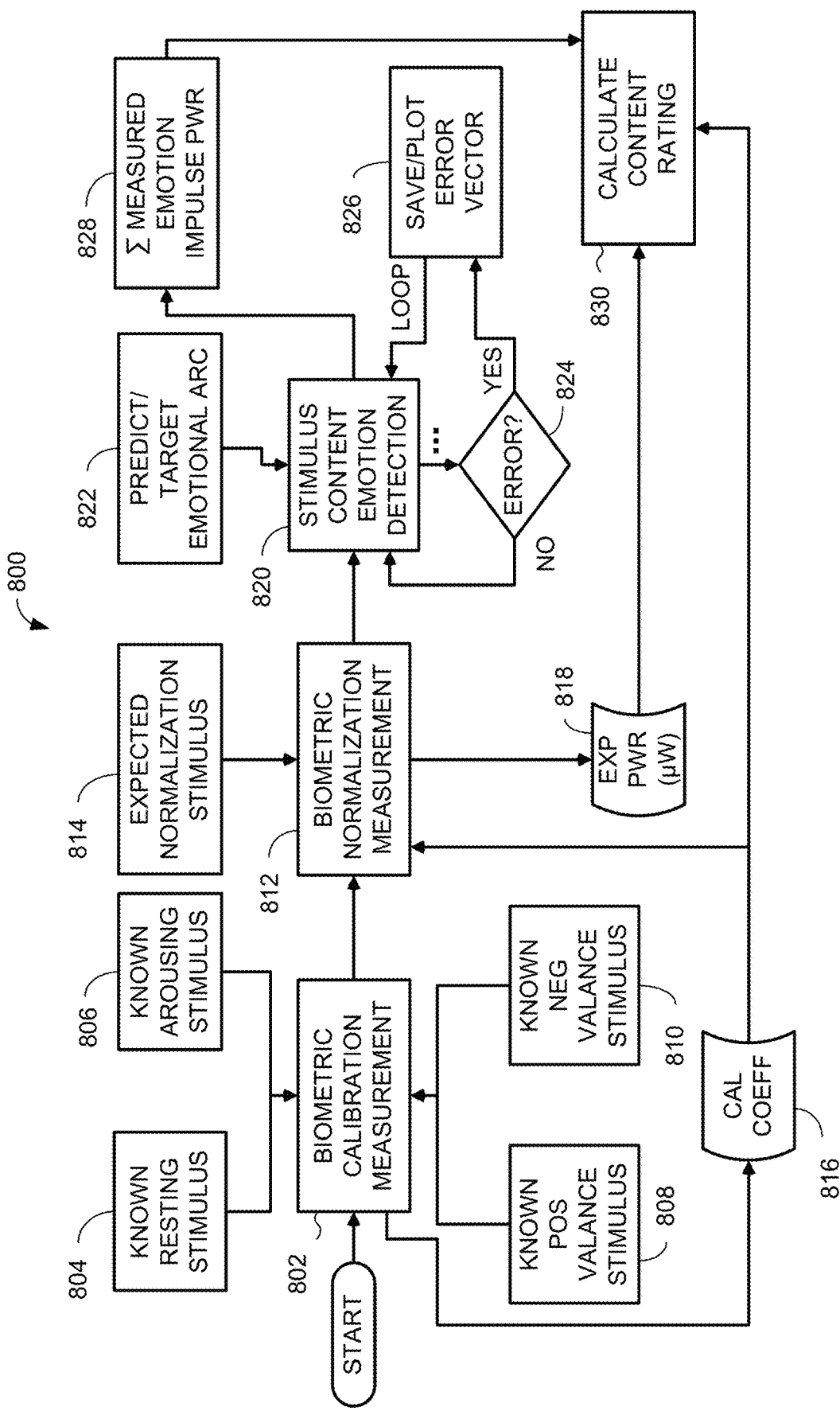
FIG. 8 is a flow chart illustrating a process and algorithms for determining a content engagement rating based on neuro-physiological response data.

FIG. 8 shows a method 800 for determining a content rating for communication content, including Content Engagement Power (CEP). The method may be implemented by encoding as an algorithm executable by a computer processor and applied in other methods described herein wherever a calculation of CEP is needed. CEP is a ratio of a sum of event power '$P_v$' for the subject content to expectation power '$P_x$' for comparable content in the genre. $P_v$ and $P_x$ are calculated using the same methodology for different subject matter and in the general case for different users. As such, the sums cover different total times, event power $P_v$ covering a time period '$t_v$' that equals a sum of 'n' number of event power periods $\Delta t_v$ for the subject content:

$$t_v = \sum_n^1 \Delta t_v \qquad \text{Eq. 1}$$

Likewise, expectation power $P_x$ covers a period '$t_x$' that equals a sum of 'm' number of event power periods $\Delta t_x$ for the expectation content:

$$t_x = \sum_m^1 \Delta t_x \qquad \text{Eq. 2}$$

Each of powers $P_v$ and $P_x$ is, for any given event 'n' or 'm', a dot product of a power vector P and a weighting vector W of dimension i, as follows:

$$P_{v_n} = \vec{P_v} \cdot \vec{W} = \sum_i^1 P_{v_i} W_i = P_{v_1} W_1 + P_{v_2} W_2 + \ldots + P_{v_i} W_i \qquad \text{Eq. 3}$$

$$P_{x_m} = \vec{P_x} \cdot \vec{W} = \sum_i^1 P_{x_i} W_i = P_{x_1} W_1 + P_{x_2} W_2 + \ldots + P_{x_i} W_i \qquad \text{Eq. 4}$$

In general, the power vector $\vec{P}$ can be defined variously. In any given computation of CEP the power vectors for the subject content and the expectation baseline should be defined consistently with one another, and the weighting vectors should be identical. A power vector may include arousal measures only, valence values only, a combination of arousal measures and valence measures, or a combination of any of the foregoing with other measures, for example a confidence measure. In one embodiment, CEP is calculated using power vectors $\vec{P}$ defined by a combination of 'j' arousal measures '$a_j$' and 'k' valence measures '$v_k$', each of which is adjusted by a calibration offset 'C' from a known stimulus, wherein j and k are any non-negative integer, as follows:

$$\vec{P}_C = (a_1 C_1, \ldots, a_j C_1, v_1 C_{j+1}, \ldots, v_k C_{j+k}) \qquad \text{Eq. 5}$$

wherein $$C_j = S_j - S_j O_j = S_j(1 - O_j) \qquad \text{Eq. 6}$$

The index 'j' in Equation 6 signifies an index from 1 to j+k, $S_j$ signifies a scaling factor and $O_j$ signifies the offset between the minimum of the sensor data range and its true minimum. A weighting vector $\vec{W}$ corresponding to the power vector of Equation 5 may be expressed as:

$$\vec{W} = (w_1, \ldots w_j, w_{j+1}, \ldots w_k) \qquad \text{Eq. 7}$$

wherein each weight value scales its corresponding factor in proportion to the factor's relative estimated reliability.

With calibrated dot products $P_{v_n}$, $P_{x_m}$ given by Equations 3 and 4 and time factors as given by Equations 1 and 2, a processor may compute a content engagement power (CEP) for a single user as follows:

$$CEP_{user}(dBm) = 10 \cdot \log_{10}\left(\frac{\sum_n^1 P_v \Delta t_v}{\sum_m^1 P_x \Delta t_x} \cdot \frac{t_x}{t_v}\right) \qquad \text{Eq. 8}$$

The ratio $t_x/t_v$ normalizes inequality in the disparate time series sums and renders the ratio unitless. A user CEP value greater than 1 indicates that a user/player-actor/viewer has had an engaging experience above their expectations relative to the genre. A user CEP value less than 1 indicates that engagement is less than the user's expectations for the content genre.

CEP can also be calculated for content titles, scenes in live theater and entire live theater productions across audiences of 'v' users as a ratio of the content event power for the 'x' users to the expectation power for 'm' not necessarily identical users, as follows:

$$CEP_{title}(dBm) = 10 \cdot \log_{10}\left(\frac{\sum_v^1 \sum_n^1 P_v \Delta t}{\sum_x^1 \sum_m^1 P_x \Delta t} \cdot \frac{xt_x}{vt_v}\right) \quad \text{Eq. 9}$$

The variables v and x are the number of content users and engagement baseline viewers, respectively. The audience expectation power in the denominator represents the expectation that the audience brings to the content, while event power in the numerator represents the sum of the audience's arousal or valence events while experiencing the content. The processor sums the event power over each event (n) and user (v), and the expectation power over each event (m) and user (x). It then calculates the CEP by calculating the ratio of event power to expectation power and normalizing disparate time sums and audience counts by the ratio $xt_x/vt_v$. The CEP is a component of content rating. Other components of content rating may include aggregate valence error and valence error for valence targets (e.g., triumph, despair, etc.).

Equation 5 describes a calibrated power vector made up of arousal and valence measures derived from biometric sensor data. In an alternative, the processor may define a partially uncalibrated power vector in which the sensor data signal is scaled as part of lower-level digital signal processing before conversion to a digital value but not offset for a user as follows:

$$\vec{P} = (a_1, \ldots, a_j, v_1, \ldots, v_k) \quad \text{Eq. 10}$$

If using a partially uncalibrated power vector, an aggregate calibration offset may be computed for each factor and subtracted from the dot products $P_{v_n}$, $P_{x_m}$ given by Equations 3 and 4 before calculating Content Engagement Power (CEP). For example, an aggregate calibration offset for $P_{v_n}$ may be given by:

$$C_v = i(\overline{C_v} \cdot \overline{W}) = i \sum_i^1 C_{v_i} W_i = C_{v_1} W_1 + C_{v_2} W_2 + \ldots + C_{v_i} W_i \quad \text{Eq. 11}$$

In such case, a calibrated value of the power vector $P_{v_n}$ can be computed by:

$$P_{v_n} - C_{v_n} \quad \text{Eq. 12}$$

The calibrated power vector $P_{x_m}$ can be similarly computed.

Referring again to the method 800 in which the foregoing expressions can be used (FIG. 8), a calibration process 802 for the sensor data is first performed to calibrate user reactions to known stimuli, for example a known resting stimulus 804, a known arousing stimulus 806, a known positive valence stimulus 808, and a known negative valence stimulus 810. The known stimuli 806-810 can be tested using a focus group that is culturally and demographically like the target audience and maintained in a database for use in calibration. For example, the International Affective Picture System (ZAPS) is a database of pictures for studying emotion and attention in psychological research. For consistency with the content platform, images or these found in the IAPS or similar knowledge bases may be produced in a format consistent with the targeted platform for use in calibration. For example, pictures of an emotionally-triggering subject can be produced as video clips. Calibration ensures that sensors are operating as expected and providing data consistently between users. Inconsistent results may indicate malfunctioning or misconfigured sensors that can be corrected or disregarded. The processor may determine one or more calibration coefficients 816 for adjusting signal values for consistency across devices and/or users.

Calibration can have both scaling and offset characteristics. To be useful as an indicator of arousal, valence, or other psychological state, sensor data may need calibrating with both scaling and offset factors. For example, GSR may in theory vary between zero and 1, but in practice depend on fixed and variable conditions of human skin that vary across individuals and with time. In any given session, a subject's GSR may range between some $GSR_{min} > 0$ and some $GSR_{max} < 1$. Both the magnitude of the range and its scale may be measured by exposing the subject to known stimuli and estimating the magnitude and scale of the calibration factor by comparing the results from the session with known stimuli to the expected range for a sensor of the same type. In many cases, the reliability of calibration may be doubtful, or calibration data may be unavailable, making it necessary to estimate calibration factors from live data. In some embodiments, sensor data might be pre-calibrated using an adaptive machine learning algorithm that adjusts calibration factors for each data stream as more data is received and spares higher-level processing from the task of adjusting for calibration.

Once sensors are calibrated, the system normalizes the sensor data response data for genre differences at 812, for example using Equation 8 or 9. Different genres produce different valence and arousal scores. For example, action-adventure genres have a different pace, story target, and intensity. Thus, engagement power cannot be compared across genres unless the engagement profile of the genre is considered. Genre normalization scores the content relative to content in the same genre, enabling comparison on an equivalent basis across genres. Normalization 812 may be performed on a test audience or focus group, or on the subject group prior to the main feature, using an expected normalization stimulus 814. For example, the audience may view one or more trailers in the same genre as the main feature, and event power may be calculated for the one or more trailers. In an alternative, archived data for the same users or same user cohort may be used to calculate expectation power. Expectation power is calculated using the same algorithms as used or will be used for measurements of event power and can be adjusted using the same calibration coefficients 816. The processor stores the expectation power 818 for later use.

At 820, a processor receives sensor data during play of the subject content and calculates event power for each measure of concern, such as arousal and one or more valence qualities. At 828, the processor sums or otherwise aggregates the event power for the content after play is concluded, or on a running basis during play. At 830, the processor calculates the content rating, including the content engagement power (CEP) as previously described. The processor first applies applicable calibration coefficients and then calculates the CEP by dividing the aggregated event power by the expectation power as described above.

Optionally, the calculation function 820 may include comparing, at 824, an event power for each detected event, or for a lesser subset of detected events, to a reference story arc defined for the content. A reference arc may be, for example, a targeted arc defined by a creative producer, a predicted arc, a past arc or arcs for the content, or a combination of the foregoing. At 826, the processor may save, increment or otherwise accumulate an error vector value describing the error for one or more variables. The error vector may include a difference between the references arc and a measured response for each measured value (e.g., arousal and valence values) for a specified scene, time period, or set of video frames. The error vector and matrix of vectors may be useful for content evaluation or content control.

Error measurements may include or augment other metrics for content evaluation. Content engagement power and error measurements may be compared to purchases, subscriptions, or other conversions related to presented content. The system may also measure consistency in audience response, using standard deviation or other statistical measures. The system may measure content engagement power, valence and arousal for individual, cohorts, and aggregate audiences. Error vectors and CEP may be used for a variety of real-time and offline task. In some embodiments the measures may be used for content control for example as described in U.S. provisional patent application Ser. No. 62/566,257 filed Sep. 29, 2017 and Ser. No. 62/614,811 filed Jan. 8, 2018, incorporated by reference herein.

Further details of digitally representing user engagement with linguistic content, including but not limited to digital representation of Content Engagement Power (CEP) based on biometric sensor data, may be as described in U.S. Patent App. Ser. No. 62/661,556 filed Apr. 23, 2018. Digital representation of user engagement in a computer memory based on biometric data may find many applications, some of which are further described herein below. These applications include generating a script for actors in an interactive or non-interactive performance, generating information useful for script writers and other creative producers, controlling progress through a linguistic work, and other uses as claimed herein.

Figure 9:
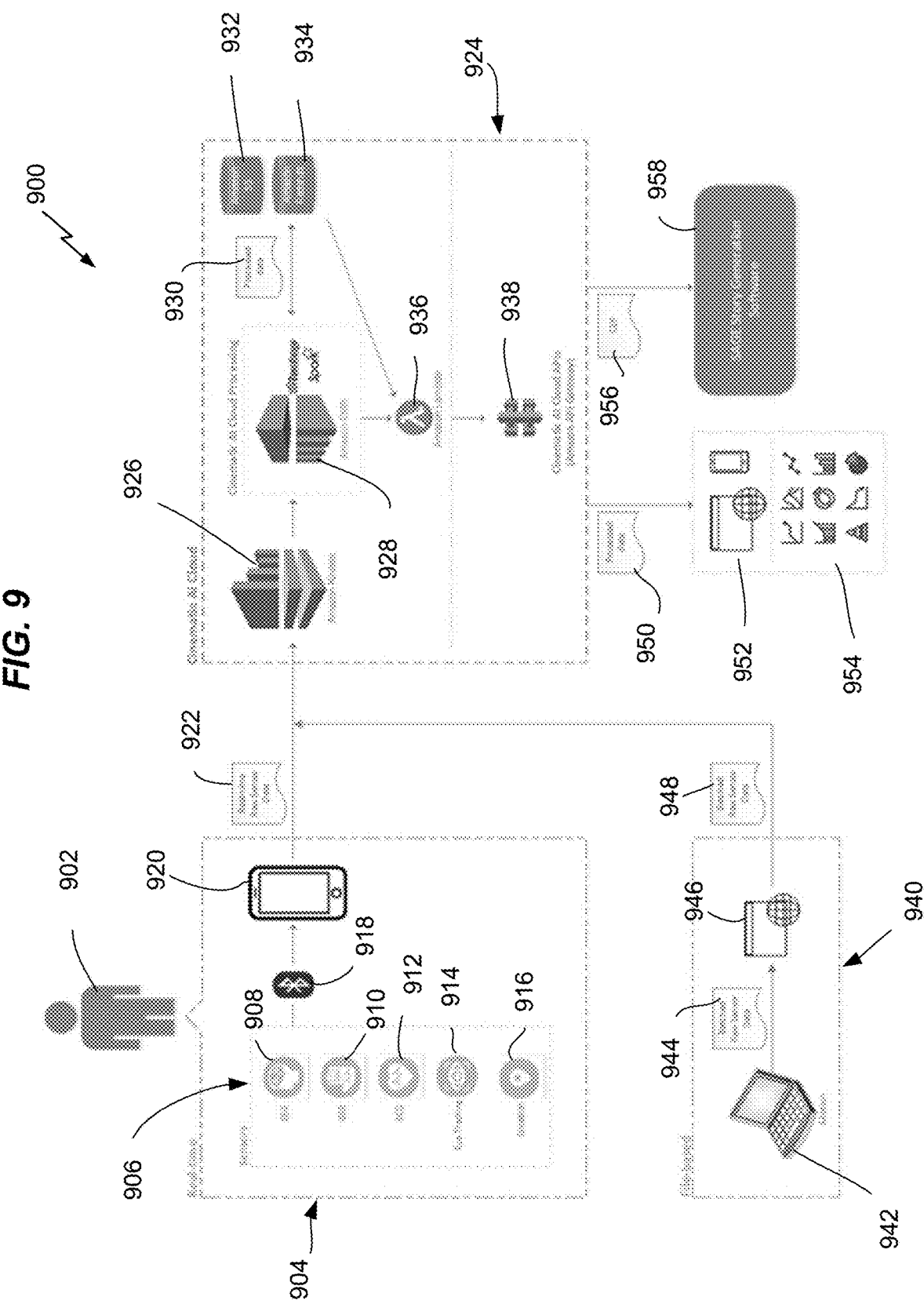
FIG. 9 is a diagram illustrating a system for collecting neuro-physiological response data using a mobile device and cooperating applications.

In an aspect of controlling communication content driven by biometric input, users may use a mobile application (e.g., "Sage QCI") and device for signaling biometric data and other information. FIG. 9 shows a system 900 for collecting and using biometric response data from a person 902 (e.g., a user or player-actor) for interactive entertainment using an application or system 904 installed on a mobile device 920, for example, a smartphone. One or more biometric sensors may be coupled to the mobile device 920 via a Bluetooth connection 918 or other suitable coupling. In an alternative, sensors may be built into the mobile device 920 and communicate with its processor via a bus or serial port. Biometric sensors 906 may include an electroencephalographic (EEG) sensor 908, galvanic skin response sensor 910, electrocardiogram sensor 912, eye tracking and facial expression sensor 914, and location sensor 916. A processor of the mobile device 920 may transmit raw sensor data to a cloud-based data processing system 924 that generates a measure of content engagement 956 (e.g., a CEP) and other processed data 950. The content engagement software 956 may be provided to a story management module or application 958 for control of communication content as described herein. Other processed data 950 may include, for example usage analytic data 952 for content titles and trend data 954 aggregated over one or more content titles.

Other input to the data analytics system 924 may include batched raw sensor data 948. Batched data 948 may be collected in non-real-time and stored offline, for example in a personal computing device 942 storing batched biometric data 944 in a local data store, which may be uploaded from time to time via a website or other portal to a data analytics server 924. Offline or non-real-time data may be useful for developing user profiles or retrospective analysis, for example.

A data analytics system 924 may perform distributed processing with two update rates (fast and slow packets). The mobile device 920 may process the raw biometric data in fast mode and only send data summaries over a data packet to the cloud analytics system 924 for further processing. In slow mode the raw data files may be uploaded at a slower data rate for post-session processing. The data analytics system 924 may be configured variously. In some embodiments, the server 924 may include an Amazon™ Kinesis front-end 926 for receiving, caching and serving incoming raw data within the analytics system 924. A data processing component 928 may process the raw biometric data using machine-learning and rules-based algorithms as described elsewhere herein. Processed data may be exchanged with longer-term storage units 932 and 934. A serverless computing platform 936 (e.g., Amazon lambda) may be used for convenience, providing code execution and scale without the overhead of managing instances, availability and runtimes on servers. Provision of processed data 930 from the data analytics system 924 may be managed via an Application Program Interface (API) 938.

Figure 11:
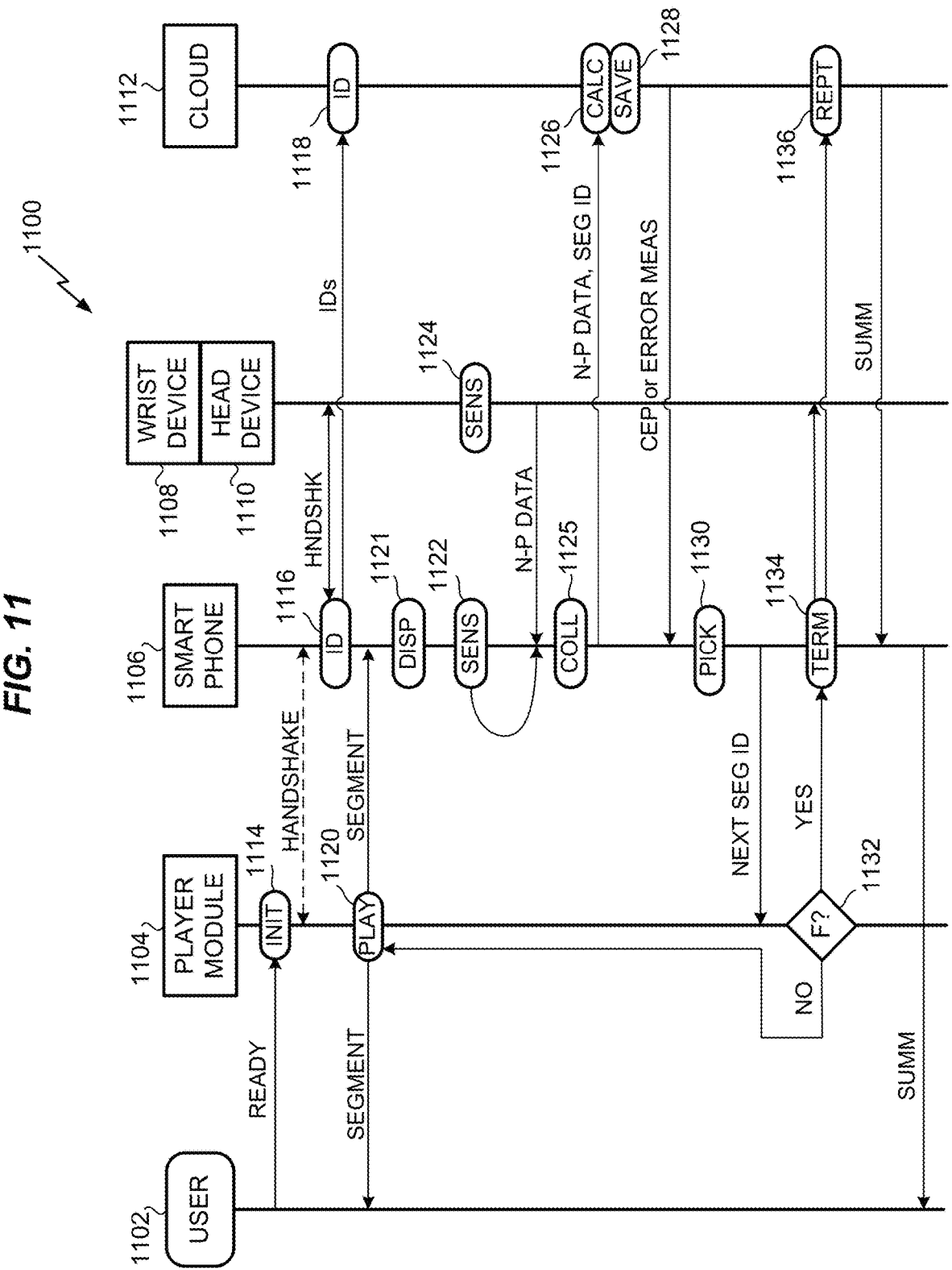
FIG. 11 is a sequence diagram illustrating aspects of collecting neuro-physiological response data using a mobile device with auxiliary sensor devices.

FIG. 11 shows a mobile system 1000 for a user 1002 including a mobile device 1004 with sensors and accessories 1112, 1120 for collecting biometric data used in the methods and apparatus described herein and a display screen 1006. The mobile system 1000 may be useful of real-time control or for non-real-time applications such as traditional content-wide focus group testing. The mobile device 1004 may use built in sensors commonly included on consumer devices (phones, tables etc.) for example a front facing stereoscopic camera 1008 (portrait) or 1010 (landscape). Often included by manufacturers for face detection identity verification, cameras 1008, 1010 may also be used for eye tracking for tracking attention, FAU for tracking CEP-valence, pupil dilation measurement tracking CEP-arousal and heartrate as available through watch accessory 1014 including a pulse detection sensor 1014, or by the mobile device 1004 itself.

Accessories like a headphone 1020, hats or VR headsets may be equipped with EEG sensors 1022. A processor of the mobile device may detect arousal by pupil dilation via the 3D cameras 1008, 1010 which also provide eye tracking data. A calibration scheme may be used to discriminate pupil dilation by aperture (light changes) from changes to do emotional arousal. Both front & back cameras of the device 1004 may be used for ambient light detection, for calibration of pupil dilation detection factoring out dilation caused by lighting changes. For example, a measure of pupil dilation distance (mm) versus dynamic range of light expected during the performance for anticipated ambient light conditions may be made during a calibration sequence. From this, a processor may calibrate out effects from lighting vs. effect from emotion or cognitive workload based on the design of the narrative by measuring the extra dilation displacement from narrative elements and the results from the calibration signal tests.

Instead of, or in addition to a stereoscopic camera 1008 or 1010, a mobile device 1004 may include a radar sensor 1030, for example a multi-element microchip array radar (MEMAR), to create and track facial action units and pupil dilation. The radar sensor 1030 can be embedded underneath and can see through the screen 1006 on a mobile device 1004 with or without visible light on the subject. The screen 1006 is invisible to the RF spectrum radiated by the imaging radar arrays, which can thereby perform radar imaging through the screen in any amount of light or darkness. In an aspect, the MEMAR sensor 1030 may include two arrays with 6 elements each. Two small RF radar chip antennas with six elements each create an imaging radar. An advantage of the MEMAR sensor 1130 over optical sensors 1008, 1010 is that illumination of the face is not needed, and thus sensing of facial action units, pupil dilation and eye tracking is not impeded by darkness. While only one 6-chip MEMAR array 1030 is shown, a mobile device may be equipped with two or more similar arrays for more robust sensing capabilities.

Certain aspects of the foregoing methods and apparatus may be adapted for use in a screenwriting application for interactive entertainment, including an application interface which allows screenwriters to define variables related to psychological profiles for players and characters. The application may enable the screenwriter to create a story by defining variables and creating matching content. For example, a writer might track player parameters such as personality, demographic, socio-economic status during script writing and set variables (at the writer's discretion) for how the script branches based on the player parameters. In addition, the application may enable writers to place branches in the scripts that depend on neurological state of players. The application may facilitate development of branching during readback, by presenting choices as drop-down menus or links like a choose your own adventure book. The screen writer can manage and create the branches via the graphical interface as well as within the scripting environment. The application may assist screenwriters with managing non-player character profiles, for example by making recommendations for dialog and actions based on player profile and action in scene by other non-player characters and also by interactions by players and other non-players.

Drafts of scripts may be produced by simulating character interactions using a personality model. Building on available character data profile information, a script-writing application may use machine learning and trials (e.g., player-actor trials) through a simulation to build scripts for traditional linear narrative. Each "played" path through the simulation can be turned into a linear script based on the data collected on how simulated player-actors have performed during the simulation. For example, recorded interactions, dialog, and other elements depend from all the biometric sensor data and player-actor/NPC character profile data. The application may compare alternative drafts and identify drafts most likely to be successful. Recommendations may be largely based on profile data matches as well as matches across genre type, demographics, backstory, character types/role in relation to the narrative structure. The application may use a database built on character profiles/backstory as well a database to store player-actor trial data, story arcs, biometric data, and other relevant data.

The application may use machine learning to identify patterns in character reactions based on profile data, emotional responses and interactions (stored player-actor interactions from simulation trials). Draft scripts are based on simulated competition, conflict, and other interactions between computer-controlled non-player characters (NPCs). NPC interactions and dialog may be informed or generated by random selection from a corpus of stored film data character profiles, story arcs, emotional arcs, dialog and interactions across a multitude of stories. Permutations (NPC to NPC trials) are scored against popular story arc data to return a percentage score of likability based on past data. Trials above 95% or 99% story arc similarity to popular stories may be retuned for analysis by a human.

In addition or in the alternative to defining major elements such as character and story arc, synthetic content designs may use more granular 'atomic elements' such as lighting, color schemes, framing, soundtracks, point of view (POV) or scene change moments, to improve the audience engagement of the production, not just to select a pre-shot scene or node to show next. Using feedback based on emotional tells allows producers to inform and guide the designers and script-writers and camerawomen and colorists and soundtrack selectors etc. to create content that better engages audiences. The point is not just to create dynamic stories, or call up different NPCs, but to alter more granular aspects ('atomic elements') of productions based upon emotional tells determined via the relevant sensors. This could be used to fashion better versions for greenlighting or for production re-design, and in real-time if possible.

Synthetic content design may be used for pre-visualization (pre-viz) for previews, perhaps with brute-force already-shot different versions or using CGI and pre-viz hardware to present different alternatives. Depending on available computational bandwidth, CGI rendered content may react in real time so that audience-preferred lighting, soundtrack, framing, etc. is incorporated in the output as the presentation proceeds.

Figure 10:
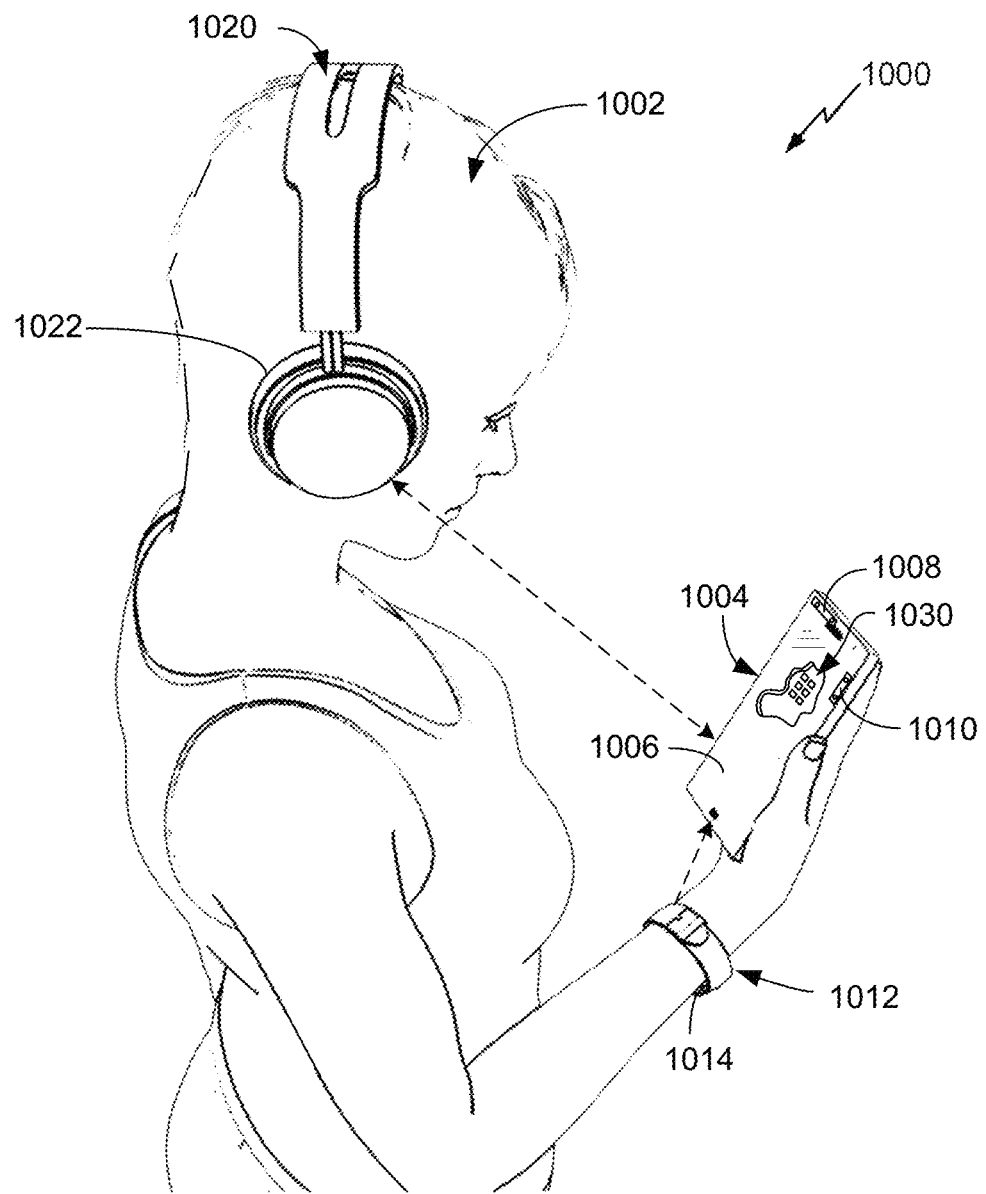
FIG. 10 is a perspective view of a user using a mobile application with sensors and accessories for collecting neuro-physiological data used in the methods and apparatus described herein.

The systems and apparatus described in connection with FIGS. 9-10 may be used to perform methods as described herein in connection with FIGS. 20-21 and elsewhere. FIG. 11 shows an example of a sequence 1100 by and between components of a system for collecting neuro-physiological response data using a mobile device with auxiliary sensor devices. In one use case, the user 1102 watches entertainment on another screen of a player device or module 1104 while the smart phone 1106 or similar mobile device acts as a biometric sensor hub and connection node. The smart phone 1106 may display ancillary information during presentation of the content by the player module 1104, attracting occasional attention of the user 1102. When the user looks at the screen of the smart phone 1106, the smartphone may collect neuro-physiological data using its biometric sensors, for example, the phone 1106 may collect FAU and pupil dilation from a glance. If the user touches the phone's touch screen or fingerprint sensor, the smart phone 1106 may collect a pulse. In an alternative, or in addition, the smart phone may be mounted or otherwise supported so that the user 1102 is within its sensor range while consuming the content. The cloud component 1112 may be, or may include, a cloud server 924 as described in connection with FIG. 9, or equivalent. Equivalent servers may include conventional single-node servers, server farms, or distributed server systems (e.g., blockchain).

Optionally, the smart phone 1106 may work in cooperation with one or more auxiliary sensors, for example a wrist device 1108 such as a smart watch or fitness band, a head-mounted device 1110 such as a headband, hat, or visor for collecting EEG and GSR, or a finger-mounted device (not shown). The auxiliary devices 1106, 1108 may communicate wirelessly with the smartphone 1106 using Bluetooth or other wireless protocol. The sequence of operation may be the same for various auxiliary devices so these are shown on the same line, despite operating independently of one another.

In other use cases, the smartphone 1106 and player module 1104 may be combined in a single device. For example, the user may consume content displayed on the screen of the smartphone 1106, directly or via an intermediary device such as, for example, virtual reality headgear or a smart television receiving a streaming audio-video feed from the smartphone 1106.

A sequence 1100 may begin with the user 1102 causing the player module 1104 to initiate play 1114 of a desired communication content title, experience or work. The smartphone 1106 may detect initiation of the session via a handshake or detection of a signal from the player module 1104, and collect identifiers 1116 for the content title, experience or work and for the user. The smart phone 1106 may activate the auxiliary sensor devices 1108, 1110 and provide the identifying information to the cloud server 1112, which may register the identifiers 1118 as parameters of a session.

The player module 1120 may play the first segment of content, for example, a video clip, audio clip, audio-video clip, page of text, graphic image, or other linguistic or non-linguistic content by outputting to its display system, audio system, and/or other available output system. At 1121 (optional), if the smart phone is not displaying the content, it may display auxiliary content to attract the user's gaze as previously described. At 1122, the smart phone 1106 may collect sensor data from sensors as previously described. Similarly, at 1124 the auxiliary devices 1108, 1110 may collect sensor data. The smart phone 1106 may collect and collate the sensor data at 1125, optionally pre-processing the data to a more compact form. Then, the smart phone may send the raw and processed data with a segment identifier to the cloud server 1112, which based on the data calculates 1126 a measure of engagement (e.g., CEP) or other neurophysiological indicator or error indicator relative to a narrative arc as described elsewhere herein, and saves the calculation results 1128 in a data store. The cloud server 1112 may provide the calculation results, or a subset thereof, to the smartphone 1106. Based on the results, the smartphone (or in an alternative, the cloud server) selects 1130 a next segment.

Algorithms for selecting a next segment may depend on the use case. In an end consumer use case, the algorithm may select a next segment to correct error relative to a narrative arc, to provide a more pleasant or intense experience, or other objective of the use case. In a focus group use case, the algorithm may select a segment to clarify the reaction of the user to a prior segment or other test objective. After selecting a next segment, the smart phone 1106 may send an identifier for the next segment to the player module 1104. At 1132, if play of the communication content is not finished, the sequence may loop back to 1120. If play is finished, the smart phone 1106 may terminate sessions with the auxiliary sensor devices 1101, 1110 and cloud server 1112 by sending a termination signal. Upon receiving a termination signal, the cloud server may generate a report 1136 for its data store and provide a summary to the smart phone 1106, which may provide the summary to the user 1102.

Figure 12:
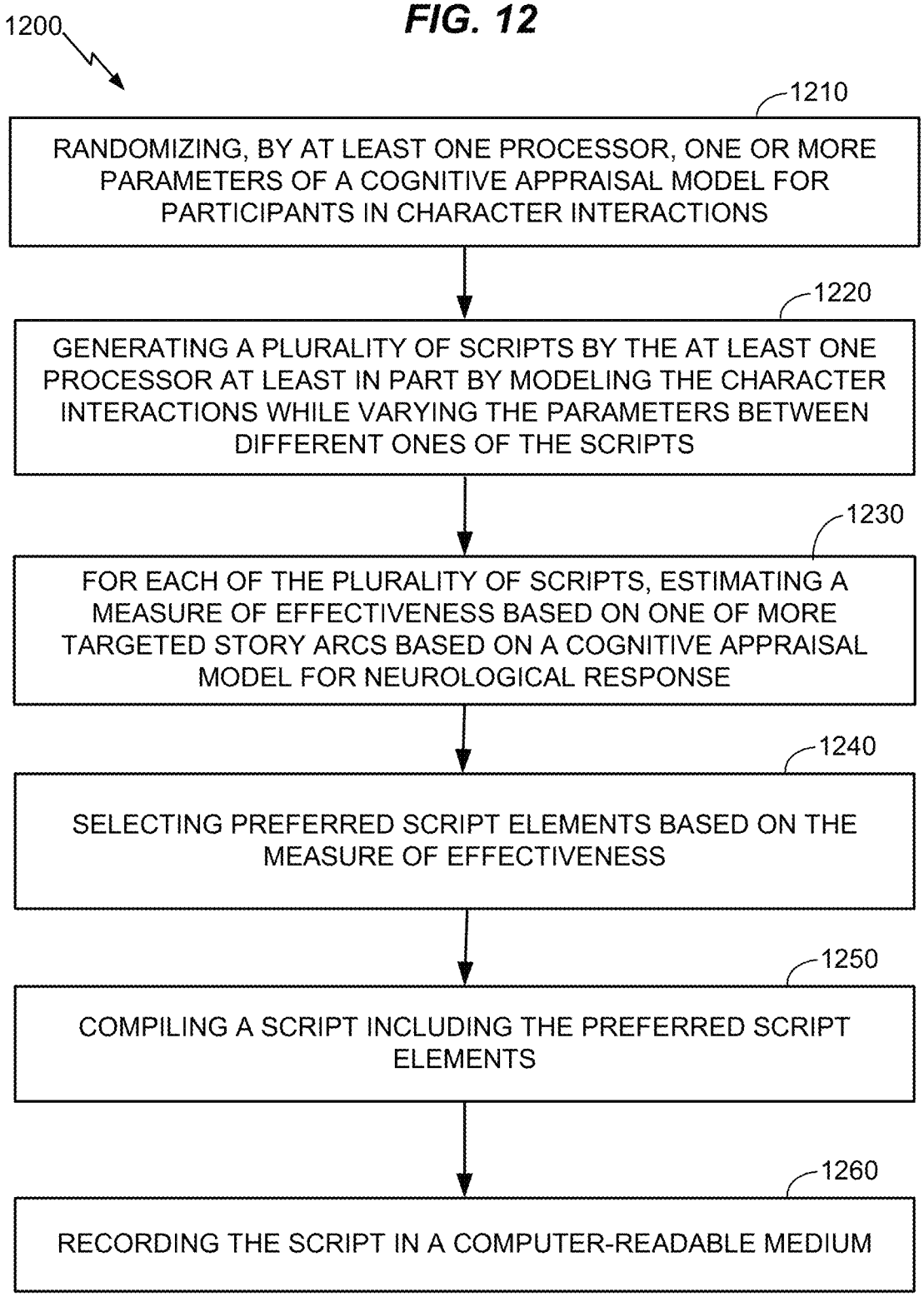
FIG. 12 is a flow chart illustrating aspects of a method for operating an apparatus or system that automatically produces or edits a script for a dramatic production.

In view the foregoing, and by way of additional example, FIG. 12 shows aspects of a method 1200 or methods for generating a script or a portion of a script using an automatic algorithm. The computer-implemented method 1200 for generating a script may include, at 1210, randomizing, by at least one processor, one or more parameters of a cognitive appraisal model for participants in character interactions. The cognitive appraisal model may be one as described for calculating CEP, or other model as described in connection with FIGS. 7A-B above. The method 1200 may include, at 1220, generating a plurality of scripts by the at least one processor at least in part by modeling the character interactions while varying the parameters between different ones of the scripts. The method may include, at 1230, for each of the plurality of scripts, estimating a measure of effectiveness based on one of more targeted story arcs based on a cognitive appraisal model for neuro-physiological response, by the at least one processor. The method may include, at 1240, selecting preferred script elements by the at least one processor based on the measure of effectiveness estimated at block 1230. The method may include at 1250 compiling, by the at least one processor, a script that includes the preferred script elements selected at block 1250. The method 1200 may include, at 1260, recording the script in a computer-readable medium.

Figure 13:
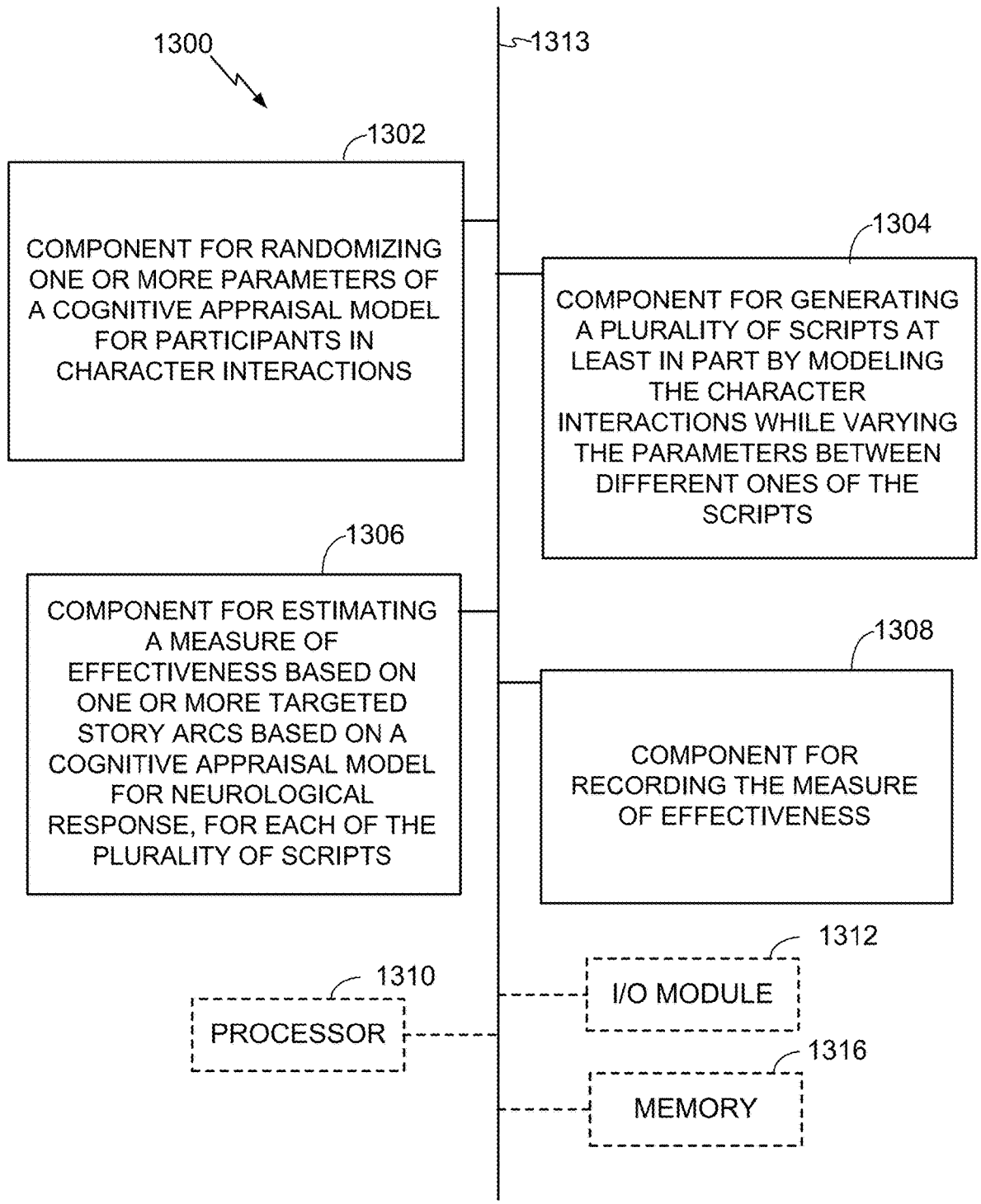
FIG. 13 is a conceptual block diagram illustrating components of an apparatus or system for automatically producing or editing a script for a dramatic production.

A computing apparatus may be configured to perform the method 1900. FIG. 13 shows components of an apparatus or system 1300 for generating a script or a portion of a script. The apparatus or system 1300 may include additional or more detailed components for performing functions or process operations as described herein. For example, the processor 1310 and memory 1316 may contain an instantiation of a process for randomizing one or more parameters of a cognitive appraisal model for simulated participants in a character interaction. As depicted, the apparatus or system 1300 may include functional blocks that can represent functions implemented by a processor, software, or combination thereof (e.g., firmware).

As illustrated in FIG. 13, the apparatus or system 1300 may comprise an electrical component 1302 for randomizing one or more parameters of a cognitive appraisal model for simulated participants in a character interaction. The component 1302 may be, or may include, a means for said randomizing. Said means may include the processor 1310 coupled to the memory 1316, and to an output of at least one biometric sensor 1314, the processor executing an algorithm based on program instructions stored in the memory. Such algorithm may include, for example, developing a table of outcomes for character interaction based on a personality interaction model, identifying a set of outcomes for two or more characters entering an interaction, generating a random number, and selecting one of set of outcomes based on the random number.

The apparatus 1300 may further include an electrical component 1304 for generating a plurality of scripts at least in part by modeling the character interactions while varying the parameters between different ones of the scripts. The component 1304 may be, or may include, a means for said generating. Said means may include the processor 1310 coupled to the memory 1316, the processor executing an algorithm based on program instructions stored in the memory. Such algorithm may include a sequence of more detailed operations, for example, randomly selecting a story arc and characters for a script, configuring simulated personalities for the characters, and generating a sequence of outcomes for the characters along the selected story arc.

The apparatus 1300 may further include an electrical component 1306 for estimating a measure of effectiveness based on one or more targeted story arcs based on the cognitive appraisal model for neuro-physiological response, for each of the plurality of scripts. The cognitive appraisal model predicts an audience response by correlating known or estimated neurological and cognitive characteristics of the target audience with a likelihood of a neuro-physiological response. The component 1306 may be, or may include, a means for said estimating. Said means may include the processor 1310 coupled to the memory 1316, the processor executing an algorithm based on program instructions stored in the memory. Such algorithm may include a sequence of more detailed operations, for example, building an audience profile characterized by an aggregate of the cognitive appraisal model, and generating an estimated aggregate audience response for each draft script by generating estimated individual responses using a valence-arousal model or other suitable model, and averaging the individual responses.

The apparatus 1300 may further include an electrical component 1308 for recording the estimated level of effectiveness in association with each of the draft scripts. The component 1308 may be, or may include, a means for said recording. Said means may include the processor 1310 coupled to the memory 1316, the processor executing an algorithm based on program instructions stored in the memory. Such algorithm may include a sequence of more detailed operations, for example, writing the estimated effectiveness in a computer database. Stored estimates can be used by creative producers for further content development or editing.

The apparatus 1300 may optionally include a processor module 1310 having at least one processor. The processor 1310 may be in operative communication with the modules 1302-1308 via a bus 1313 or similar communication coupling. In the alternative, one or more of the modules may be instantiated as functional modules in a memory of the processor. The processor 1310 may initiate and schedule the processes or functions performed by electrical components 1302-1308.

In related aspects, the apparatus 1300 may include a network interface module 1312 or equivalent I/O port operable for communicating with system components over a computer network. A network interface module may be, or may include, for example, an Ethernet port or serial port (e.g., a Universal Serial Bus (USB) port), a Wi-Fi interface, or a cellular telephone interface. In further related aspects, the apparatus 1300 may optionally include a module for storing information, such as, for example, a memory device 1316. The computer readable medium or the memory module 1316 may be operatively coupled to the other components of the apparatus 1300 via the bus 1313 or the like. The memory module 1316 may be adapted to store computer readable instructions and data for effecting the processes and behavior of the modules 1302-1308, and subcomponents thereof, or the processor 1310, or the method 1200. The memory module 1316 may retain instructions for executing functions associated with the modules 1302-1308. While shown as being external to the memory 1316, it is to be understood that the modules 1302-1308 can exist within the memory 1316 or an on-chip memory of the processor 1310.

Figure 14:
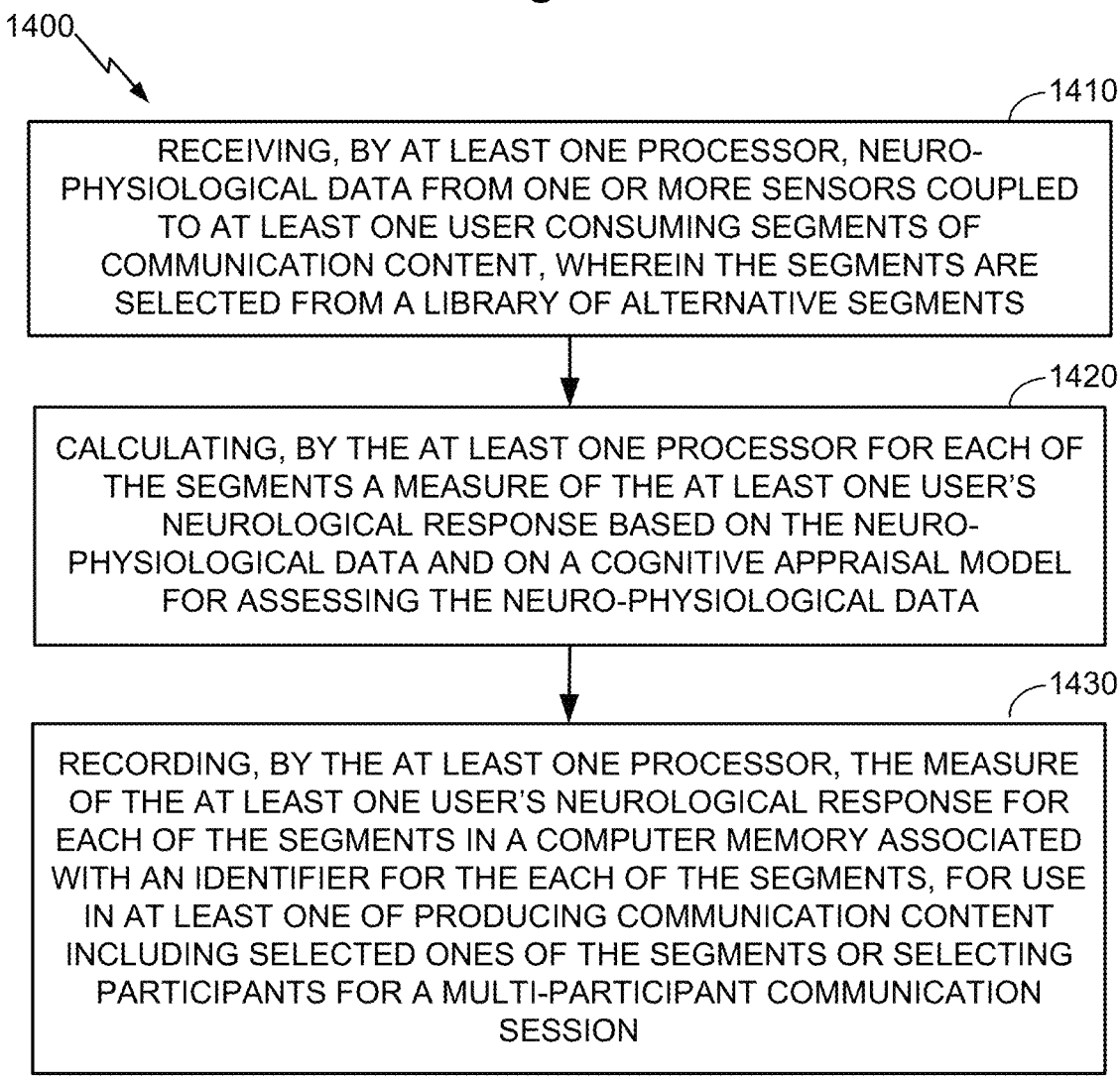
FIGS. 14 and 15 are flow charts illustrating aspects of a method for generating communication content.

Referring to FIG. 14, a computer-implemented method for generating communication content 1400 may include, at 1410, receiving, by at least one processor, neuro-physiological data from one or more sensors coupled to at least one user consuming segments of communication content, wherein the segments are selected from a library of alternative segments. The communication content may be encoded for a mobile device, for example, a portable flat screen device, a digital projector, or wearable gear, some or all of which may be used for alternative reality or augmented reality, in each case optionally coupled to an audio output capability and optionally to other output capabilities (e.g., motion, tactile, or olfactory). Playing the communication content may include, for example, keeping the communication content in a cache or other memory of the mobile device and processing the content for output by at least one processor of the mobile device. The communication content may include entertainment, social interaction, and information/education content, or other content.

The method 1400 may include, at 1420, calculating, by the at least one processor, and for each of the segments, a measure of the at least one user's neurological response based on the neuro-physiological data and on a cognitive appraisal model for assessing the neuro-physiological data. For example, the calculating may include determining a Content Engagement Power (CEP) value for the each of the segments the neuro-physiological data may include any one or more of the data described herein for arousal, valence, or other measures. For example, the neuro-physiological data may include one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (fMRI) data, and functional near-infrared data (fNIR). In an aspect, determining the CEP value may further include determining arousal values based on the neuro-physiological data and comparing a stimulation average arousal based on the neuro-physiological data with an expectation average arousal. In an aspect, the measure of the at least one user's neurological response for each of the segments includes at least one indication of valance.

The method 1400 may include at 1430 recording, by the at least one processor, the measure of the at least one user's neurological response for each of the segments in a computer memory associated with an identifier for the each of the segments, for use in at least one of producing communication content including selected ones of the segments or selecting participants for a multi-participant communication session.

Figure 15:
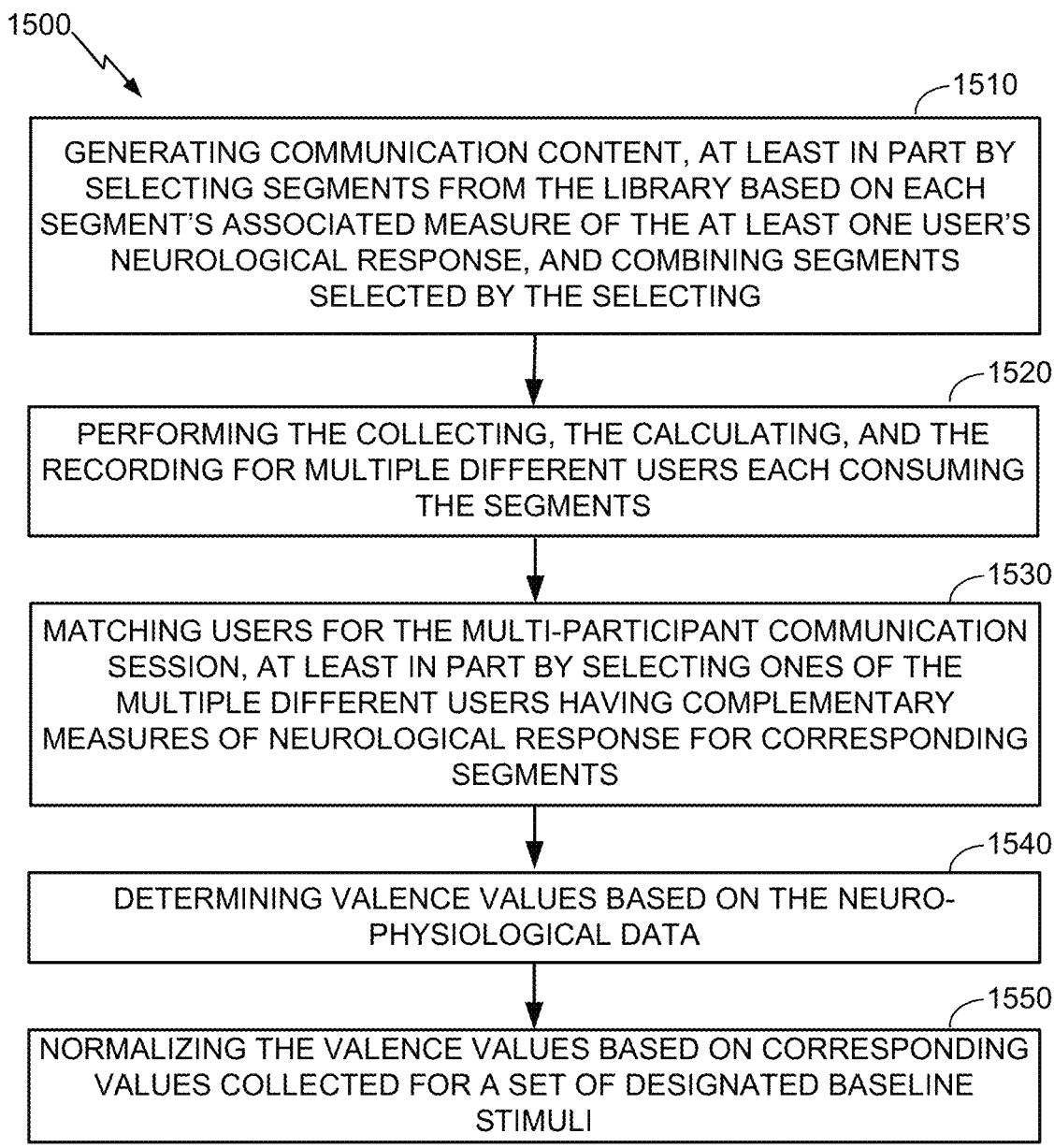

FIG. 15 lists additional operations 1500 that may be performed as part of the method 1400. The elements of the operation 1500 may be performed in any operative order, and any one or any number of them may be omitted from the method 1400.

Referring to FIG. 15, the method 1400 may include any one or more of the additional operations 1500 for generating communication content. The method 1400 may include, at 1510 generating communication content, at least in part by selecting segments from the library based on each segment's associated measure of the at least one user's neurological response, and combining segments selected by the selecting. In an aspect, the selecting may further include assigning an error indicator to each segment's associated measure of the at least one user's neurological response, based on a difference between the associated measure and a target value. For example, in an aspect, the selecting may include minimizing segments having an assigned error indicator.

The method 1400 may include, at 1520, performing the collecting, the calculating, and the recording for multiple different users each consuming the segments. In an aspect, the segments may consist essentially of linguistic content. In another aspect, the segments may consist essentially of audio content.

In another aspect, the method 1400 may include, at 1530 matching users for the multi-participant communication session, at least in part by selecting ones of the multiple different users having complementary measures of neurological response for corresponding segments. For example, in an aspect, the multi-participant communication session may include one or more of a computer game or a social chat session.

The method 1400 may include, at 1540 determining valence values based on the neuro-physiological data. The method 1400 may include, at 1550 normalizing the valence values based on corresponding values collected for a set of designated baseline stimuli.

Figure 16:
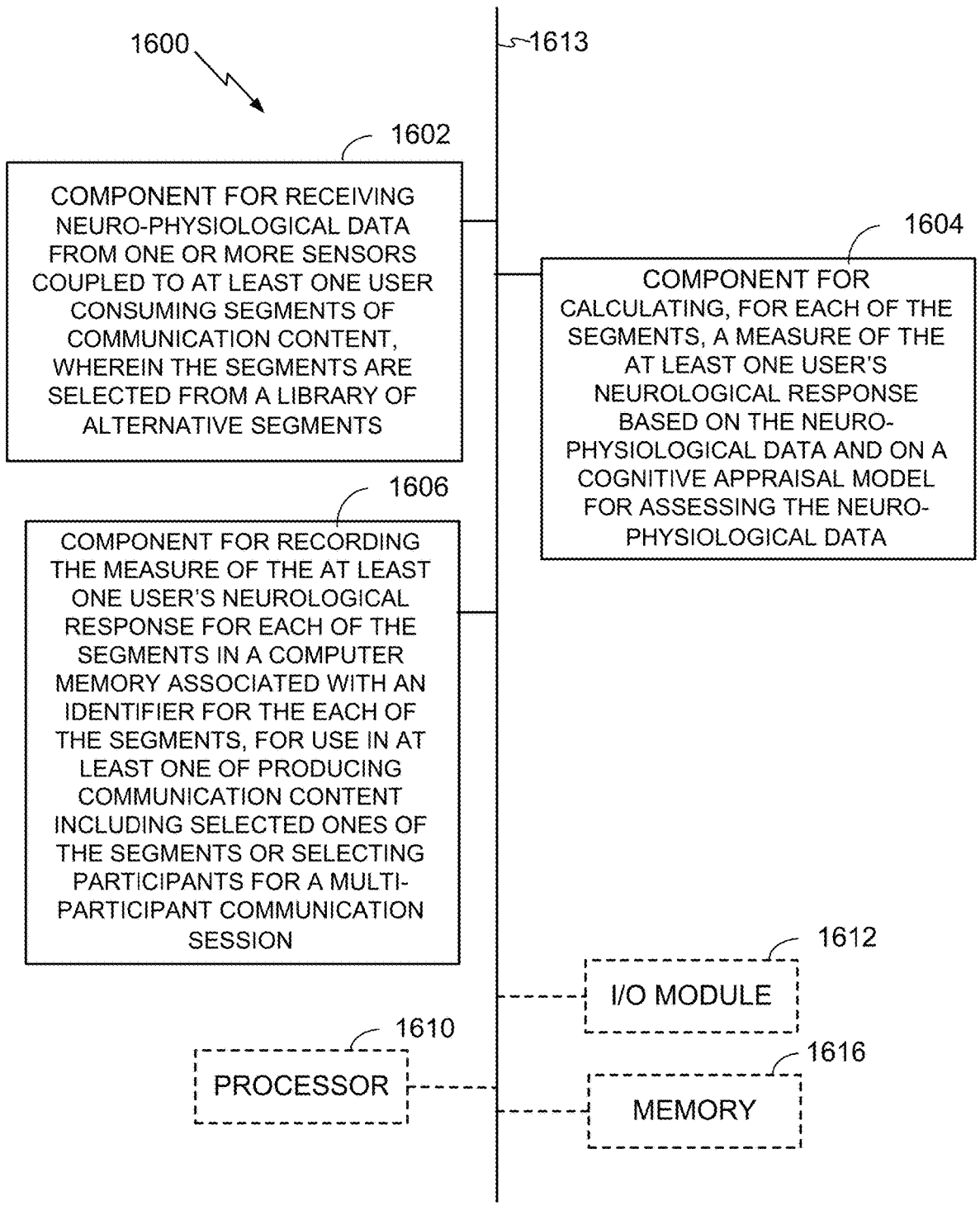
FIG. 16 is a conceptual block diagram illustrating components of an apparatus or system for generating communication content.

FIG. 16 is a conceptual block diagram illustrating components of an apparatus or system 1600 for generating communication content. The apparatus or system 1600 may include additional or more detailed components for performing functions or process operations as described herein. For example, the processor 1610 and memory 1616 may contain an instantiation of a process for calculating CEP in real time as described herein above. As depicted, the apparatus or system 1600 may include functional blocks that can represent functions implemented by a processor, software, or combination thereof (e.g., firmware).

As illustrated in FIG. 16, the apparatus or system 1600 may comprise an electrical component 1602 for receiving neuro-physiological data from one or more sensors coupled to at least one user consuming segments of communication content, wherein the segments are selected from a library of alternative segments. The component 1602 may be, or may include, a means for said receiving. Said means may include the processor 1610 coupled to the memory 1616, and to an output of at least one sensor 1614, such as the neuro-physiological sensors described elsewhere herein, the processor executing an algorithm based on program instructions stored in the memory. Such algorithm may include a sequence of more detailed operations, for example, configuring a data port to receive sensor data from a known sensor, configuring a connection to the sensor, receiving digital data at the port, and interpreting the digital data as sensor data.

The apparatus 1600 may further include an electrical component 1604 for calculating, for each of the segments, a measure of the at least one user's neurological response based on the neuro-physiological data and on a cognitive appraisal model for assessing the neuro-physiological data. The component 1604 may be, or may include, a means for said calculating. Said means may include the processor 1610 coupled to the memory 1616, the processor executing an algorithm based on program instructions stored in the memory. Such algorithm may include a sequence of more detailed operations, for example, as described in connection with FIG. 8.

The apparatus 1600 may further include an electrical component 1606 for recording the measure of the at least one user's neurological response for each of the segments in a computer memory associated with an identifier for the each of the segments, for use in at least one of producing communication content including selected ones of the segments or selecting participants for a multi-participant communication session. The component 1608 may be, or may include, a means for said recording. Said means may include the processor 1610 coupled to the memory 1616, the processor executing an algorithm based on program instructions stored in the memory. Such algorithm may include a sequence of more detailed operations, for example, encoding the measure of the at least one user's neurological response and storing the encoded measure in a computer memory.

The apparatus 1600 may optionally include a processor module 1610 having at least one processor. The processor 1610 may be in operative communication with the modules 1602-1608 via a bus 1613 or similar communication coupling. In the alternative, one or more of the modules may be instantiated as functional modules in a memory of the processor. The processor 1610 may initiate and schedule the processes or functions performed by electrical components 1602-1608.

In related aspects, the apparatus 1600 may include a network interface module 1612 or equivalent I/O port operable for communicating with system components over a computer network. A network interface module may be, or may include, for example, an Ethernet port or serial port (e.g., a Universal Serial Bus (USB) port), a Wi-Fi interface, or a cellular telephone interface. In further related aspects, the apparatus 1600 may optionally include a module for storing information, such as, for example, a memory device 1616. The computer readable medium or the memory module 1616 may be operatively coupled to the other components of the apparatus 1600 via the bus 1613 or the like. The memory module 1616 may be adapted to store computer readable instructions and data for effecting the processes and behavior of the modules 1602-1606, and subcomponents thereof, or the processor 1610, the method 1400 and one or more of the additional operations 1500 disclosed herein, or any method for performance by a media player described herein. The memory module 1616 may retain instructions for executing functions associated with the modules 1602-1608. While shown as being external to the memory 1616, it is to be understood that the modules 1602-1606 can exist within the memory 1616 or an on-chip memory of the processor 1610.

The apparatus 1600 may include, or may be connected to, one or more sensors 1614, which may be of any suitable types. Various examples of suitable sensors are described herein above. In alternative embodiments, the processor 1610 may include networked microprocessors from devices operating over a computer network. In addition, the apparatus 1600 may connect to an output device as described herein, via the I/O module 1612 or other output port.

Figure 17:
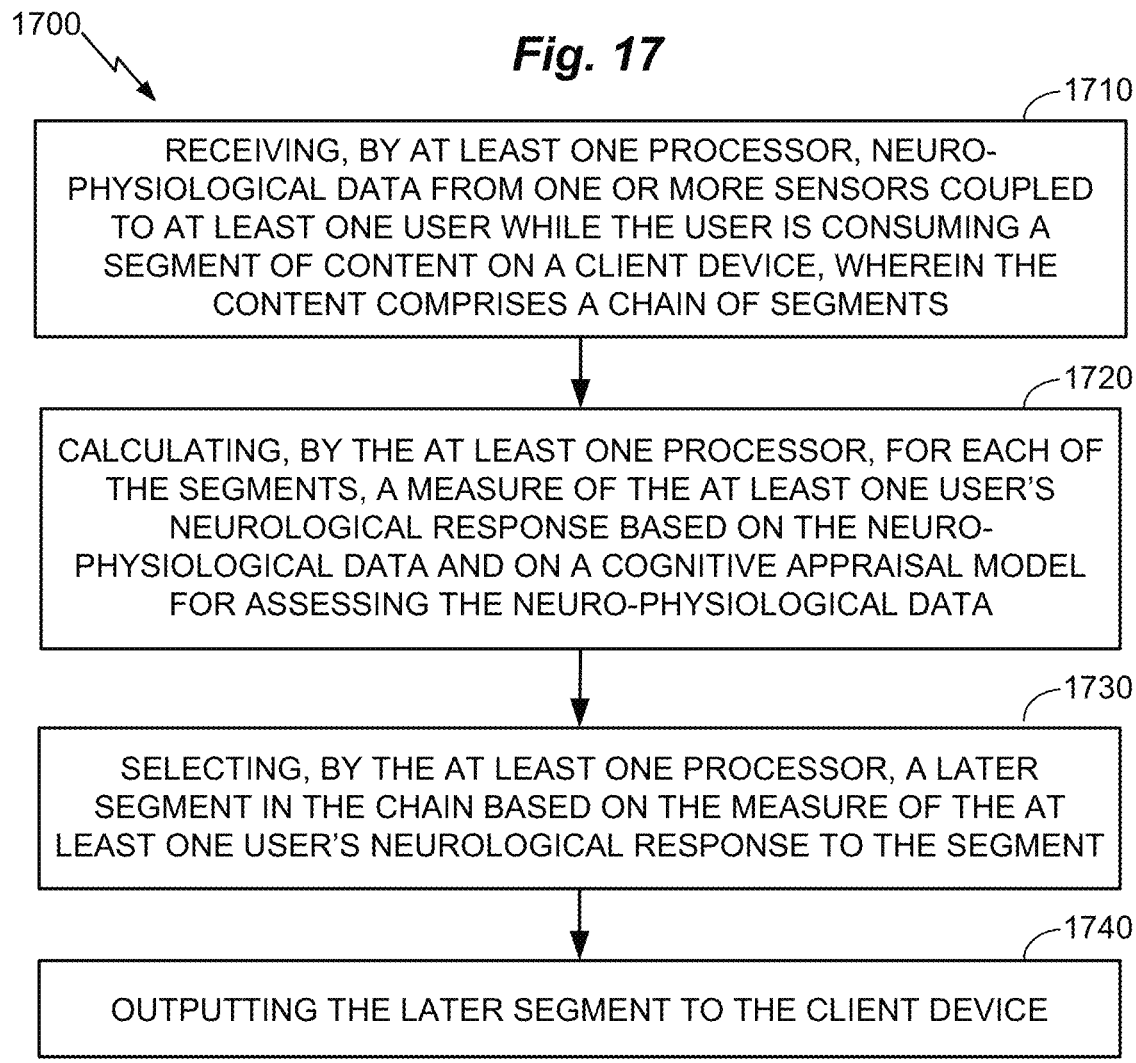
FIGS. 17 and 18 are flow charts illustrating aspects of a method for controlling presentation of communication content.

Referring to FIG. 17, a computer-implemented method for controlling presentation of communication content 1700 may include, at 1710, receiving, by at least one processor, neuro-physiological data from one or more sensors coupled to at least one user while the user is consuming a segment of content on a client device, wherein the content comprises a chain of segments. The content may be encoded for a mobile device, for example, a portable flat screen device, a digital projector, or wearable gear, some or all of which may be used for alternative reality or augmented reality, in each case optionally coupled to an audio output capability and optionally to other output capabilities (e.g., motion, tactile, or olfactory). Playing the content may include, for example, keeping the content in a cache or other memory of the mobile device and processing the content for output by at least one processor of the mobile device. The content may include communication, entertainment, social interaction, and information/education content, or other content. The segments may include, for example, content selected from the group consisting of linguistic content, audio content, and audio-video content.

The method 1700 may include, at 1720, calculating, by the at least one processor, and for each of the segments, a measure of the at least one user's neurological response based on the neuro-physiological data and on a cognitive appraisal model for assessing the neuro-physiological data. For example, the calculating may include determining a Content Engagement Power (CEP) value for the each of the segments the neuro-physiological data may include any one or more of the data described herein for arousal, valence, or other measures. For example, the neuro-physiological data may include one or more of electroencephalographic (EEG)

data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (fMRI) data, and functional near-infrared data (fNIR). In an aspect, determining the CEP value may further include determining arousal values based on the neuro-physiological data and comparing a stimulation average arousal based on the neuro-physiological data with an expectation average arousal. In an aspect, the measure of the at least one user's neurological response for each of the segments includes at least one indication of valance.

The method 1700 may include at 1730 selecting, by the at least one processor, a later segment in the chain based on the measure of the at least one user's neurological response to the segment. In an aspect, the selecting further includes determining an error indicator for each segment's associated measure of the at least one user's neurological response, based on a difference between the associated measure and a target value. In another aspect, the selecting includes minimizing segments having an assigned error indicator.

The method may include at 1740 outputting the later segment to the client device.

Figure 18:
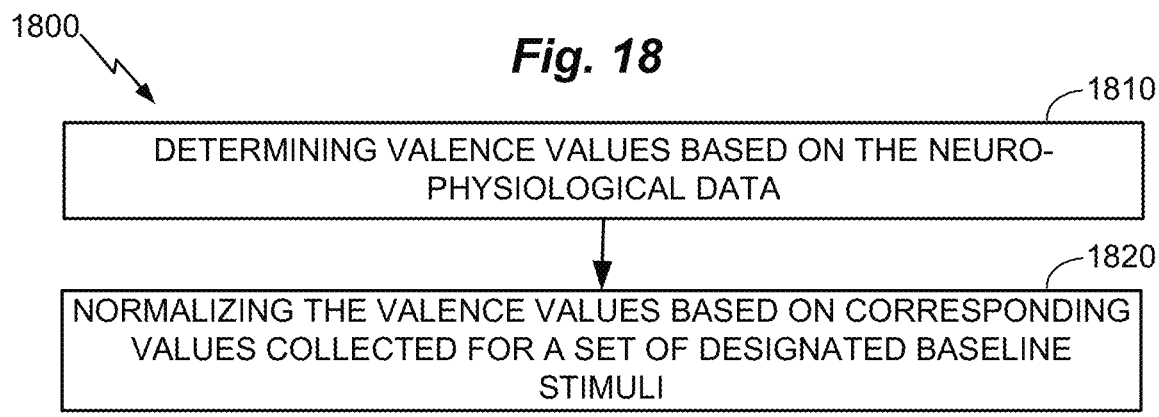

FIG. 18 lists additional operations 1800 that may be performed as part of the method 1700. The elements of the operation 1800 may be performed in any operative order, and any one or any number of them may be omitted from the method 1700.

Referring to FIG. 18, the method 1700 may include any one or more of the additional operations 1500 for controlling presentation of content. The method 1700 may include, at 1810 determining valence values based on the neuro-physiological data. In an aspect, the neuro-physiological data may include one or more of electroencephalographic (EEG) data, facial electromyography (fEMG) data, video facial action unit (FAU) data, brain machine interface (BMI) data, functional magnetic resonance imaging (fMRI) data, and functional near-infrared data (fNIR).

The method 1700 may include, at 1820, normalizing the valence values based on corresponding values collected for a set of designated baseline stimuli. In an aspect, the segments may consist essentially of linguistic content. In another aspect, the segments may consist essentially of audio content.

Figure 19:
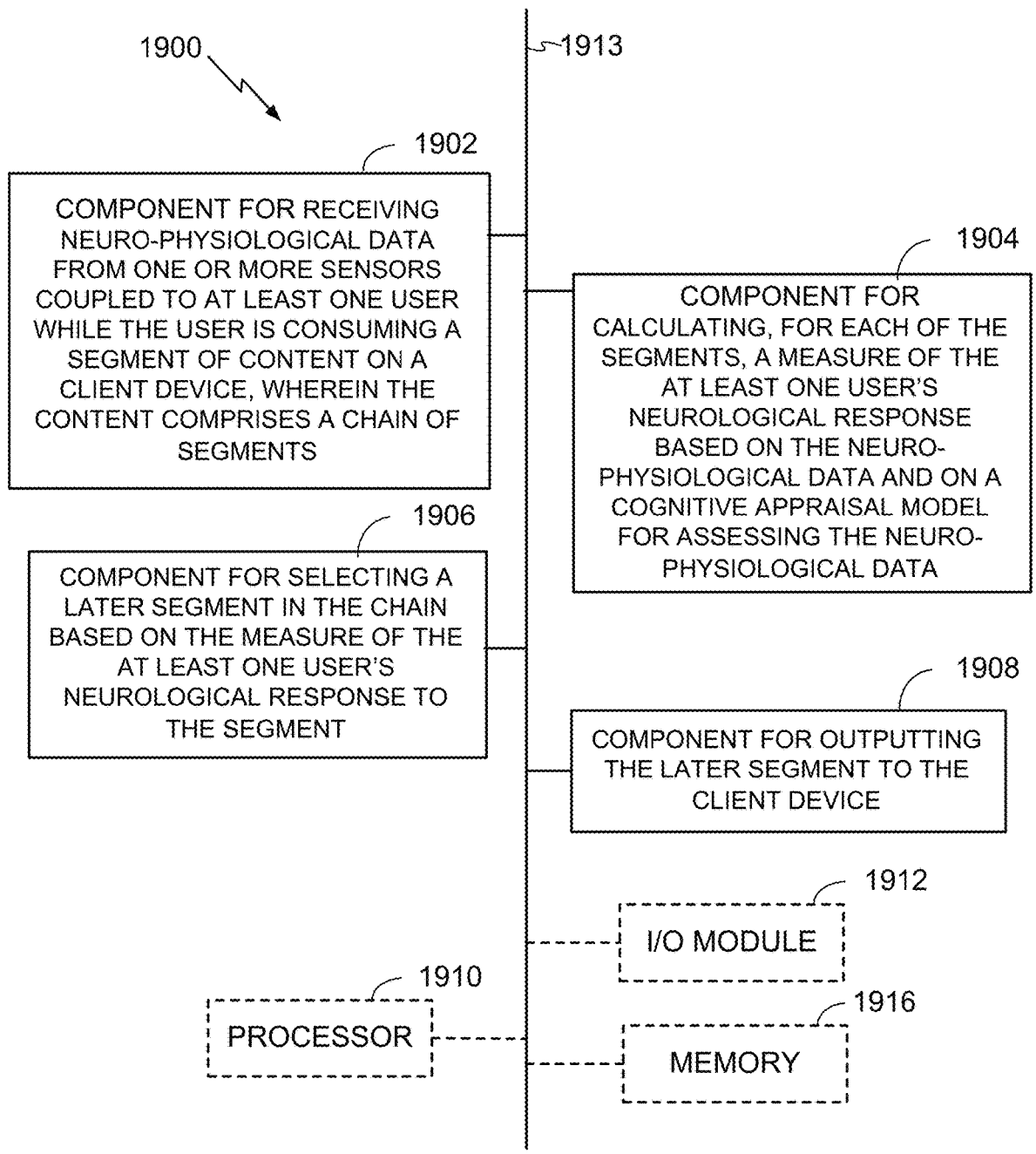
FIG. 19 is a conceptual block diagram illustrating components of an apparatus or system for controlling presentation of content.

FIG. 19 is a conceptual block diagram illustrating components of an apparatus or system 1700 for controlling presentation of content. The apparatus or system 1900 may include additional or more detailed components for performing functions or process operations as described herein. For example, the processor 1910 and memory 1916 may contain an instantiation of a process for calculating CEP in real time as described herein above. As depicted, the apparatus or system 1900 may include functional blocks that can represent functions implemented by a processor, software, or combination thereof (e.g., firmware).

As illustrated in FIG. 19, the apparatus or system 1900 may comprise an electrical component 1902 for receiving neuro-physiological data from one or more sensors coupled to at least one user while the user is consuming a segment of content on a client device, wherein the content comprises a chain of segments. The component 1902 may be, or may include, a means for said receiving. Said means may include the processor 1910 coupled to the memory 1916, and to an output of at least one sensor 1914, such as the neuro-physiological sensors described elsewhere herein, the processor executing an algorithm based on program instructions stored in the memory. Such algorithm may include a sequence of more detailed operations, for example, configuring a data port to receive sensor data from a known sensor, configuring a connection to the sensor, receiving digital data at the port, and interpreting the digital data as sensor data.

The apparatus 1900 may further include an electrical component 1904 for calculating, for each of the segments, a measure of the at least one user's neurological response based on the neuro-physiological data and on a cognitive appraisal model for assessing the neuro-physiological data. The component 1904 may be, or may include, a means for said calculating. Said means may include the processor 1910 coupled to the memory 1916, the processor executing an algorithm based on program instructions stored in the memory. Such algorithm may include a sequence of more detailed operations, for example, as described in connection with FIG. 8.

The apparatus 1900 may further include an electrical component 1906 for selecting a later segment in the chain based on the measure of the at least one user's neurological response to the segment. The component 1908 may be, or may include, a means for said selecting. Said means may include the processor 1910 coupled to the memory 1916, the processor executing an algorithm based on program instructions stored in the memory. Such algorithm may include a sequence of more detailed operations, for example, selecting a later segment in the chain having a CEP value that is different from (e.g., higher or lower than) the measure of the at least one user's neurological response.

The apparatus 1900 may further include an electrical component 1908 for outputting the later segment to the client device. The component 1908 may be, or may include, a means for said outputting. Said means may include the processor 1910 coupled to the memory 1916, the processor executing an algorithm based on program instructions stored in the memory. Such algorithm may include a sequence of more detailed operations, for example, sending the later segment to a client device for presentation to a user, where the presentation may be done via visual, audio, text, video, or other form perceivable or recognizable by the user.

The apparatus 1900 may optionally include a processor module 1910 having at least one processor. The processor 1910 may be in operative communication with the modules 1902-1908 via a bus 1913 or similar communication coupling. In the alternative, one or more of the modules may be instantiated as functional modules in a memory of the processor. The processor 1910 may initiate and schedule the processes or functions performed by electrical components 1902-1908.

In related aspects, the apparatus 1900 may include a network interface module 1912 or equivalent I/O port operable for communicating with system components over a computer network. A network interface module may be, or may include, for example, an Ethernet port or serial port (e.g., a Universal Serial Bus (USB) port), a Wi-Fi interface, or a cellular telephone interface. In further related aspects, the apparatus 1900 may optionally include a module for storing information, such as, for example, a memory device 1916. The computer readable medium or the memory module 1916 may be operatively coupled to the other components of the apparatus 1900 via the bus 1913 or the like. The memory module 1916 may be adapted to store computer readable instructions and data for effecting the processes and behavior of the modules 1902-1908, and subcomponents thereof, or the processor 1910, the method 1700 and one or more of the additional operations 1800 disclosed herein, or any method for performance by a client device described herein. The memory module 1916 may retain instructions for executing functions associated with the modules 1902-1908. While shown as being external to the memory 1916, it is to be understood that the modules 1902-1908 can exist within the memory 1916 or an on-chip memory of the processor 1910.

The apparatus 1900 may include, or may be connected to, one or more sensors 1914, which may be of any suitable types. Various examples of suitable sensors are described herein above. In alternative embodiments, the processor 1910 may include networked microprocessors from devices operating over a computer network. In addition, the apparatus 1900 may connect to an output device as described herein, via the I/O module 1912 or other output port.

Figure 20:
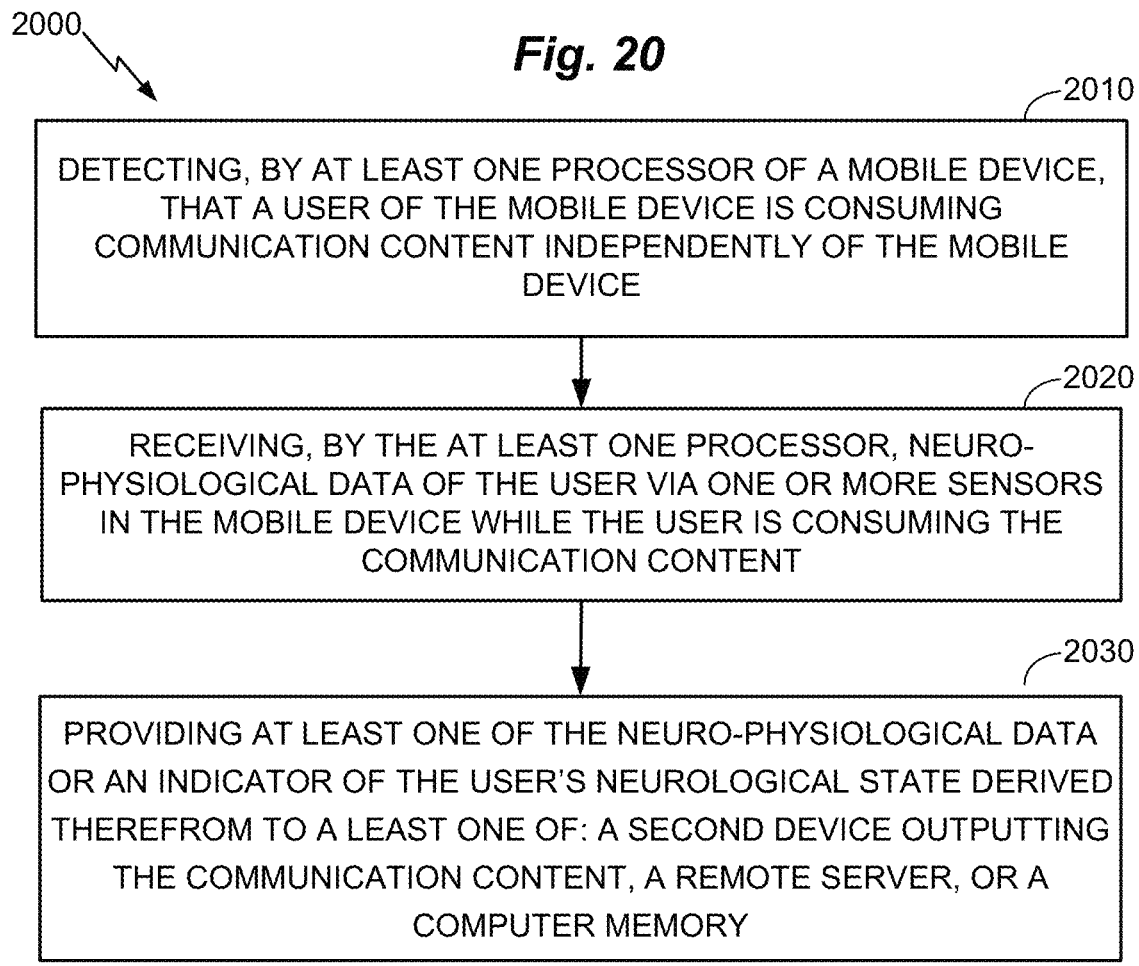
FIGS. 20 and 21 are flow charts illustrating aspects of a method for collecting neuro-physiological data indicating a neurological response of a user consuming communication content.

Referring to FIG. 20, a computer-implemented method for collecting neuro-physiological data indicating a neurological response of a user consuming communication content 2000 may be executed using systems and apparatus as described in connection with FIGS. 9-11. The method 2000 may include, at 2010, detecting, by at least one processor of a mobile device, that a user of the mobile device is consuming communication content independently of the mobile device. The communication content may be encoded for a mobile device, for example, a portable flat screen device, a digital projector, or wearable gear, some or all of which may be used for alternative reality or augmented reality, in each case optionally coupled to an audio output capability and optionally to other output capabilities (e.g., motion, tactile, or olfactory). In one implementation, the mobile device includes a wrist-worn smart device. In other aspects, the mobile device may include one or more of other smart devices or wearable devices, for example, a headgear, a finger-worn device, a goggle, etc. Playing the communication content may include, for example, keeping the communication content in a cache or other memory of the mobile device and processing the content for output by at least one processor of the mobile device. The communication content may include entertainment, social interaction, and information/education content, or other content.

The method 2000 may include, at 2020, receiving, by the at least one processor, neuro-physiological data of the user via one or more sensors in the mobile device while the user is consuming the communication content. For example, the receiving may be via at least one sensor of the mobile device comprising a microphone, a camera, an infrared sensor, or a phased-array sensor, or a galvanic skin response sensor. In an aspect, the one or more sensors may be used to obtain neuro-physiological data useful in determining a Content Engagement Power (CEP) value for the communication content The neuro-physiological data may include any one or more of the data described herein for arousal, valence, or other measures. For example, the neuro-physiological data may include one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (fMRI) data, and functional near-infrared data (fNIR).

The method 2000 may include at 2030 providing at least one of the neuro-physiological data or an indicator of the user's neurological state derived therefrom to a least one of: a second device outputting the communication content, a remote server, or a computer memory. In an aspect, the mobile device coordinates a handoff of a play session of the communication content from the second device to a third device. In an aspect, the mobile device does not communicate with the second device. In an aspect, the at least one processor of the mobile device outputs a user-perceivable signal to attract at least one of a gaze, a touch, speech or a gesture at a time synchronized with play of the communication content.

Figure 21:
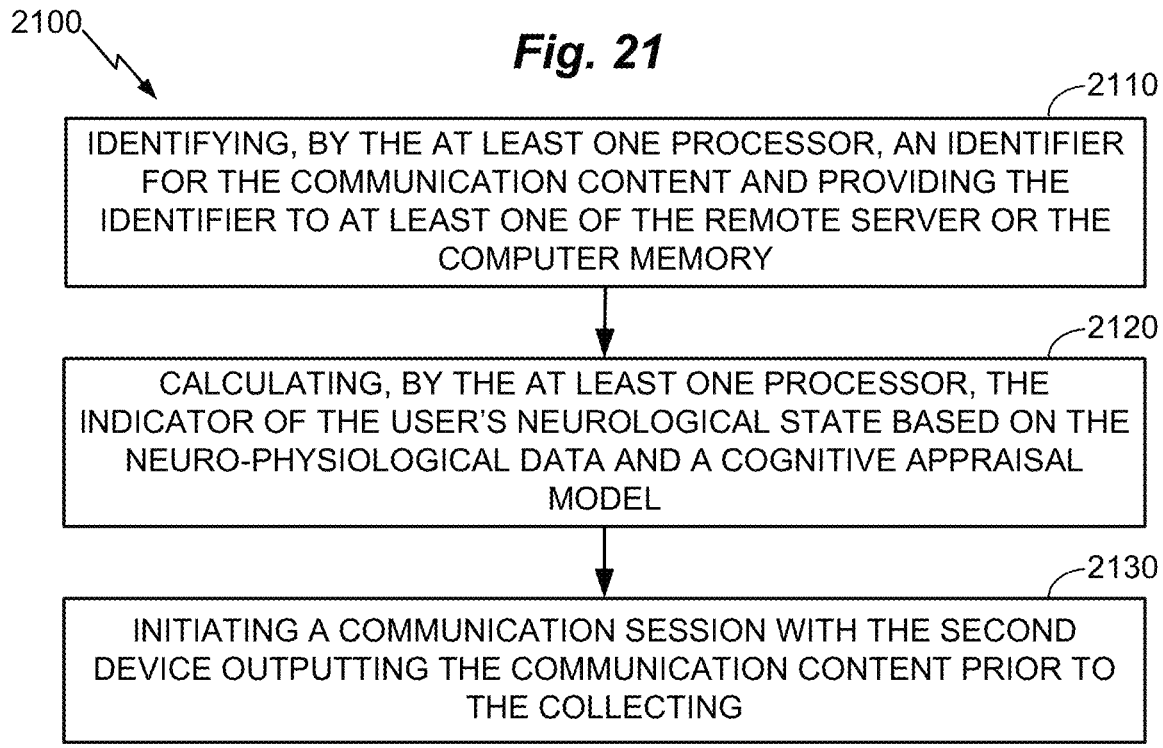

FIG. 21 list additional operations 2100 that may be performed as part of the method 2000. The elements of the operation 2100 may be performed in any operative order, and any one or any number of them may be omitted from the method 2000.

Referring to FIG. 21, the method 2000 may include any one or more of the additional operations 2100 for collecting neuro-physiological data indicating a neurological response of a user consuming communication content. The method 2000 may include, at 2110 identifying, by the at least one processor, an identifier for the communication content and providing the identifier to at least one of the remote server or the computer memory.

The method 2000 may include, at 2120, calculating, by the at least one processor, the indicator of the user's neurological state based on the neuro-physiological data and a cognitive appraisal model. For example, the calculating may include determining a Content Engagement Power (CEP) value for the each of the segments the neuro-physiological data may include any one or more of the data described herein for arousal, valence, or other measures. For example, the neuro-physiological data may include one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (fMRI) data, and functional near-infrared data (fNIR). In an aspect, determining the CEP value may further include determining arousal values based on the neuro-physiological data and comparing a stimulation average arousal based on the neuro-physiological data with an expectation average arousal. In an aspect, the measure of the at least one user's neurological response for each of the segments includes at least one indication of valance. In an aspect, the content may consist essentially of linguistic content. In another aspect, the content may consist essentially of audio content.

In another aspect, the method 2000 may include, at 2130 initiating a communication session with the second device outputting the communication content prior to the collecting. For example, in an aspect, communication session may include one or more of a computer game or a social chat session.

Figure 22:
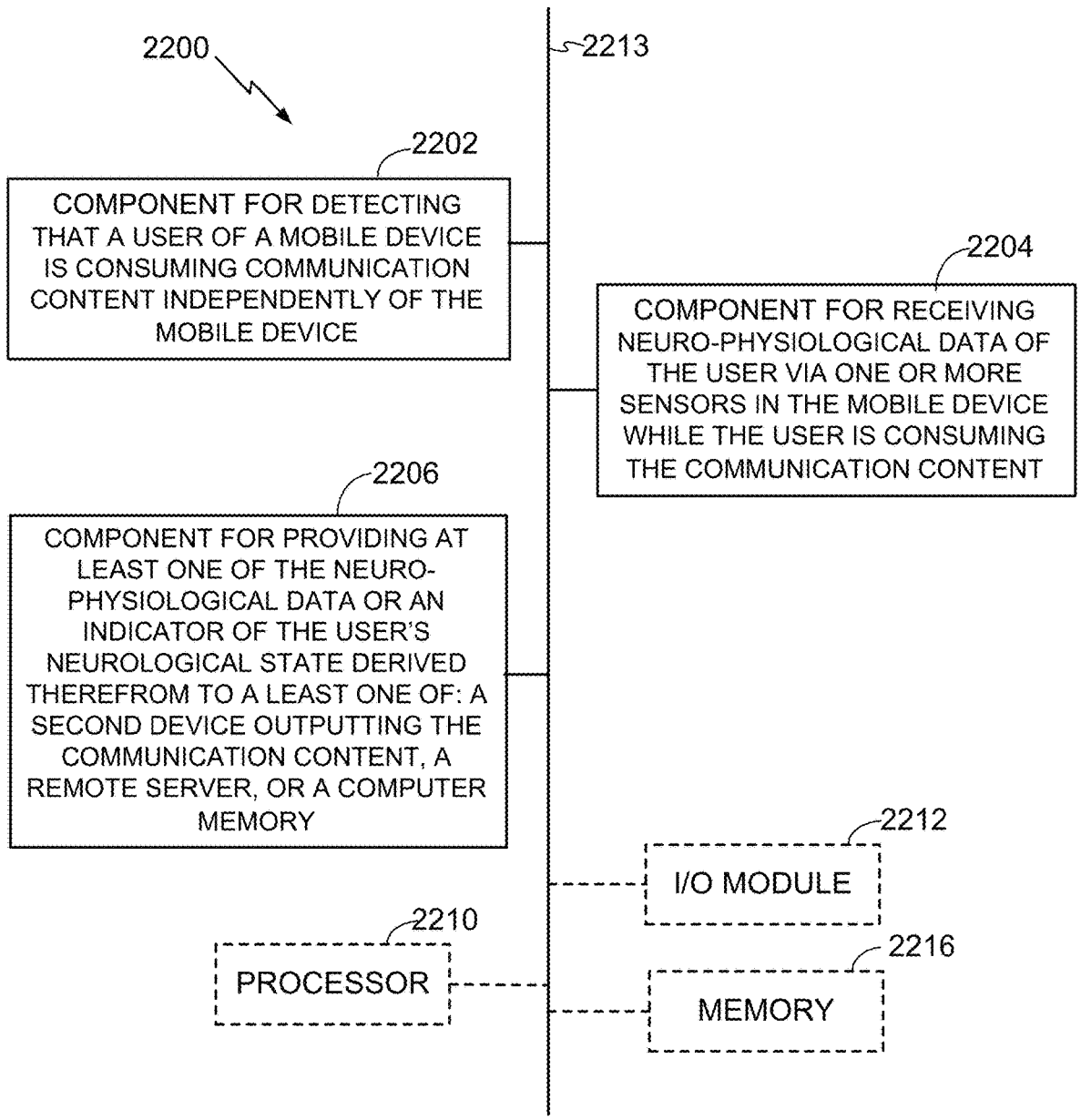
FIG. 22 is a conceptual block diagram illustrating components of an apparatus or system for collecting neuro-physiological data indicating a neurological response of a user consuming communication content.

FIG. 22 is a conceptual block diagram illustrating components of an apparatus or system 2200 for generating communication content. The apparatus or system 2200 may include additional or more detailed components for performing functions or process operations as described herein. For example, the processor 2210 and memory 2216 may contain an instantiation of a process for calculating CEP in real time as described herein above. As depicted, the apparatus or system 2200 may include functional blocks that can represent functions implemented by a processor, software, or combination thereof (e.g., firmware).

As illustrated in FIG. 22, the apparatus or system 2200 may comprise an electrical component 2202 for detecting that a user of a mobile device is consuming communication content independently of the mobile device. The component 2202 may be, or may include, a means for said detecting. Said means may include the processor 2210 coupled to the memory 2216, and to an output of at least one sensor 2214, such as the neuro-physiological sensors described elsewhere herein, the processor executing an algorithm based on program instructions stored in the memory. Such algorithm may include a sequence of more detailed operations, for example, configuring a data port to receive communication content data from a known device other than the mobile device, configuring a connection to the known device, receiving known device data at the port, and interpreting the known device data and communication content data.

The apparatus 2200 may further include an electrical component 2204 for receiving neuro-physiological data of the user via one or more sensors in the mobile device while the user is consuming the communication content. The component 2204 may be, or may include, a means for said receiving. Said means may include the processor 2210 coupled to the memory 2216, the processor executing an algorithm based on program instructions stored in the memory. Such algorithm may include a sequence of more detailed operations, for example, configuring a data port to receive sensor data from a known sensor, configuring a connection to the sensor, receiving digital data at the port, and interpreting the digital data as sensor data.

The apparatus 2200 may further include an electrical component 2206 for providing at least one of the neuro-physiological data or an indicator of the user's neurological state derived therefrom to a least one of: a second device outputting the communication content, a remote server, or a computer memory. The component 2206 may be, or may include, a means for said providing. Said means may include the processor 2210 coupled to the memory 2216, the processor executing an algorithm based on program instructions stored in the memory. Such algorithm may include a sequence of more detailed operations, for example, encoding the measure of the at least one user's neurological response and storing the encoded measure in a computer memory, or as described in connection with FIG. 8.

The apparatus 2200 may optionally include a processor module 2210 having at least one processor. The processor 2210 may be in operative communication with the modules 2202-2208 via a bus 2213 or similar communication coupling. In the alternative, one or more of the modules may be instantiated as functional modules in a memory of the processor. The processor 2210 may initiate and schedule the processes or functions performed by electrical components 2202-2208.

In related aspects, the apparatus 2200 may include a network interface module 2212 or equivalent I/O port operable for communicating with system components over a computer network. A network interface module may be, or may include, for example, an Ethernet port or serial port (e.g., a Universal Serial Bus (USB) port), a Wi-Fi interface, or a cellular telephone interface. In further related aspects, the apparatus 2200 may optionally include a module for storing information, such as, for example, a memory device 2216. The computer readable medium or the memory module 2216 may be operatively coupled to the other components of the apparatus 2200 via the bus 2213 or the like. The memory module 2216 may be adapted to store computer readable instructions and data for effecting the processes and behavior of the modules 2202-2208, and subcomponents thereof, or the processor 2210, the method 2000 and one or more of the additional operations 2100 disclosed herein, or any method for performance by a media player described herein. The memory module 2216 may retain instructions for executing functions associated with the modules 2202-2208. While shown as being external to the memory 2216, it is to be understood that the modules 2202-2208 can exist within the memory 2216 or an on-chip memory of the processor 2210.

The apparatus 2200 may include, or may be connected to, one or more sensors 2214, which may be of any suitable types. Various examples of suitable sensors are described herein above. In alternative embodiments, the processor 2210 may include networked microprocessors from devices operating over a computer network. In addition, the apparatus 2200 may connect to an output device as described herein, via the I/O module 2212 or other output port.

Figure 23:
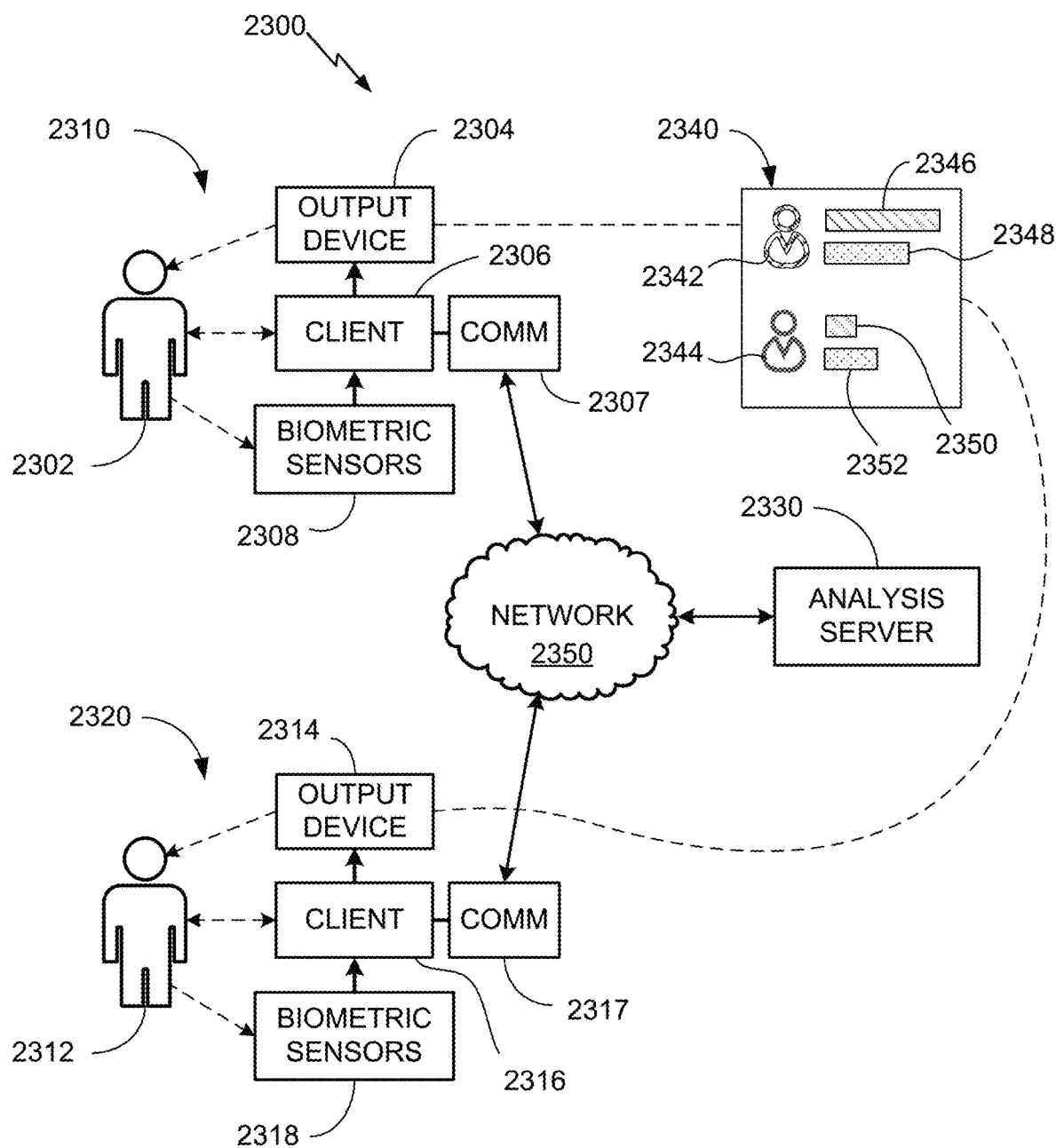
FIG. 23 is a diagram illustrating a system including mobile devices with sensors to enhance interpersonal communication with neuro-physiological tells.

The method and apparatus described herein may be adapted for improving person-to-person communication in virtual or real environments. FIG. 23 shows a system 2300 including a first node 2300 with a first person 2302 in communication with a second node 2320 with a second person 2312 via an electronic communication network 2350. The system 2300 may use a CEP model for communication where CEP values are presented and measured alongside a conversation. For example, the two people 2302, 2312 can converse while one or more of the participating clients 2306, 2316 present data 2340 on emotional affect alongside the photo or video 2342, 2344 of each participant. Neuro-physiological responses of the participants 2302, 2312 are sensed using corresponding biometric sensors 2308, 2318 and described elsewhere herein. Each client 2306, 2318 may convert sensor signals from the biometric sensors 2308, 2318 into biometric data and send the biometric data to an analysis server 2330 via respective communication components 2307, 2317 and a communication network 2350. The server 2330 may generate in real time or near real time one or more measures of valence, arousal, dominance, CEP or any other suitable measure of neuro-physiological response, and provide the one or more measures via the network 2350 to the clients 2306, 2316.

Each client 2306, 2316 may output the measures via output devices 2304, 2314, for example a display screen, as a graphical display 2340 or other useful format (e.g., audible output). The display 2340 or other output may report neurological state measures for conversation sequence statements or groups of statements. For example, a display 2340 may include an indication of arousal 2346, 2350 or valence 2348, 2352. The system 2300 may provide an alert any time there's a rapid increase in arousal and report the valence associated with the increase. The alert can then be appraised by the human for meaning. The system 2300 may be especially useful for human to human communication between players actors within a virtual immersive experience and may find application in other contexts also.

Figure 24:
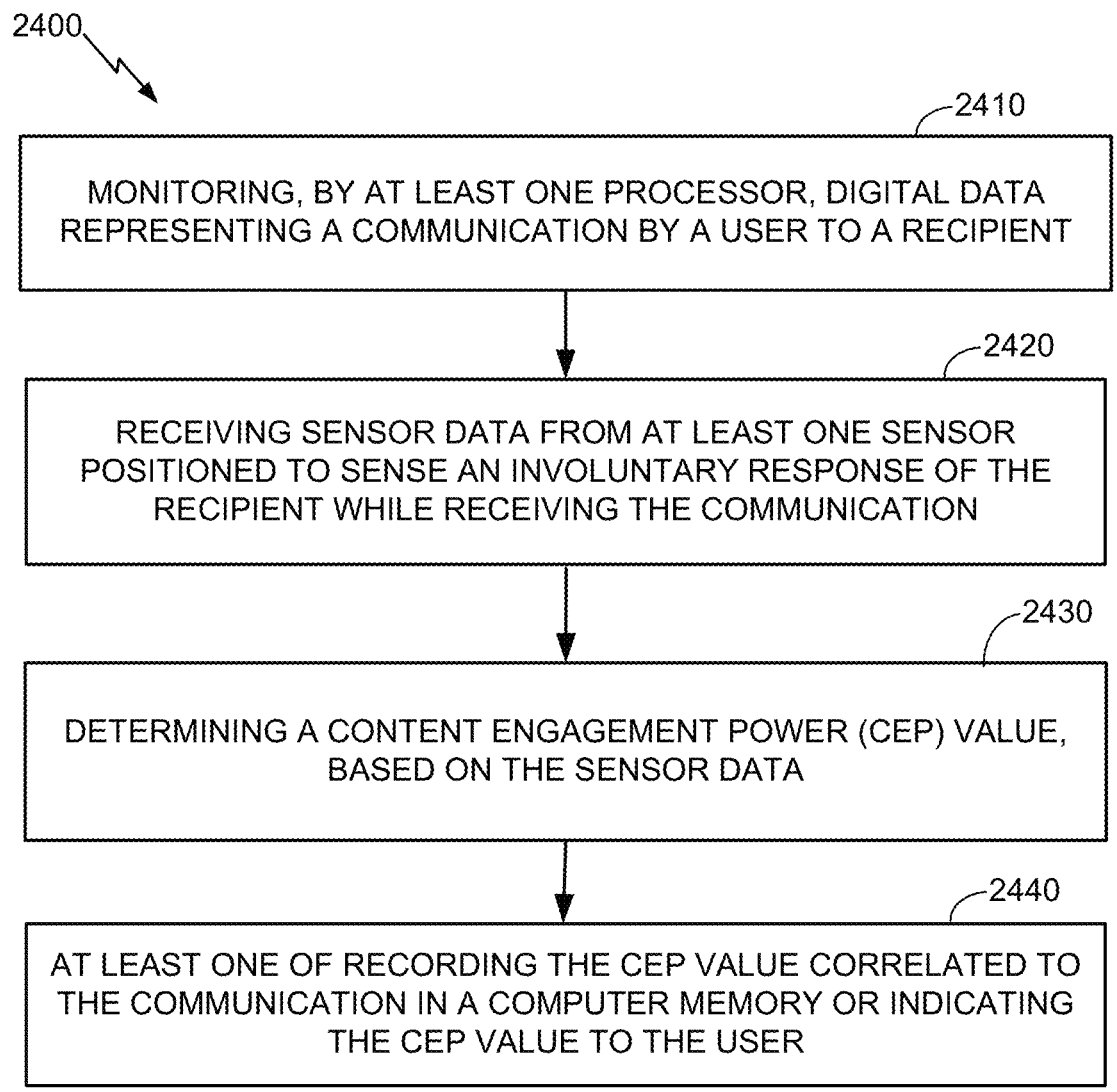
FIG. 24 is a flow chart illustrating aspects of a method for operating a system for enhancing interpersonal communication with neuro-physiological tells.
Figure 25:
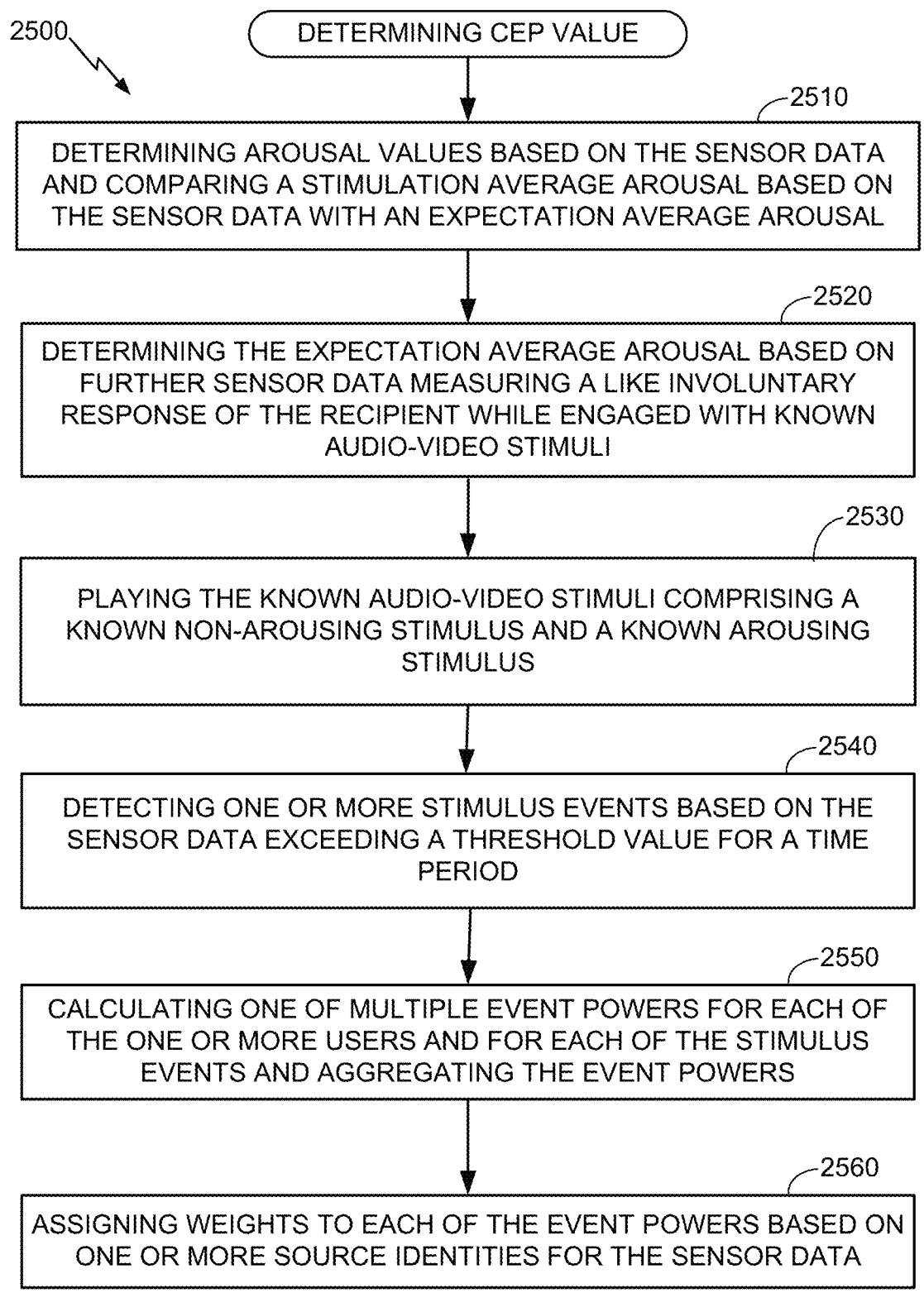
FIGS. 25-26 are flow charts illustrating optional further aspects or operations of the method diagrammed in FIG. 24.
Figure 26:
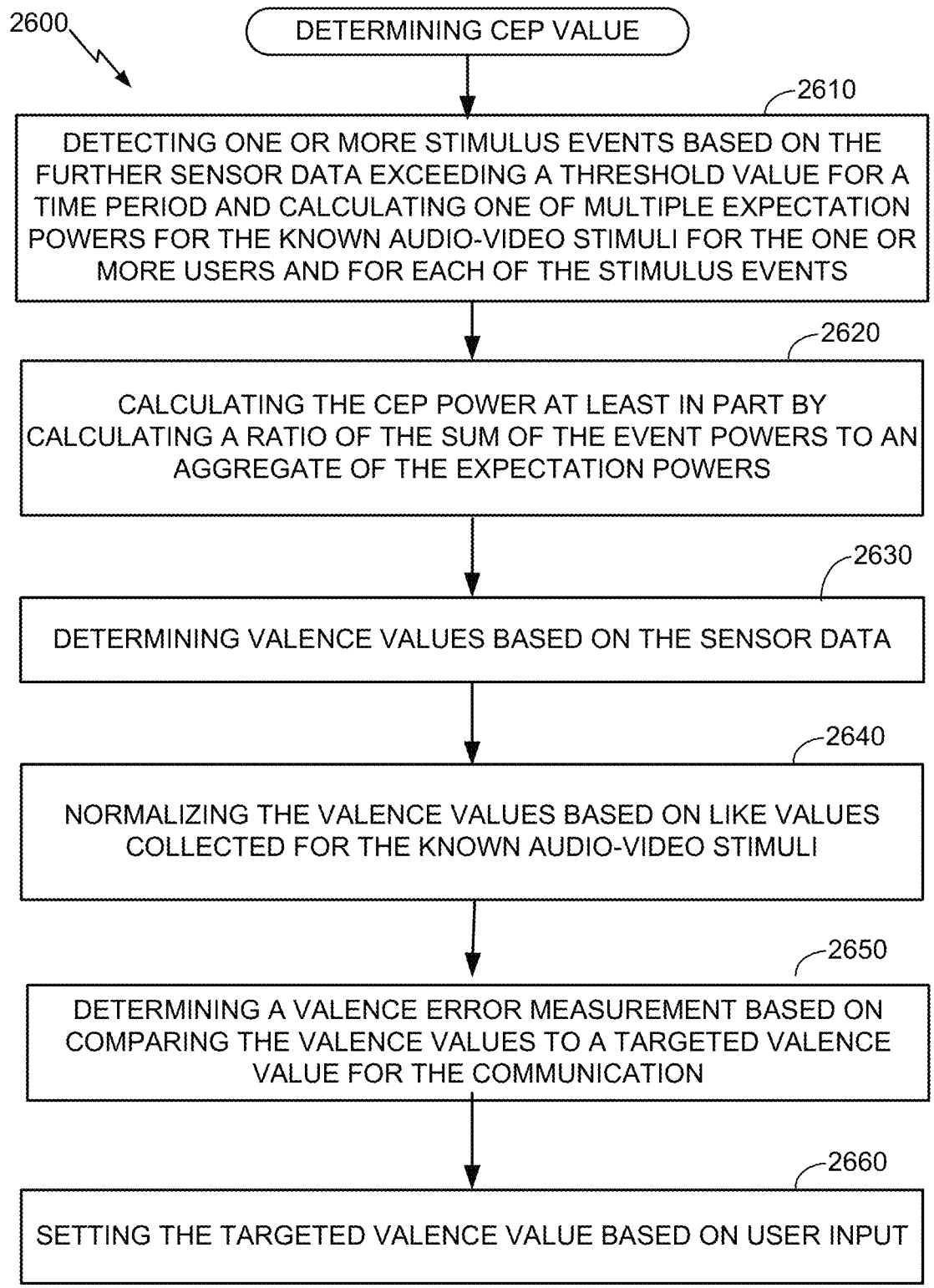

In view the foregoing, and by way of additional example, FIGS. 24-26 show aspects of a method 2400 or methods for rating effectiveness of personal communications. The method 2400 may be performed by an immersive mixed reality output device or a non-immersive flat screen device, projector, or other output device including a programmable computer, by one or more computers in communication with the output device, or by a combination of an output device and one or more computers in communication with the output device.

Referring to FIG. 24, a computer-implemented method for rating effectiveness of personal communications may include, at 2410, monitoring, by at least one processor, digital data representing a communication by a user to a recipient. The digital data may be encoded for an output device, for example, a portable or non-portable flat screen device, a digital projector, or wearable gear for alternative reality or augmented reality, in each case coupled to an audio output capability and optionally to other output capabilities (e.g., motion, tactile, or olfactory). Playing the digital data may include, for example, keeping the digital data in a cache or other memory of the output device and processing the data for output by at least one processor of the output device.

The method 2400 may include, at 2420, receiving sensor data from at least one sensor positioned to sense an involuntary response of the recipient while receiving the communication. The sensor data may include any one or more of the data described herein for arousal, valence, or other measures.

The method 2400 may include at 2430 determining a Content Engagement Power (CEP) value for the communication, based on the sensor data, using an algorithm as described herein above. In an alternative, the method may determine a different measure for neuro-physiological response. The method may include at 2440 recording the CEP value or other neurological measure correlated to the communication in a computer memory. In an alternative, the method may include indicating the CEP value or other neurological measure to the user and/or recipient.

FIGS. 25-26 list additional operations 2500, 2600 that may be performed as part of the method 2400. The elements of the operations 2500, 2600 may be performed in any operative order, and any one or any number of them may be omitted from the method 2400.

Referring to FIG. 25, the method 2400 may include any one or more of the additional operations 2500 for determining a CEP value. The method 2400 may include, at 2510 determining the CEP value at least in part by determining arousal values based on the sensor data and comparing a stimulation average arousal based on the sensor data with an expectation average arousal. The sensor data for arousal may include one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (fMRI) data, and functional near-infrared data (fNIR). The method 2400 may include, at 2520, determining the expectation average arousal based on further sensor data measuring a like involuntary response of the recipient while engaged with known audio-video stimuli.

In another aspect, the method 2400 may include, at 2530 playing the known audio-video stimuli comprising a known non-arousing stimulus and a known arousing stimulus. The method 2400 may include, at 2540 determining the CEP value at least in part by detecting one or more stimulus events based on the sensor data exceeding a threshold value for a time period. The method 2400 may include, at 2550 calculating one of multiple event powers for each of the one or more users and for each of the stimulus events and aggregating the event powers. The method 2400 may include, at 2560 assigning weights to each of the event powers based on one or more source identities for the sensor data.

Referring to FIG. 26, the method 2400 may include any one or more of the additional operations 2600 for determining a CEP value. The method 2400 may include, at 2610 determining the expectation average arousal at least in part by detecting one or more stimulus events based on the further sensor data exceeding a threshold value for a time period and calculating one of multiple expectation powers for the known audio-video stimuli for the one or more users and for each of the stimulus events. The method 2400 may include, at 2620 calculating the CEP power at least in part by calculating a ratio of the sum of the event powers to an aggregate of the expectation powers.

In a related aspect, the method 2400 may include, at 2630 determining valence values based on the sensor data. The sensor data for valence may include one or more of electroencephalographic (EEG) data, facial electromyography (fEMG) data, video facial action unit (FAU) data, brain machine interface (BMI) data, functional magnetic resonance imaging (fMRI) data, functional near-infrared data (fNIR) and positron emission tomography (PET). The method 2400 may include, at 2640 normalizing the valence values based on like values collected for the known audio-video stimuli. The method 2400 may include, at 2650 determining a valence error measurement based on comparing the valence values to a targeted valence for the communication. The method 2400 may include at 2660 setting the targeted valence value based on input from the user.

Figure 27:
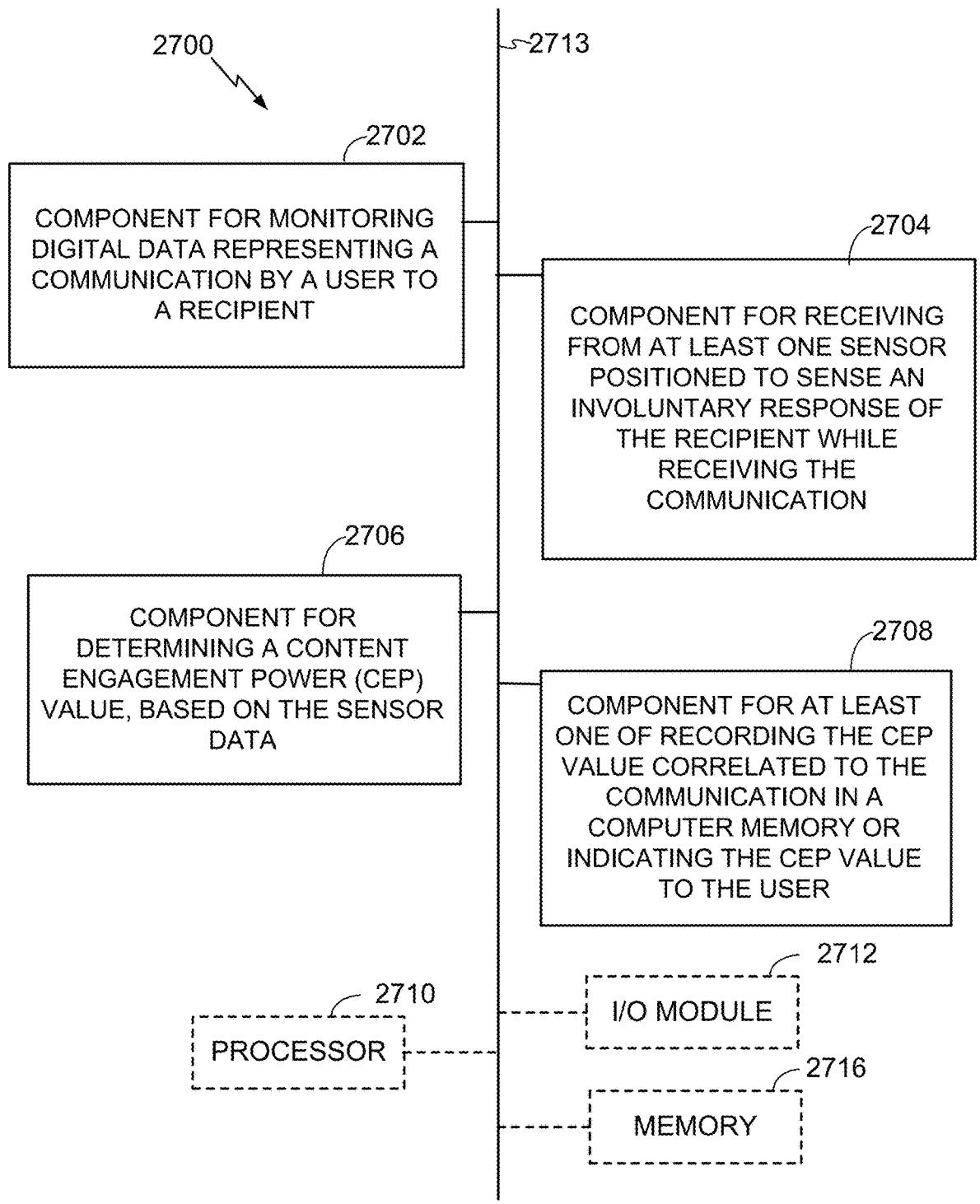
FIG. 27 is a conceptual block diagram illustrating components of an apparatus or system for enhancing interpersonal communication with neuro-physiological tells.

FIG. 27 is a conceptual block diagram illustrating components of an apparatus or system 2700 for rating effectiveness of personal communications, and related functions. The apparatus or system 2700 may include additional or more detailed components for performing functions or process operations as described herein. For example, the processor 2710 and memory 2716 may contain an instantiation of a process for calculating CEP in real time as described herein above. As depicted, the apparatus or system 2700 may include functional blocks that can represent functions implemented by a processor, software, or combination thereof (e.g., firmware).

As illustrated in FIG. 27, the apparatus or system 2700 may comprise an electrical component 2702 for monitoring, by at least one processor, digital data representing a communication by a user to a recipient. The component 2702 may be, or may include, a means for said monitoring. Said means may include the processor 2710 coupled to the memory 2716, and to an output of at least one biometric sensor 2714, the processor executing an algorithm based on program instructions stored in the memory. Such algorithm may include, for example, detecting a context of a communication, including that the communication is directed to eliciting a targeted neuro-physiological response, and creating an association between the communication and the targeted response.

The apparatus 2700 may further include an electrical component 2704 for receiving sensor data from at least one sensor positioned to sense an involuntary response of the recipient while receiving the communication. The component 2704 may be, or may include, a means for said receiving. Said means may include the processor 2710 coupled to the memory 2716, the processor executing an algorithm based on program instructions stored in the memory. Such algorithm may include a sequence of more detailed operations, for example, configuring a data port to receive sensor data from a known sensor, configuring a connection to the sensor, receiving digital data at the port, and interpreting the digital data as sensor data.

The apparatus 2700 may further include an electrical component 2706 for determining a Content Engagement Power (CEP) value for the communication, based on the sensor data. The component 2706 may be, or may include, a means for said determining. Said means may include the processor 2710 coupled to the memory 2716, the processor executing an algorithm based on program instructions stored in the memory. Such algorithm may include a sequence of more detailed operations, for example, as described in connection with FIG. 8.

The apparatus 2700 may further include an electrical component 2708 for at least one of recording the CEP value correlated to the communication in a computer memory or indicating the CEP value to the user. The component 2708 may be, or may include, a means for said recording or indicating. Said means may include the processor 2710 coupled to the memory 2716, the processor executing an algorithm based on program instructions stored in the memory. Such algorithm may include a sequence of more detailed operations, for example, encoding the CEP value and storing the encoded value in a computer memory, or sending the encoded value to an output device for presentation to the user.

The apparatus 2700 may optionally include a processor module 2710 having at least one processor. The processor 2710 may be in operative communication with the modules 2702-2708 via a bus 2713 or similar communication coupling. In the alternative, one or more of the modules may be instantiated as functional modules in a memory of the processor. The processor 2710 may initiate and schedule the processes or functions performed by electrical components 2702-2708.

In related aspects, the apparatus 2700 may include a network interface module 2712 or equivalent I/O port operable for communicating with system components over a computer network. A network interface module may be, or may include, for example, an Ethernet port or serial port (e.g., a Universal Serial Bus (USB) port), a Wi-Fi interface, or a cellular telephone interface. In further related aspects, the apparatus 2700 may optionally include a module for storing information, such as, for example, a memory device 2716. The computer readable medium or the memory module 2716 may be operatively coupled to the other components of the apparatus 2700 via the bus 2713 or the like. The memory module 2716 may be adapted to store computer readable instructions and data for effecting the processes and behavior of the modules 2702-2708, and subcomponents thereof, or the processor 2710, the method 2400 and one or more of the additional operations 2500-2600 disclosed herein, or any method for performance by a media player described herein. The memory module 2716 may retain instructions for executing functions associated with the modules 2702-2708. While shown as being external to the memory 2716, it is to be understood that the modules 2702-2708 can exist within the memory 2716 or an on-chip memory of the processor 2710.

The apparatus 2700 may include, or may be connected to, one or more biometric sensors (not shown), which may be of any suitable types. Various examples of suitable biometric sensors are described herein above. In alternative embodiments, the processor 2710 may include networked microprocessors from devices operating over a computer network. In addition, the apparatus 2700 may connect to an output device as described herein, via the I/O module 2712 or other output port.

Those of skill would further appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the application and design constraints imposed on the overall system. Skilled artisans may implement the described functionality in varying ways for each application, but such implementation decisions should not be interpreted as causing a departure from the scope of the present disclosure.

As used in this application, the terms "component", "module", "system", and the like are intended to refer to a computer-related entity, either hardware, a combination of hardware and software, software, or software in execution. For example, a component or a module may be, but are not limited to being, a process running on a processor, a processor, an object, an executable, a thread of execution, a program, and/or a computer. By way of illustration, both an application running on a server and the server can be a component or a module. One or more components or modules may reside within a process and/or thread of execution and a component or module may be localized on one computer and/or distributed between two or more computers.

Various aspects will be presented in terms of systems that may include several components, modules, and the like. It is to be understood and appreciated that the various systems may include additional components, modules, etc. and/or may not include all the components, modules, etc. discussed in connection with the figures. A combination of these approaches may also be used. The various aspects disclosed herein can be performed on electrical devices including devices that utilize touch screen display technologies, heads-up user interfaces, wearable interfaces, and/or mouse-and-keyboard type interfaces. Examples of such devices include VR output devices (e.g., VR headsets), AR output devices (e.g., AR headsets), computers (desktop and mobile), televisions, digital projectors, smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device (PLD) or complex PLD (CPLD), discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, 18PROM memory, registers, hard disk, a removable disk, a CD-ROM, digital versatile disk (DVD), Blu-Ray™, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a client device or server. In the alternative, the processor and the storage medium may reside as discrete components in a client device or server.

Furthermore, the one or more versions may be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips, or other format), optical disks (e.g., compact disk (CD), DVD, Blu-Ray™ or other format), smart cards, and flash memory devices (e.g., card, stick, or other format). Of course, those skilled in the art will recognize many modifications may be made to this configuration without departing from the scope of the disclosed aspects.

The previous description of the disclosed aspects is provided to enable any person skilled in the art to make or use the present disclosure. Various modifications to these aspects will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

In view of the exemplary systems described supra, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers.

The invention claimed is:

1. A method comprising:
    calibrating, by one or more processors, a cognitive appraisal model that is configured to map biometric data to one or more cognitive parameters randomized in a vector space;
    generating or modifying, by the one or more processors, one or more scripts based at least in part on modeling one or more character interactions by varying the one or more cognitive parameters with respect to at least one of the one or more scripts;
    for a plurality of segments of the one or more scripts, generating, by the one or more processors, based on the cognitive appraisal model, an estimated measure of effectiveness of a respective segment in producing one or more targeted neuro-physiological responses by a target user according to a targeted story arc, wherein the targeted story arc comprises a plurality of targeted neurophysiological values associated with respective intervals of a time sequence;
    selecting, by the one or more processors, one or more segments the plurality of segments as one or more next segments, the selecting based on the estimated measure of effectiveness of the segment;
    generating or modifying, by the one or more processors, a script based on the one or more next segments; and
    providing, by the one or more processors, the generated or modified script or electronic content generated based on the generated or modified script to the target user.

2. The method of claim 1, wherein generating the estimated measure of effectiveness comprises calculating a Content Engagement Power (CEP) value based on the cognitive appraisal model.

3. The method of claim 2, wherein calculating the CEP value comprises determining arousal values and comparing a stimulation average arousal with an expectation average arousal.

4. The method of claim 2, wherein calculating the CEP value comprises determining valence values.

5. The method of claim 1, wherein generating the estimated measure of effectiveness further comprises determining a neurological error measurement based on comparing predicted neuro-physiological responses to the targeted story arc.

6. The method of claim 1, wherein the cognitive appraisal model corresponds to a three-dimensional model used for complex emotions where a social hierarchy is involved.

7. The method of claim 1, wherein the neuro-physiological responses comprises one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (±MRI) data, or functional near-infrared data (fNIR).

8. The method of claim 1, the method further comprising:
    correlating, by the one or more processors, the biometric data to one or more neurological indicators, wherein the selecting the one or more segments is based on the one or more neurological indicators.

9. The method of claim 8, wherein a machine-learning algorithm is configured to process context-indicating data to correlate the biometric data to the neurological indicator.

10. A system comprising:
    a memory storing program instructions;
    one or more processors configured to execute the program instructions, and based on the executed program instructions, the one or more processors is further configured to:
        calibrate a cognitive appraisal model that is configured to map biometric data to one or more cognitive parameters randomized in a vector space;
        generate or modify a plurality of one or more scripts based at least in part on modeling the one or more character interactions while varying the one or more cognitive parameters with respect to at least one of the one or more scripts;
        for a plurality of segments of the one or more scripts, generate, based on the cognitive appraisal model, an estimated measure of effectiveness for each script of a respective segment in producing one or more targeted neuro-physiological responses by a target user based on according to a targeted story arc, wherein the targeted story arc comprises a plurality of targeted neuro-physiological values associated with respective intervals of a time sequence;
        select one or more segments of the plurality of segments as one or more next segments, the selecting based at least on the estimated measure of effectiveness;
        generate or modify a script based on the one or more next segments; and
        provide the generated or modified script or electronic content generated based on the generated or modified script to the target user.

11. The system of claim 10, wherein the one or more processors is configured to calculate a Content Engagement Power (CEP) value based on the cognitive appraisal model.

12. The system of claim 11, wherein the one or more processors is further configured to calculate the CEP value at least in part by determining arousal values and comparing a stimulation average arousal with an expectation average arousal.

13. The system of claim 11, wherein the one or more processors is further configured to calculate the CEP value at least in part by determining valence values.

14. A non-transitory computer-readable medium storing instructions that, when executed by at least one processor, cause the at least one processor to perform operations, the operations comprising:
   calibrate a cognitive appraisal model that is configured to map biometric data to one or more cognitive parameters randomized in a vector space;
   generate a plurality of one or more scripts based at least in part on modeling the one or more character interactions while varying the one or more cognitive parameters with respect to at least one of the one or more scripts;
   for a plurality of segments of the one or more scripts, generate, based on the cognitive appraisal model, an estimated measure of effectiveness for each script of a respective segment in producing one or more targeted neuro-physiological responses by a target user based on according to a targeted story arc, wherein the targeted story arc comprises a plurality of targeted neuro-physiological values associated with respective intervals of a time sequence;
   select one or more segments of the plurality of segments as one or more next segments, the selecting based at least on the estimated measure of effectiveness;
   generate or modify a script based on the one or more next segments; and
   provide the generated or modified script or electronic content generated based on the generated or modified script to the target user.

15. The non-transitory computer-readable medium of claim 14, wherein generating the estimated measure of effectiveness comprises calculating a Content Engagement Power (CEP) value based on the cognitive appraisal model.

16. The non-transitory computer-readable medium of claim 15, wherein calculating the CEP value comprises determining arousal values and comparing a stimulation average arousal with an expectation average arousal.

17. The non-transitory computer-readable medium of claim 15, wherein calculating the CEP value comprises determining valence values.

18. The non-transitory computer-readable medium of claim 14, wherein generating the estimated measure of effectiveness further comprises determining a neurological error measurement based on comparing predicted neuro-physiological responses to the targeted story arc.

19. The non-transitory computer-readable medium of claim 14, wherein the cognitive appraisal model corresponds to a three-dimensional model used for complex emotions where a social hierarchy is involved.

20. The non-transitory computer-readable medium of claim 14, wherein the neuro-physiological responses comprises one or more of electroencephalographic (EEG) data, galvanic skin response (GSR) data, facial electromyography (fEMG) data, electrocardiogram (EKG) data, video facial action unit (FAU) data, brain machine interface (BMI) data, video pulse detection (VPD) data, pupil dilation data, functional magnetic resonance imaging (±MRI) data, or functional near-infrared data (fNIR).

* * * * *

UNITED STATES PATENT AND TRADEMARK OFFICE
CERTIFICATE OF CORRECTION

Page 1 of 1

PATENT NO. : 12,274,551 B2
APPLICATION NO. : 16/923053
DATED : April 15, 2025
INVENTOR(S) : Arvel A. Chappell, III, Lewis S. Ostrover and Harold C. Mack It is certified that error appears in the above-identified patent and that said Letters Patent is hereby corrected as shown below:

In the Specification

In Column 1, Line 9, delete "US2019012783" and insert --PCT/US2019/012783--

In the Claims

In Column 45, Line 60, before "the plurality" insert --of--

Signed and Sealed this
Twentieth Day of May, 2025

Coke Morgan Stewart
*Acting Director of the United States Patent and Trademark Office*